United States Patent
Zhang et al.

(10) Patent No.: US 11,351,164 B2
(45) Date of Patent: Jun. 7, 2022

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: Liping Zhang, Princeton, NJ (US); Emily Charlotte Cherney, Princeton, NJ (US); James Aaron Balog, Princeton, NJ (US); Xiao Zhu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 540 days.

(21) Appl. No.: 16/328,473

(22) PCT Filed: Aug. 25, 2017

(86) PCT No.: PCT/US2017/048540
§ 371 (c)(1),
(2) Date: Feb. 26, 2019

(87) PCT Pub. No.: WO2018/039518
PCT Pub. Date: Mar. 1, 2018

(65) Prior Publication Data
US 2021/0283123 A1   Sep. 16, 2021

Related U.S. Application Data

(60) Provisional application No. 62/380,088, filed on Aug. 26, 2016.

(51) Int. Cl.
*A61K 31/4709* (2006.01)
*A61K 39/395* (2006.01)
*C07D 401/08* (2006.01)
*C07D 401/12* (2006.01)
*C07D 413/08* (2006.01)
*C07D 413/12* (2006.01)
*C07D 413/14* (2006.01)
*C07D 417/08* (2006.01)
*C07D 417/12* (2006.01)
*C07D 417/14* (2006.01)

(52) U.S. Cl.
CPC ...... *A61K 31/4709* (2013.01); *A61K 39/3955* (2013.01); *C07D 401/08* (2013.01); *C07D 401/12* (2013.01); *C07D 413/08* (2013.01); *C07D 413/12* (2013.01); *C07D 413/14* (2013.01); *C07D 417/08* (2013.01); *C07D 417/12* (2013.01); *C07D 417/14* (2013.01)

(58) Field of Classification Search
CPC .. C07D 401/08; C07D 401/12; C07D 413/08; C07D 413/12; C07D 413/14; C07D 417/08; C07D 417/12; C07D 417/14
See application file for complete search history.

(56) References Cited

U.S. PATENT DOCUMENTS

| 3,424,760 A | 1/1969 | Helsley et al. |
|---|---|---|
| 4,123,529 A | 10/1978 | Verge et al. |
| 6,288,230 B1 | 9/2001 | Chen et al. |
| 8,088,803 B2 | 1/2012 | Combs et al. |
| 2003/0114517 A1 | 6/2003 | Greenlee et al. |
| 2004/0072818 A1 | 4/2004 | Dunning et al. |
| 2004/0209871 A1* | 10/2004 | Fox .............. A61P 11/00 514/224.2 |
| 2006/0258719 A1 | 11/2006 | Combs et al. |
| 2010/0311712 A1* | 12/2010 | Chen .............. C07D 403/14 514/210.18 |
| 2016/0022619 A1 | 1/2016 | Balog et al. |
| 2016/0137653 A1 | 5/2016 | Beck et al. |
| 2019/0119215 A1* | 4/2019 | Shan .............. C07D 215/04 |
| 2019/0119216 A1* | 4/2019 | Cherney .............. A61K 31/47 |
| 2019/0135758 A1* | 5/2019 | Cherney .............. A61P 25/28 |
| 2019/0144416 A1* | 5/2019 | Williams .............. C07C 275/26 514/313 |
| 2019/0144417 A1* | 5/2019 | Williams .............. C07D 215/18 514/253.06 |
| 2019/0282714 A1* | 9/2019 | Donnelly .............. G01N 33/60 |
| 2020/0069646 A1* | 3/2020 | Balog .............. C07D 487/04 |
| 2020/0069695 A1* | 3/2020 | Balog .............. C07C 211/54 |
| 2020/0095231 A1* | 3/2020 | Balog .............. C07D 471/04 |
| 2020/0291008 A1* | 9/2020 | Kazmierski .......... C07D 215/14 |
| 2020/0317638 A1* | 10/2020 | Wang .............. A61P 35/00 |
| 2021/0206723 A1* | 7/2021 | Balog .............. C07D 401/12 |
| 2021/0221806 A1* | 7/2021 | Seitz .............. C07K 16/2818 |

(Continued)

FOREIGN PATENT DOCUMENTS

| CN | 109574988 | * | 4/2019 |
|---|---|---|---|
| WO | 99/29310 A2 | | 6/1999 |

(Continued)

OTHER PUBLICATIONS

Thurkauf; J. Med. Chem. 1997, 40, 1, 1-3. DOI: 10.1021/jm960637m (Year: 1997).*
Chemical Abstracts STN REGISTRY Database, record for RN 1316408-00-0, "5,8-Difluoro-4-[4-[1-[3-(4-methylphenyl)-1,2,4-oxadiazol-5-yl]ethyl]-1-piperazinyl]quinoline", entered into STN on Aug. 12, 2011. (Year: 2011).*
Zhang; ACS Med. Chem. Lett. 2021, 12, 3, 494-501. DOI: 10.1021/acsmedchemlett.1c00014 (Year: 2021).*
Chemical Abstracts STN REGISTRY Record for RN 477525-11-4, entered on Dec. 23, 2002. (Year: 2002).*
Moon; Journal for ImmunoTherapy of Cancer 2015, 3, 51. DOI 10.1186/S40425-015-0094-9 (Year: 2015).*
Ball, H.J. et al.. Characterization of an indoleamine 2, 3-dioxygenase-like protein found in humans and mice, Gene, Jul. 1, 2007, 396(1), 203-213.

(Continued)

*Primary Examiner* — Daniel R Carcanague
(74) *Attorney, Agent, or Firm* — BakerHostetler

(57) ABSTRACT

There are disclosed compounds that modulate or inhibit the enzymatic activity of indoleamine 2,3-dioxygenase (IDO), pharmaceutical compositions containing said compound and methods of treating proliferative disorders, such as cancer, viral infections and/or inflammatory disorders utilizing the compounds of the invention.

17 Claims, No Drawings

(56) References Cited

U.S. PATENT DOCUMENTS

| | | | |
|---|---|---|---|
| 2021/0290613 A1* | 9/2021 | Cherney | C07D 413/12 |
| 2021/0299126 A1* | 9/2021 | Balog | A61K 31/4439 |
| 2021/0355113 A1* | 11/2021 | Balog | C07D 413/14 |

FOREIGN PATENT DOCUMENTS

| | | | |
|---|---|---|---|
| WO | 2004/094409 A1 | 11/2004 | |
| WO | 2006/029879 A2 | 3/2006 | |
| WO | 2006/105021 A2 | 10/2006 | |
| WO | 2006/122150 A1 | 11/2006 | |
| WO | 2007/005874 A2 | 1/2007 | |
| WO | 2007/075598 | 7/2007 | |
| WO | 2008/036642 | 3/2008 | |
| WO | 2008/036653 | 3/2008 | |
| WO | 2008/132601 A1 | 11/2008 | |
| WO | 2009/009116 A2 | 1/2009 | |
| WO | 2009/044273 A2 | 4/2009 | |
| WO | 2009/056652 | 5/2009 | |
| WO | 2009/073620 | 6/2009 | |
| WO | 2010/019570 A2 | 2/2010 | |
| WO | 2010/077634 A1 | 7/2010 | |
| WO | 2011/028683 A1 | 3/2011 | |
| WO | 2011/056652 A1 | 5/2011 | |
| WO | 2011/070024 A1 | 6/2011 | |
| WO | 2011/107553 A1 | 9/2011 | |
| WO | 2011/131407 A1 | 10/2011 | |
| WO | 2011/140249 A2 | 11/2011 | |
| WO | 2012/032433 A1 | 3/2012 | |
| WO | 2012/142237 A1 | 10/2012 | |
| WO | 2012/145493 A1 | 10/2012 | |
| WO | 2013/079174 A1 | 6/2013 | |
| WO | 2013/087699 A1 | 6/2013 | |
| WO | 2013/119716 A1 | 8/2013 | |
| WO | 2013/132044 A1 | 9/2013 | |
| WO | 2013/169264 A1 | 11/2013 | |
| WO | 2014/008218 A1 | 1/2014 | |
| WO | 2014/036357 A1 | 3/2014 | |
| WO | 2015/006520 A1 | 1/2015 | |
| WO | 2016/073738 A2 | 5/2016 | |
| WO | 2016/073770 A1 | 5/2016 | |
| WO | 2016/073774 A2 | 5/2016 | |
| WO | WO-2018039512 A1* | 3/2018 | C07D 487/04 |
| WO | WO-2019179369 A1* | 9/2019 | C07D 401/08 |

OTHER PUBLICATIONS

Ball, H.J., et al., "Characterization of an indoleamine 2,3-dioxygenase-like protein found in humans and mice", Gene, 2007, 396(1), 203-213.

Brandacher, et al., Prognostic value of indoleamine 2, 3-dioxygenase expression in colorectal cancer: effect on tower-infiltrating T cells, Clin. Cancer Res., Feb. 15, 2006, 12(4), 1144-1151.

Bundgaard, "Design of Prodrugs: Bioreversible derivatives for various functional groups and chemical entities", 1985, Design of Prodrugs, 1985, 96 pages.

Bundgaard, H. Chapter 5: "Design and Application or Produgs", A Textbook of Drug Design and Development, pp. 113-191, Krogsgaard-Larsen, P. et al., eds., Harwood Academic Publishers, 1991.

Bundgaard, H.(C) Means to enhance penetration: (1) Prodrugs as a means to improve the delivery of peptide drugs, Adv. Drug Deliv. Rev., Jan. 1, 1992, 8(1), 1-38.

Goldstein et al., "Biological efficacy of a chimeric antibody to the epidermal growth factor receptor in human tumor xenograft model", Clin. Cancer Res., Nov. 1, 1995, 1(11): 1311-1318.

Ishiyama, et al., Palladium (0)-catalyzed cross-coupling reaction of alkoxydiboron with haloarenes: a direct procedure for arylboronic esters, The Journal of Org Chem., Nov. 1995, 60(23), 7508-7510.

Kakeya et al., Studies on Prodrugs of Cephalosporins. I. Synthesis and Biological Properties of Glycyloxybenzoyloxymethyl and Glycylaminobenzoyloxymethyl Esters of 7B-[2-(2-Aminothiazol-4-yl)-(Z)-2-methoxyiminoacetamido]-3-methyl-3-cephem-4-carboxylic Acid, Chem. Pharm. Bull., Feb. 25, 1984, 32(2), 692-698.

Kohl et al., "Inhibition of farnesyltransferase induces regression of mammary and salivary carcinomas in ras transgenic mice", Nat. Med., Aug. 1995, 1(8), 792-797.

Littlejohn et al., "Expression and purification of recombinant human indoleamine 2, 3-dioxygenase", Prot. Exp. and Purif., Jun. 1, 2000, 19(1), 22-29.

Nielsen et al., "Glycolamide esters as biolabile prodrugs of carboxylic acid agents: synthesis, stability, bioconversion, and physicochemical properties", J. Pharm. Sci., Apr. 1988, 77(4), 285-298.

Notari, Theory and Practice of Prodrug Kinetics, Methods in Enzymology, Academic Press, 1985, 112, 309-396.

Sambrook et al., "Molecular Cloning", Third Edition, Cold Spring Harbor Laboratory Press, © 2001, 21 pages.

Sarkar et al., "Induction of Indoleamine 2, 3-dioxygenase by interferon-? in human islets", Diabetes, Jan. 1, 2007, 56(1), 72-79.

Sausville et al., "Cyclin-dependent kinase modulators studied at the NCI: pre-clinical and clinical studies", Curr. Med. Chem. Anti-Cancer Agents, Jan. 1, 2003, 3(1), 47-56.

Scheller et al., "Paclitaxel Balloon Coating, A Novel Method for Prevention and Therapy of Restenosis", Circulation, Aug. 17, 2004, 110(7), 810-814.

Sekulic et al., "A direct linkage between the phosphoinositide 3-kinase-AKT signaling pathway and the mammalian target of rapamycin in mitogen-stimulated and transformed cells", Cancer Res , Jul. 1, 2000, 60(13), 3504-3513.

Serafini et al., "Myeloid suppressor cells in cancer: recruitment, phenotype, properties, and mechanisms of immune suppression", In Seminars in Cancer Biol., Feb. 1, 2006, 16(1), 53-65.

Vlahos et al., "A specific inhibitor of phosphatidyleinositol 3-kinase, 2-(4-morpholinyl)-8-phenyl-4H-1-benzopyran-4-one (LY294002)", J. Biol. Chem, Feb. 18, 1994, 269(7), 5241-5248.

* cited by examiner

INHIBITORS OF INDOLEAMINE 2,3-DIOXYGENASE AND METHODS OF THEIR USE

CROSS-REFERENCE TO RELATED APPLICATIONS

This application is the National Stage Application of International Patent Application No. PCT/US2017/048540 filed Aug. 25, 2017, which claims the benefit of U.S. Provisional Application No. 62/380,088, filed Aug. 26, 2016. Each of these applications is incorporated by reference herein in its entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini, P. et al., *Semin. Cancer Biol.* 16(1):53-65 (February 2006) and Ball, H. J. et al., Gene, 396(1):203-213 (Jul. 1, 2007)).

IDO plays a major role in immune regulation, and its immunosuppressive function manifests in several manners. Importantly, IDO regulates immunity at the T cell level, and a *nexus* exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant tumor metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine: p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in PCT Publication No. WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE INVENTION

The invention is directed to compounds of formula I or formula II:

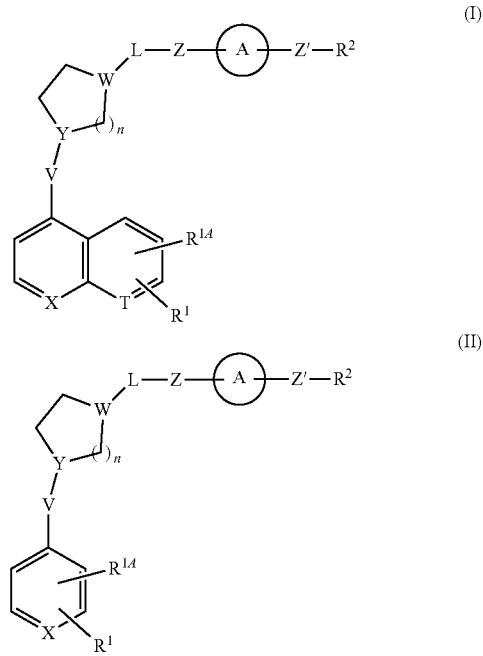

wherein X is CH or N: T is CH or N; V is a bond or O; n is 0, 1, 2, 3, or 4; Y is CH or N; W is CH, C(C$_1$-C$_6$alkyl), or N; L is a C$_1$-C$_6$alkylene optionally substituted with 1, 2, or 3 substituents independently selected from $C_1$-$C_6$alkyl and —$C_1$-$C_6$alkO$C_1$-$C_6$alkyl; Z is a bond, —NH—, or —N($C_1$-$C_6$alkyl); A is triazolyl, oxadiazolyl, thiadiazolyl, oxazolyl, thiazolyl, or imidazolyl; Z' is a bond, —NH—, or —N($C_1$-$C_6$alkyl); $R^1$ is H, halo, $C_1$-$C_6$alkyl, —O$C_1$-$C_6$alkyl, or $C_1$-$C_6$haloalkyl; $R^{1A}$ is H, halo, $C_1$-$C_6$alkyl, —O$C_1$-$C_6$alkyl, or $C_1$-$C_6$haloalkyl; and $R^2$ is aryl optionally substituted with one, two, or three substituents independently selected from halo, —CN, $C_1$-$C_6$alkyl, —O$C_1$-$C_6$alkyl, and heteroaryl optionally substituted with $C_1$-$C_6$alkyl; or $R^2$ is $C_3$-$C_{10}$cycloalkyl optionally substituted with one, two, or three substituents independently selected from halo, —CN, $C_1$-$C_6$alkyl, —O$C_1$-$C_6$alkyl, or heteroaryl optionally substituted with $C_1$-$C_6$alkyl; or $R^2$ is $C_1$-$C_6$alk-O—$C_1$-$C_6$alkyl; or $R^2$ is heteroaryl optionally substituted with one, two, or three substituents independently selected from halo, —CN, $C_1$-$C_6$alkyl, —O$C_1$-$C_6$alkyl.

Also within the scope of the invention are pharmaceutically acceptable salts, stereoisomers, tautomers, and solvates of the compounds of formula I and formula II.

The invention is also directed to pharmaceutical compositions comprising one or more compounds of formula I and/or formula II. The invention is also directed to methods of treating cancer using one or more compounds of formula I and/or formula II.

DETAILED DESCRIPTION OF THE
INVENTION COMPOUNDS OF THE
INVENTION

The present invention is directed to compounds of formula I and formula II:

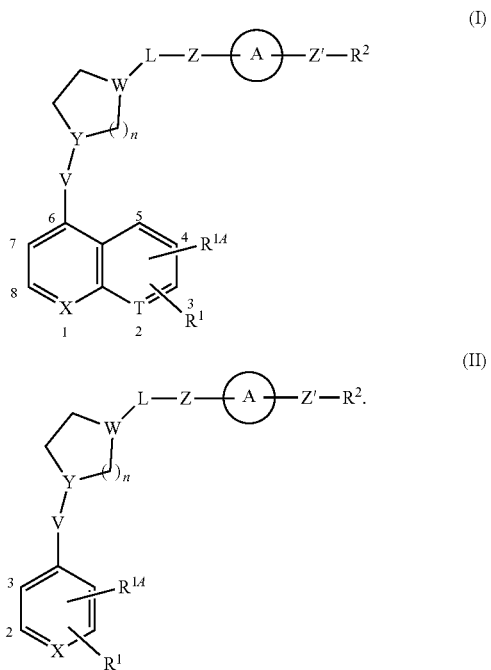

According to the disclosure, X is CH or N. In some aspects, X is CH. In other aspects, X is N.

According to the disclosure T is CH or N. In some aspects, T is CH. In other aspects, T is N.

In some embodiments, X is CH and T is CH. In other embodiments, X is N and T is CH. In other embodiments, X is CH and T is N. In other embodiments, X is N and T is N.

According to the disclosure, V is a bond or —O—. In preferred aspects, V is a bond. In other aspects, V is —O—.

According to the disclosure, Y is CH or N. In some aspects, Y is CH. In other aspects, Y is N. In alternative embodiments, Y is —C($C_1$-$C_6$alkyl), for example, —C(CH$_3$)— or C(CH$_2$CH$_3$).

According to the disclosure. W is CH, —C($C_1$-$C_6$alkyl)-, or N. In some aspects, W is CH. In other aspects, W is —C($C_1$-$C_6$alkyl)-, for example, —C(CH$_3$)—, —C(CH$_2$CH$_3$)—, —C(i-propyl), or —C(butyl)-. In other aspects, W is N. In some aspects, W is CH or —C($C_1$-$C_6$alkyl)-. In other aspects, W is CH or N. In yet other aspects. W is N or —C($C_1$-$C_6$alkyl)-.

In some aspects, Y is CH and W is CH. In other aspects, Y is CH and W is N. In other aspects, Y is N and W is CH. In still other aspects, Y is N and W is N. In some aspects, Y is CH and W is C($C_1$-$C_6$alkyl). In other aspects, Y is N and W is C($C_1$-$C_6$alkyl).

According to the disclosure, n is 0, 1, 2, 3, or 4. In preferred aspects, n is 2. In other aspects, n is 0. In other aspects, n is 1. In yet other aspects, n is 3. In still other aspects, n is 4. In some aspects, n is 0 to 2 or 1 to 2. In yet other aspects, n is 1 to 3.

According to the disclosure, L is an unsubstituted $C_1$-$C_6$alkylene, for example, unsubstituted $C_1$-$C_5$alkylene, $C_1$-$C_4$alkylene, $C_1$-$C_3$alkylene, $C_1$-$C_2$alkylene, or $C_1$alkylene. In other aspects, L is a $C_1$-$C_6$alkylene, for example, $C_1$-$C_5$alkylene, $C_1$-$C_4$alkylene, $C_1$-$C_3$alkylene, $C_1$-$C_2$alkylene, or $C_1$alkylene, substituted with 1, 2, or 3 substituents, preferably 1 or 2 substituents, independently selected from $C_1$-$C_6$alkyl (e.g., methyl, ethyl, isopropyl) and —$C_1$-$C_6$alkO$C_1$-$C_6$alkyl. In a preferred aspect, L is a $C_1$alkylene substituted with one $C_1$-$C_6$alkyl (e.g., methyl or ethyl) substituent. In another preferred aspect. L is a $C_1$alkylene substituted with one —$C_1$-$C_6$alkO$C_1$-$C_6$alkyl (e.g., —CH$_2$—O-ethyl or —CH$_2$—O-methyl) substituent.

According to the disclosure, Z is a bond. —NH—, or —N($C_1$-$C_6$alkyl). In some aspects, Z is a bond. In other aspects, Z is —NH—. In yet other aspects, Z is —N($C_1$-$C_6$alkyl), for example, —N(CH$_3$)—, —N(CH$_2$CH$_3$)—, —N(i-propyl)-, and —N(t-butyl)-. In some aspects, Z is —NH— or —N($C_1$-$C_6$alkyl). In other aspects. Z is a bond or —NH—.

According to the disclosure, A is a triazolyl, oxadiazolyl, thiadiazolyl, oxazolyl, thiazolyl, or imidazolyl. In some embodiments, A is triazolyl, for example, a 1H-1,2,3-triazolyl, a 2H-1,2,3-triazolyl, a 1H-1,2,4-triazolyl, or a 4H-1,2,4-triazolyl. The triazolyl can be attached to the compounds of formula I or formula I through the carbons of the triazolyl ring. A preferred triazolyl is

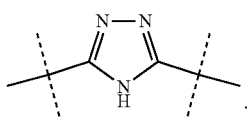

In other embodiments, A is oxadiazolyl, for example, a 1,2,3-oxadiazolyl, a 1,2,4-oxadiazolyl, a 1,2,5-oxadiazolyl, or a 1,3,4-oxadiazolyl. The oxadiazolyl can be attached to the compounds of formula I or formula I through the carbons of the triazolyl ring. A preferred oxadiazolyl is

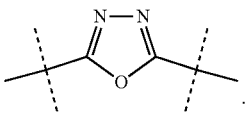

In other aspects, A is thiadiazolyl, for example, a 1,2,4-thiadiazolyl or a 1,3,4-thiadiazolyl. The thiadiazolyl can be attached to the compounds of formula I or formula II through the carbons of the thiadiazolyl ring. A preferred thiadiazolyl is

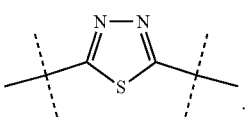

In other aspects, A is oxazolyl. The oxazolyl can be attached to the compounds of formula I or formula II through any two available ring carbons. The remaining oxazolyl ring carbon can be optionally substituted by, for example, halo (e.g., F, Cl, or Br) or $C_1$-$C_6$alkyl (e.g., methyl of ethyl). A preferred oxazolyl is

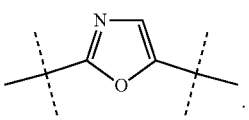

In other aspects, A is thiazolyl. The thiazolyl can be attached to the compounds of formula I or formula II through any two available ring carbons. The remaining thiazolyl ring carbon can be optionally substituted by, for example, halo (e.g., F, Cl, or Br) or $C_1$-$C_6$alkyl (e.g., methyl of ethyl). A preferred thiazolyl is

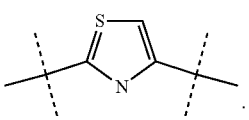

Another preferred thiazolyl is

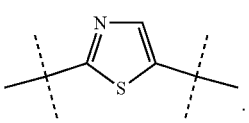

In other aspects, A is imidazolyl. The imidazolyl can be attached to the compounds of formula I or formula II through any two available ring carbons. The remaining imidazolyl ring carbon can be optionally substituted by, for example, halo (e.g., F, Cl, or Br) or $C_1$-$C_6$alkyl (e.g., methyl of ethyl). A preferred imidazolyl is

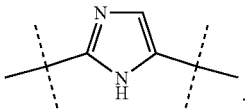

According to the disclosure, Z' is a bond, —NH—, or —N($C_1$-$C_6$alkyl). In some aspects, Z' is a bond. In other aspects, Z' is —NH—. In yet other aspects, Z' is —N($C_1$-$C_6$alkyl), for example,
—N(CH$_3$)—, —N(CH$_2$CH)—. —N(i-propyl)-, and —N(t-butyl)-. In some aspects. Z' is —NH— or —N($C_1$-$C_6$alkyl). In other aspects, Z' is a bond or —NH—.

According to the disclosure, $R^1$ is H, halo, $C_1$-$C_6$alkyl, —O$C_1$-$C_6$alkyl, or $C_1$-$C_6$haloalkyl. In some aspects, $R^1$ is H. In some aspects. $R^1$ is halo (F, Cl, Br, or I), preferably F. In other aspects, $R^1$ is $C_1$-$C_6$alkyl, for example, methyl, ethyl, isopropyl, butyl, and t-butyl. In some aspects, $R^1$ is —O$C_1$-$C_6$alkyl, for example, methoxy, ethoxy, isopropoxy, butoxy. In yet other aspects, R is $C_1$-$C_6$haloalkyl, for example, —CF$_3$. In some aspects, $R^1$ is halo, $C_1$-$C_6$alkyl, or $C_1$-$C_6$haloalkyl In yet other aspects. $R^1$ is —O$C_1$-$C_6$alkyl. In some aspects, $R^1$ is halo, $C_1$-$C_6$alkyl, —O$C_1$-$C_6$alkyl, or $C_1$-$C_6$haloalkyl. In other aspects, $R^1$ is halo or $C_1$-$C_6$haloalkyl.

In those aspects of the disclosure comprising compounds of formula I, when $R^1$ is halo, $C_1$-$C_6$alkyl, —O$C_1$-$C_6$alkyl, or $C_1$-$C_6$haloalkyl, the $R^1$ is preferably present at the 4-carbon position of the quinoline ring. In other aspects of the disclosure comprising compounds of formula I, when $R^1$ is halo, $C_1$-$C_6$alkyl, —O$C_1$-$C_6$alkyl, or $C_1$-$C_6$haloalkyl, the $R^1$ can be present at the 2-carbon position of the quinoline ring. Preferably, in those aspects of the disclosure comprising compounds of formula I, when $R^1$ is F or CF$_3$ at the 4-carbon position of the quinoline ring.

In those aspects of the disclosure comprising compounds of formula II, when $R^1$ is halo, $C_1$-$C_6$alkyl, —O$C_1$-$C_6$alkyl, or $C_1$-$C_6$haloalkyl, the $R^1$ is preferably present at the 2-carbon position of the pyridyl ring. In other aspects of the disclosure comprising compounds of formula II, when $R^1$ is halo, $C_1$-$C_6$alkyl, —O$C_1$-$C_6$alkyl, or $C_1$-$C_6$haloalkyl, the $R^1$ can be present at the 3-carbon position of the pyridyl ring. Preferably, in those aspects of the disclosure comprising compounds of formula II, when $R^1$ is F or CF$_3$ at the 2-carbon position of the pyridyl ring.

According to the disclosure, $R^{1A}$ is H, halo, $C_1$-$C_6$alkyl, —O$C_1$-$C_6$alkyl, or $C_1$-$C_6$haloalkyl. In preferred aspects, $R^{1A}$ is H. In some aspects, $R^{1A}$ is halo (F, Cl, Br, or I). In other preferred aspects, $R^{1A}$ is $C_1$-$C_6$alkyl, for example, methyl, ethyl, isopropyl, butyl, and t-butyl. In some aspects, $R^{1A}$ is —O$C_1$-$C_6$alkyl, for example, methoxy, ethoxy, isopropoxy, butoxy. In yet other aspects, $R^{1A}$ is $C_1$-$C_6$haloalkyl, for example, —CF$_3$.

In some aspects of the disclosure, $R^2$ is unsubstituted aryl, for example, unsubstituted phenyl or naphthyl, preferably phenyl. In preferred aspects, $R^2$ is aryl substituted with one, two, or three substituents, preferably one or two substituents. The $R^2$ substituents, which can be referred to as one or more $R^4$, are preferably independently selected from halo (F, Cl, Br, or I), —CN, $C_1$-$C_6$alkyl (e.g., methyl, ethyl, isopropyl, butyl, t-butyl), —O$C_1$-$C_6$alkyl (e.g., methoxy, ethoxy, isopropoxy, butoxy), and heteroaryl (e.g., triazolyl, oxadiazolyl, thiadiazolyl, oxazolyl, thiazolyl, imidazolyl, or pyridyl) optionally substituted with $C_1$-$C_6$alkyl (e.g., methyl, ethyl, isopropyl, butyl, t-butyl).

In some aspects of the disclosure, $R^2$ is unsubstituted $C_3$-$C_{10}$cycloalkyl, for example, unsubstituted cyclopropyl, cyclobutyl, cyclopentyl, or cyclohexyl. In other aspects, $R^2$ is $C_3$-$C_{10}$cycloalkyl optionally substituted with one, two, or three substituents, preferably one or two substituents. The $R^2$ substituents, which can be referred to as one or more $R^4$, are preferably independently selected from halo (F, Cl, Br, or I), —CN, $C_1$-$C_6$alkyl (e.g., methyl, ethyl, isopropyl, butyl, t-butyl), —O$C_1$-$C_6$alkyl (e.g., methoxy, ethoxy, isopropoxy, butoxy), and heteroaryl (e.g., triazolyl, oxadiazolyl, thiadiazolyl, oxazolyl, thiazolyl, imidazolyl, or pyridyl) optionally substituted with $C_1$-$C_6$alkyl (e.g., methyl, ethyl, isopropyl, butyl, t-butyl).

In some aspects of the disclosure, $R^2$ is $C_1$-Calk-O—$C_1$-$C_6$alkyl, for example, $C_1$-$C_5$alk-O—$C_1$-$C_6$alkyl, $C_1$-$C_4$alk-O—$C_1$-$C_6$alkyl, $C_1$-$C_3$alk-O—$C_1$-$C_6$alkyl, $C_1$-$C_2$alk-O—$C_1$-$C_6$alkyl, $C_1$alk-O—$C_1$-$C_6$alkyl, $C_1$-Calk-O—$C_1$-$C_5$alkyl, $C_1$-$C_6$alk-O—$C_1$-$C_4$alkyl, $C_1$-$C_6$alk-O—$C_1$-$C_3$alkyl, $C_1$-$C_6$alk-O—$C_1$-$C_2$alkyl, or $C_1$-$C_6$alk-O—$C_1$alkyl.

In some aspects of the disclosure, $R^2$ is unsubstituted heteroaryl, for example, pyridyl. In other aspects. $R^2$ is heteroaryl, for example, pyridyl, substituted with one, two, or three substituents, preferably one or two substituents. The $R^2$ substituents, which can be referred to as one or more $R^4$, are preferably independently selected from selected from halo (F, Cl, Br, or I), —CN, $C_1$-$C_6$alkyl (e.g., methyl, ethyl, isopropyl, butyl, t-butyl), —O$C_1$-$C_6$alkyl (e.g., methoxy, ethoxy, isopropoxy, butoxy), and heteroaryl (e.g., triazolyl, oxadiazolyl, thiadiazolyl, oxazolyl, thiazolyl, imidazolyl, or pyridyl) optionally substituted with $C_1$-$C_6$alkyl (e.g., methyl, ethyl, isopropyl, butyl, t-butyl).

The invention also encompasses the pharmaceutically acceptable salts, stereoisomers, tautomers, and solvates of formulas I and II.

Sub-formulas of formula I include those wherein n is 2, V is a bond, Y is CH, W is CH, L is $C_1$alkylene, Z is a bond, and Z' is a bond, for example,

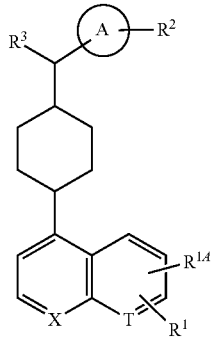

(I-A)

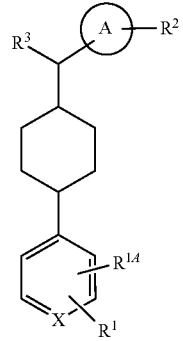

(II-A)

wherein X is CH and $R^3$ is $C_1$-$C_6$alkyl, preferably methyl. In other embodiments of formula I-A and formula II-A, X is N and $R^3$ is $C_1$-$C_6$alkyl, preferably methyl. In other aspects. X is CH and T is CH. In some aspects, X is N and T is CH. In other aspects, X is CH and T is N. In other aspects, X is N and T is N. In certain of these embodiments, it is preferred that $R^2$ is a substituted phenyl. The invention also encompasses the pharmaceutically acceptable salts, stereoisomers, tautomers, and solvates of formulas I-A and II-A.

Sub-formulas of formula I include those wherein n is 2, V is a bond, Y is CH, W is CH, L is $C_1$alkylene, Z is NH, and Z is a bond, for example,

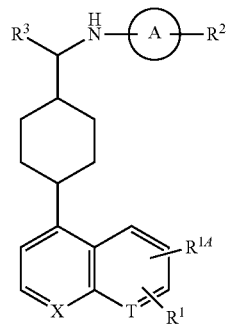

(I-B)

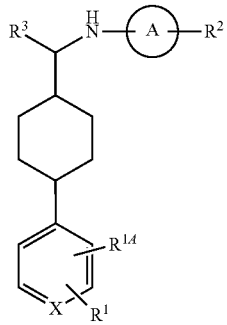

(II-B)

wherein X is CH and $R^3$ is $C_1$-$C_6$alkyl, preferably methyl. In other embodiments of formula I-B and formula II-B, X is N and $R^3$ is $C_1$-$C_6$alkyl, preferably methyl. In other aspects, X is CH and T is CH. In some aspects, X is N and T is CH. In other aspects, X is CH and T is N. In other aspects, X is N and T is N. In certain of these embodiments, it is preferred that $R^2$ is a substituted phenyl. The invention also encompasses the pharmaceutically acceptable salts, stereoisomers, tautomers, and solvates of formulas I-B and II-B.

Sub-formulas of formula I include those wherein n is 2, V is a bond, Y is CH, W is CH, L is $C_1$alkylene, Z is a bond, and Z' is NH, for example,

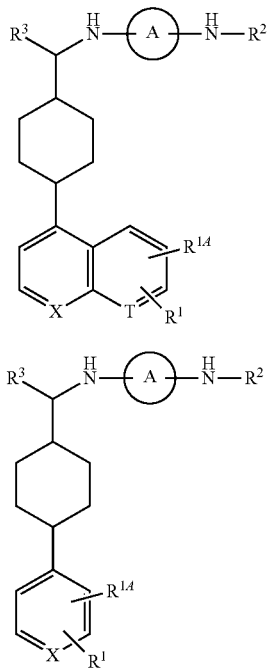

wherein X is CH and $R^3$ is $C_1$-$C_6$alkyl, preferably methyl. In other embodiments of formula I-C and formula II-C, X is N and $R^3$ is $C_1$-$C_6$alkyl, preferably methyl. In other aspects. X is CH and T is CH. In some aspects, X is N and T is CH. In other aspects, X is CH and T is N. In other aspects, X is N and T is N. In certain of these embodiments, it is preferred that $R^2$ is a substituted phenyl. The invention also encompasses the pharmaceutically acceptable salts, stereoisomers, tautomers, and solvates of formulas I-C and II-C.

In another embodiment, the compounds of the invention have human IDO $IC_{50}$ values >50 nM. In another embodiment, the compounds of the invention have human IDO $IC_{50}$ values ≤50 nM. In another embodiment, the compounds of the invention have human IDO $IC_{50}$ values <5 nM.

OTHER EMBODIMENTS OF THE INVENTION

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof. a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple mycloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome. CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barré syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur: and haematopoietic growth factors.

Other anticancer agent(s) include antibody therapeutics such as trastuzumab (HERCEPTINT®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides. DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) ber/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas I and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovirdipivoxil [bis(POM)-PMEA]; lobucavir (BMS-180194); BCH-10652; cmtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfmavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of Formula I or formula II is administered with one or more immuno-oncology agents. The immuno-oncology agents used herein, also known as cancer immunotherapies, are effective to enhance, stimulate, and/or upregulate immune responses in a subject.

In one aspect, the Compound of Formula I or formula II is sequentially administered prior to administration of the immuno-oncology agent. In another aspect, the Compound of Formula I or formula II is administered concurrently with the immunology-oncology agent. In yet another aspect, the Compound of Formula I or formula II is sequentially administered after administration of the immuno-oncology agent.

In another aspect, the Compound of Formula I or formula II may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin αTNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-ß, VEGF, and other immunosuppressive cytokines) or a cytokine that stimulates T cell activation, for stimulating an immune response.

In one aspect, T cell responses can be stimulated by a combination of the Compound of Formula I or formula I and one or more of (i) an antagonist of a protein that inhibits T cell activation (e.g., immune checkpoint inhibitors) such as CTLA-4, PD-1, PD-L1. PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70. CD27, CD40, DR3 and CD28H.

Other agents that can be combined with the Compound of Formula I or formula II for the treatment of cancer include antagonists of inhibitory receptors on NK cells or agonists of activating receptors on NK cells. For example, the Compound of Formula I or formula II can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of Formula I or formula II can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOYX (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MEDI4736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonist CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I and/or Formula II, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment: the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration. e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol ⁂ is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the terms "alkyl" and "alkylene" (also referred to as "alk") are intended to include both branched and straight-chain saturated aliphatic hydrocarbon groups having the specified number of carbon atoms. For example, "C$_1$-C$_6$ alkyl" or "C$_{1-6}$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). "C$_1$-C$_6$alkylene" denotes alkylene having 1 to 6 carbon atoms. Example alkylene groups include, but are not limited to, methylene (—CH$_2$—), ethylene (—CH$_2$CH$_2$—), and the like.

As used herein, "aryl" refers to an aromatic ring system which includes, but not limited to phenyl, biphenyl, indanyl, 1-naphthyl, 2-naphthyl and terahydronaphthyl.

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

As used herein, "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

As referred to herein, the term "substituted" means that at least one hydrogen atom is replaced with a non-hydrogen group, provided that normal valencies are maintained and that the substitution results in a stable compound.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two: generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition. Pharmaceutical Press, London, UK (2012). The disclosure of which is hereby incorporated by reference.

In addition, compounds of formula I and formula II may have prodrug forms. Any compound that will be converted in vivo to provide the bioactive agent (i.e., a compound of formula I or II) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112: 309-396, Academic Press (1985);

b) Bundgaard, H., Chapter 5: "Design and Application of Podrugs", *A Textbook of Drug Design and Development*, pp. 113-191, Krogsgaard-Larsen, P. et al., eds., Harwood Academic Publishers (1991);

c) Bundgaard, H., *Adv. Drug Deliv. Rev.*, 8:1-38 (1992):

d) Nielsen, N. M. et al., *J. Pharm. Sci.*, 77:285 (1988):

e) Kakeya, N. et al., *Chem. Pharm. Bull.*, 32:692 (1984); and g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I or formula II compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I or formula II include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*. VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

Reference can also be made to International Publication Nos. WO2016/073738, WO2016/073770, and WO2016/073774.

References to many of these chemical transformations employed herein can be found in Smith, M. B. et al., *March's Advanced Organic Chemistry Reactions. Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene. T. W. et al., *Protective Groups in Organic Synthesis*, Third Edition, Wiley-Interscience, New York (1999).

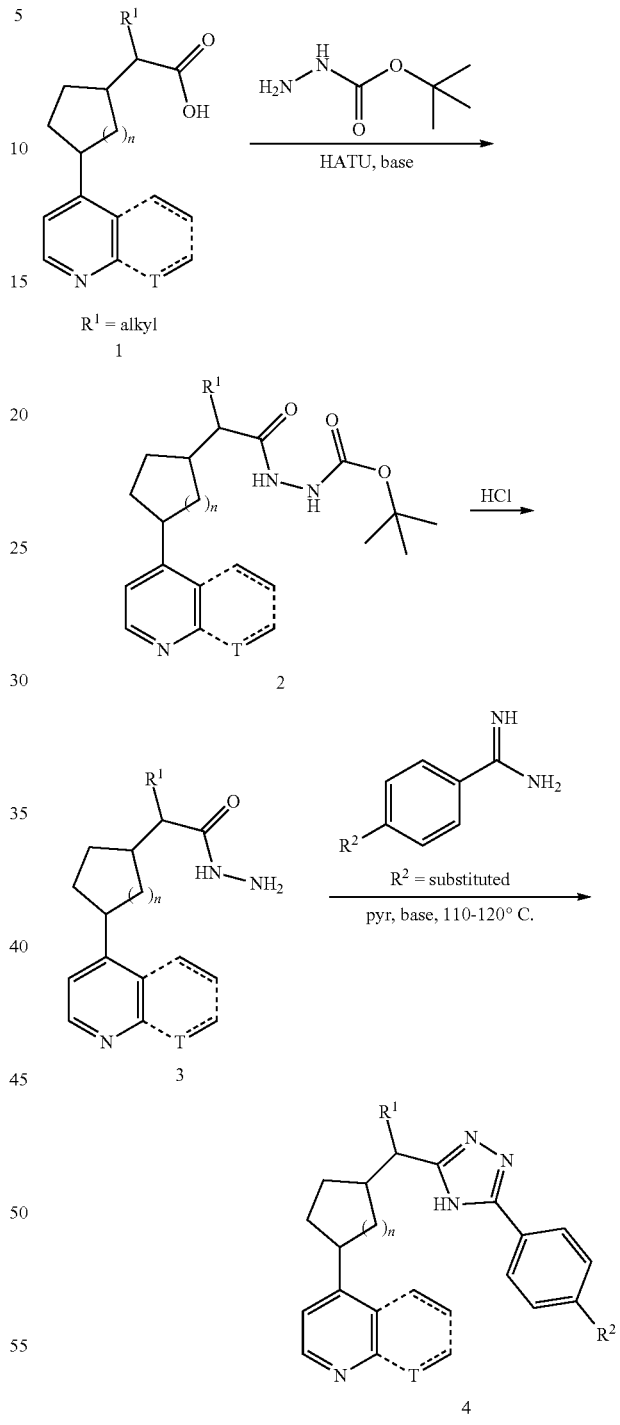

Triazoles 4 could be synthesized in three steps from compound 1 in the following manner. Treatment of acid 1 with tert-butyl carbazate, followed by deprotection of the Boc group with HCl afforded hydrazide 3. Condensation of compound 3 with a substituted benzimidamide hydrochloride with base in pyridine at 110° C. gave triazole 4.

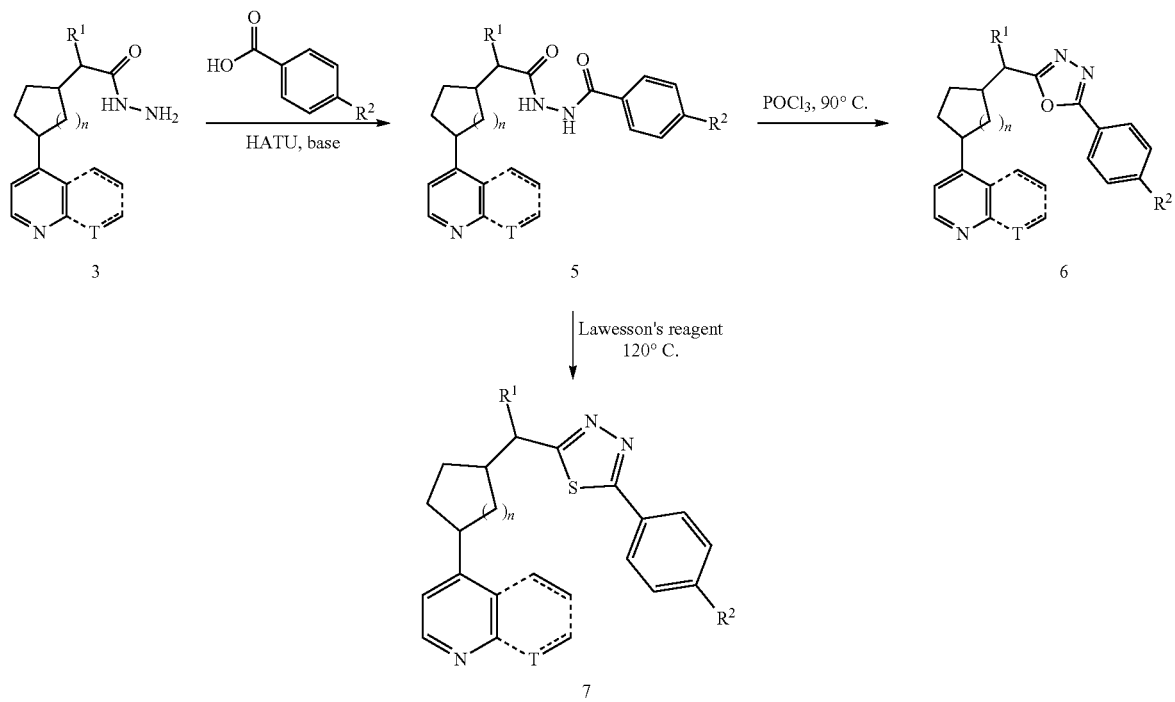
The synthesis of oxadiazole 6 or thiazole 7 commenced by HATU coupling of hydrazide 3 with a substituted carboxylic acid to give intermediate 5. Reaction of compound 5 with POCl$_3$ at elevated temperatures induced cyclization to oxadiazole 6. However, when compound 5 was reacted with Lawesson's reagent, thiazole 7 was obtained.
Scheme 3
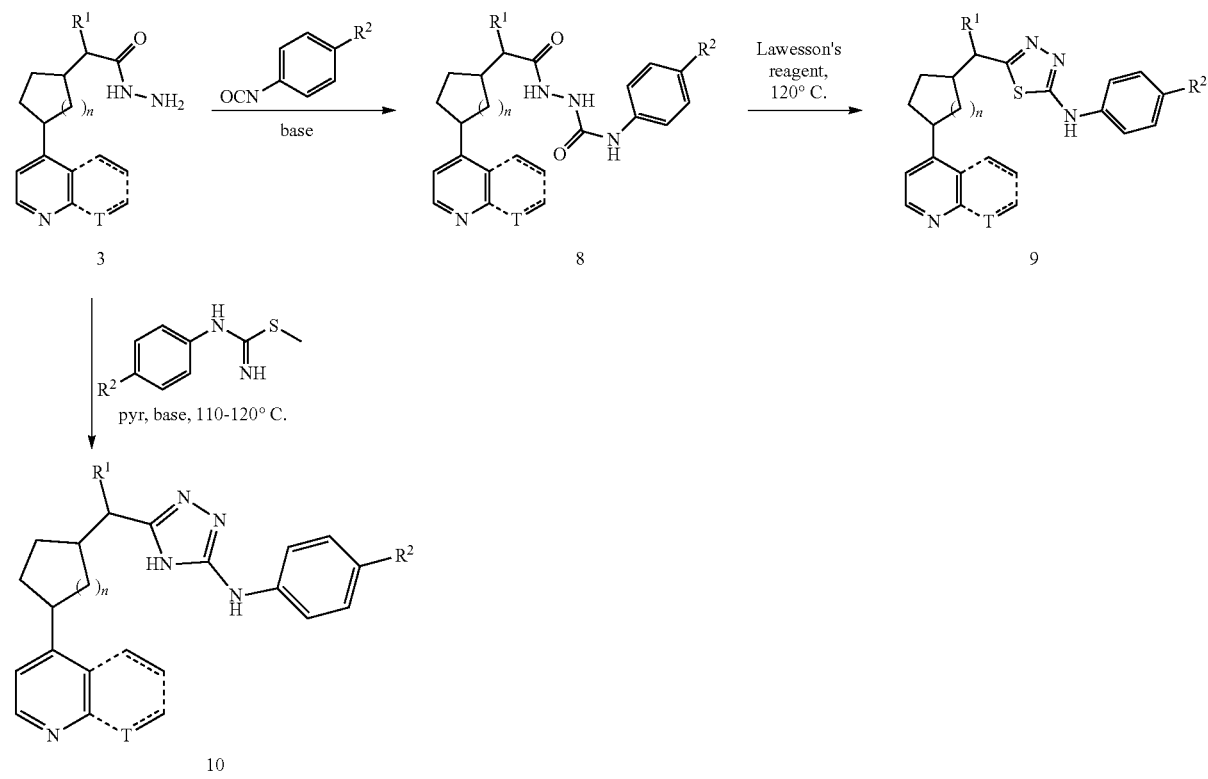

The synthesis of 4-aminothiadiazole 9 was achieved by a two-step synthesis. Reaction of hydrazide 3 with a substituted isocyanate yielded intermediate 8. Finally, treatment with Lawesson's reagent afforded aminothiaziazole 9.

Alternatively, if the 4-aminotriazole was desired, this was synthesized directly from hydrazide 3 by condensation with a substituted carbamimidothioate at elevated temperatures.

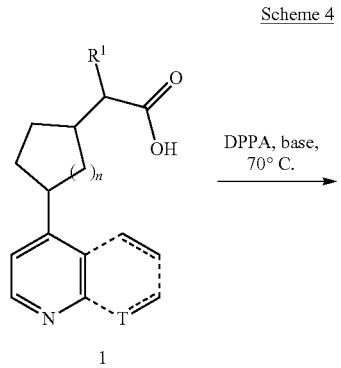

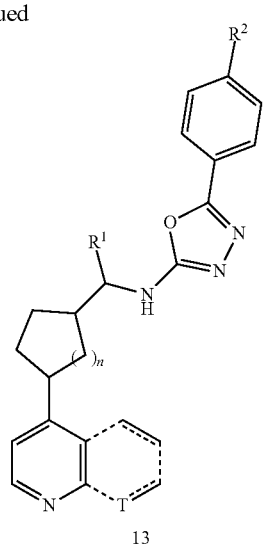

2-Aminooxadiazole 13 was generated by a 2-step procedure. Starting from acid 1, treatment with diphenyphosphorylazide and base at 70° C. yielded isocyanate 11, which was further reacted with a substituted carbazate to furnish intermediate 12. Cyclization with POCl₃ under high temperatures gave 2-aminooxadiazole 13.

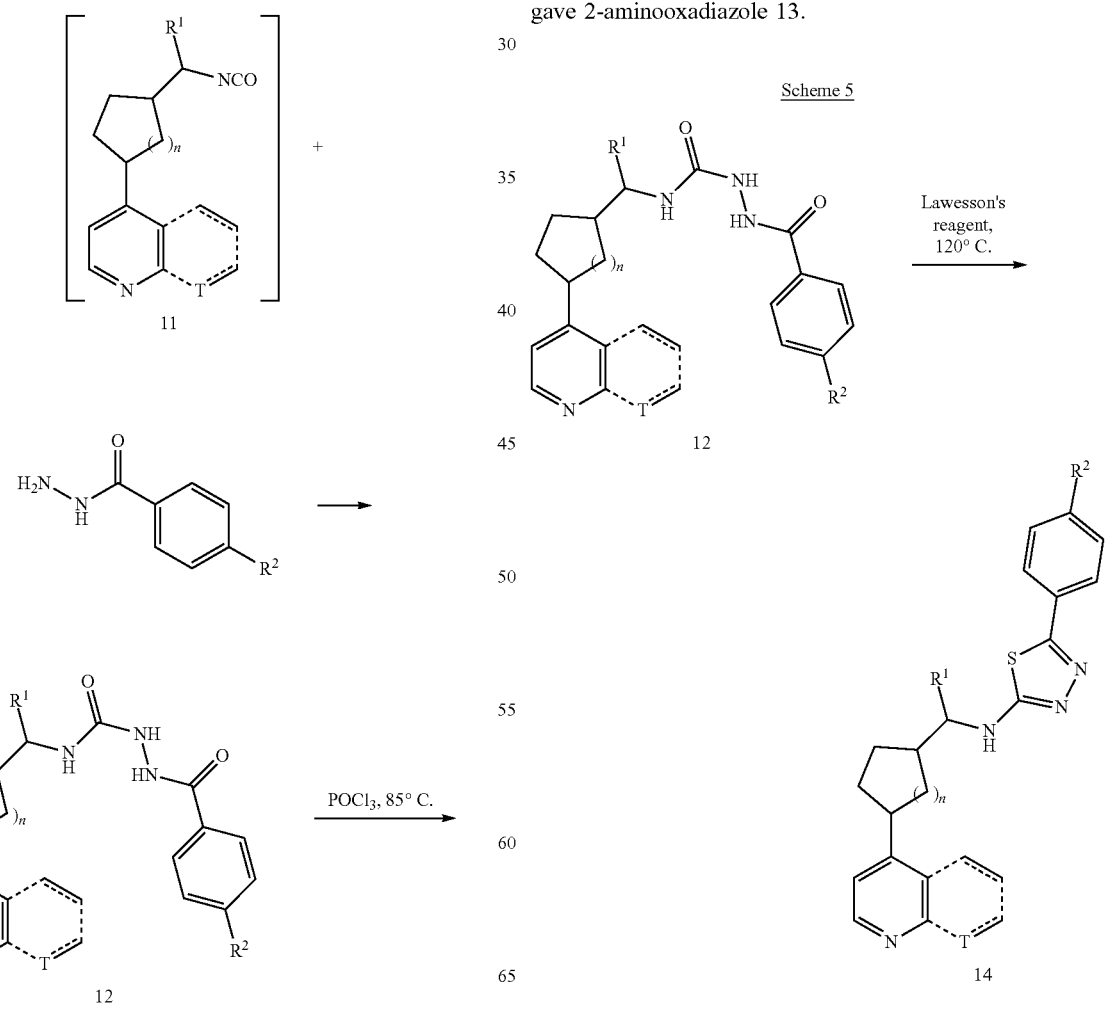

The synthesis of 2-aminothiadiazole 14 was accomplished by treating intermediate 12 with Lawesson's reagent at high temperatures.

Scheme 6

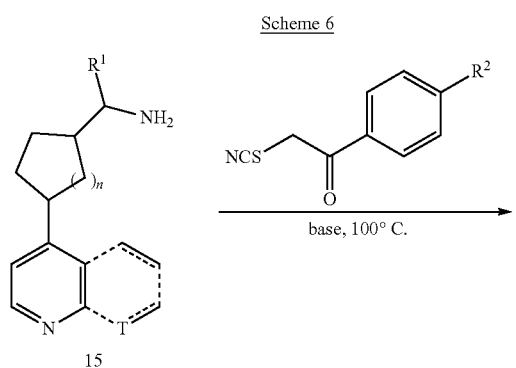

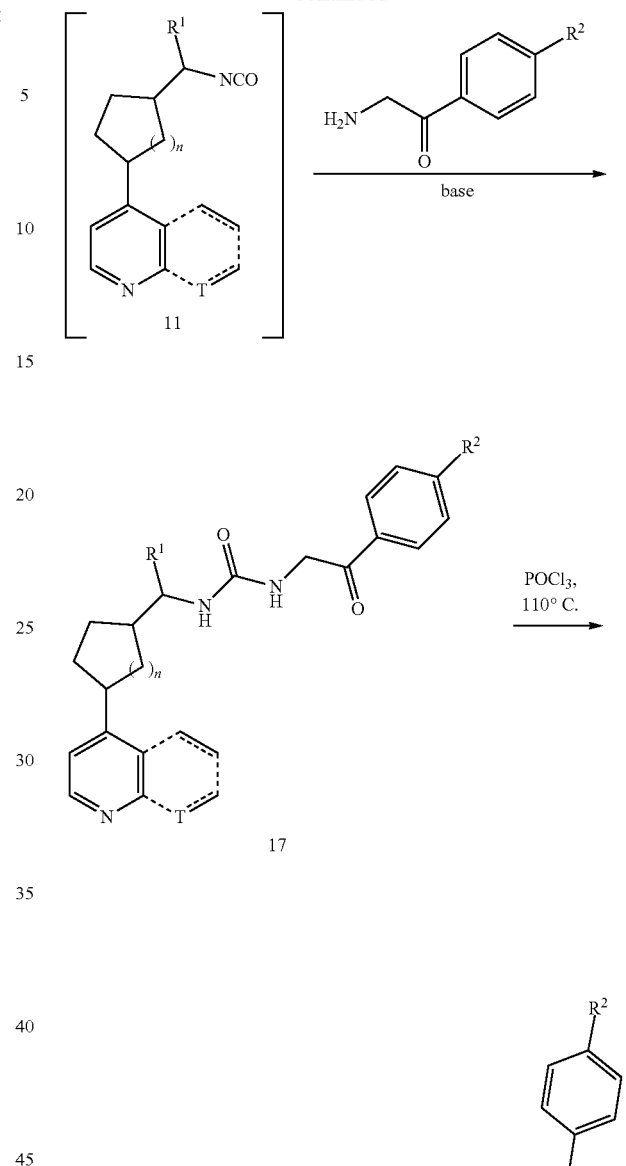

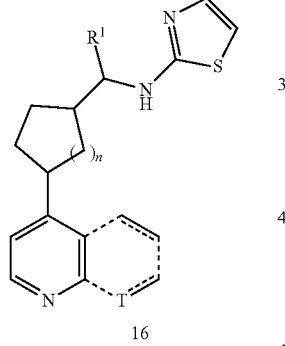

2-Aminothiazole 16 was synthesized in one step from amine 15 by condensation with a substituted thiocyanatoethanone.

Scheme 7

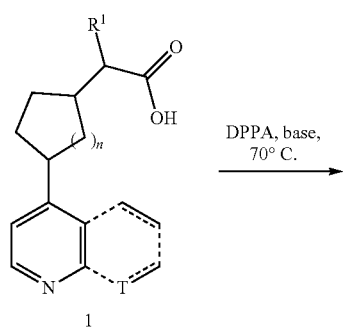

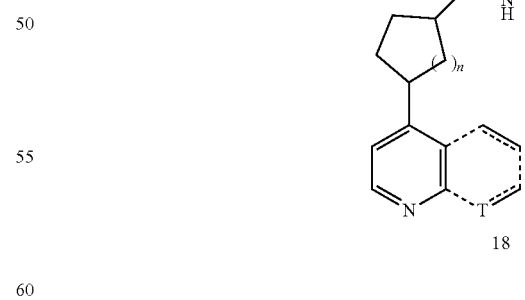

The synthesis of 2-aminooxazole was achieved in three steps. Beginning with acid 1, reaction with diphenylphosphorylazide gave isocyanate 11. This intermediate was further reacted with a 2-amino-(substituted phenyl)ethanone to afford urea 17. Cyclization to 2-aminooxazole occurred upon treatment of 17 with POCl₃ at high temperatures.

Scheme 8

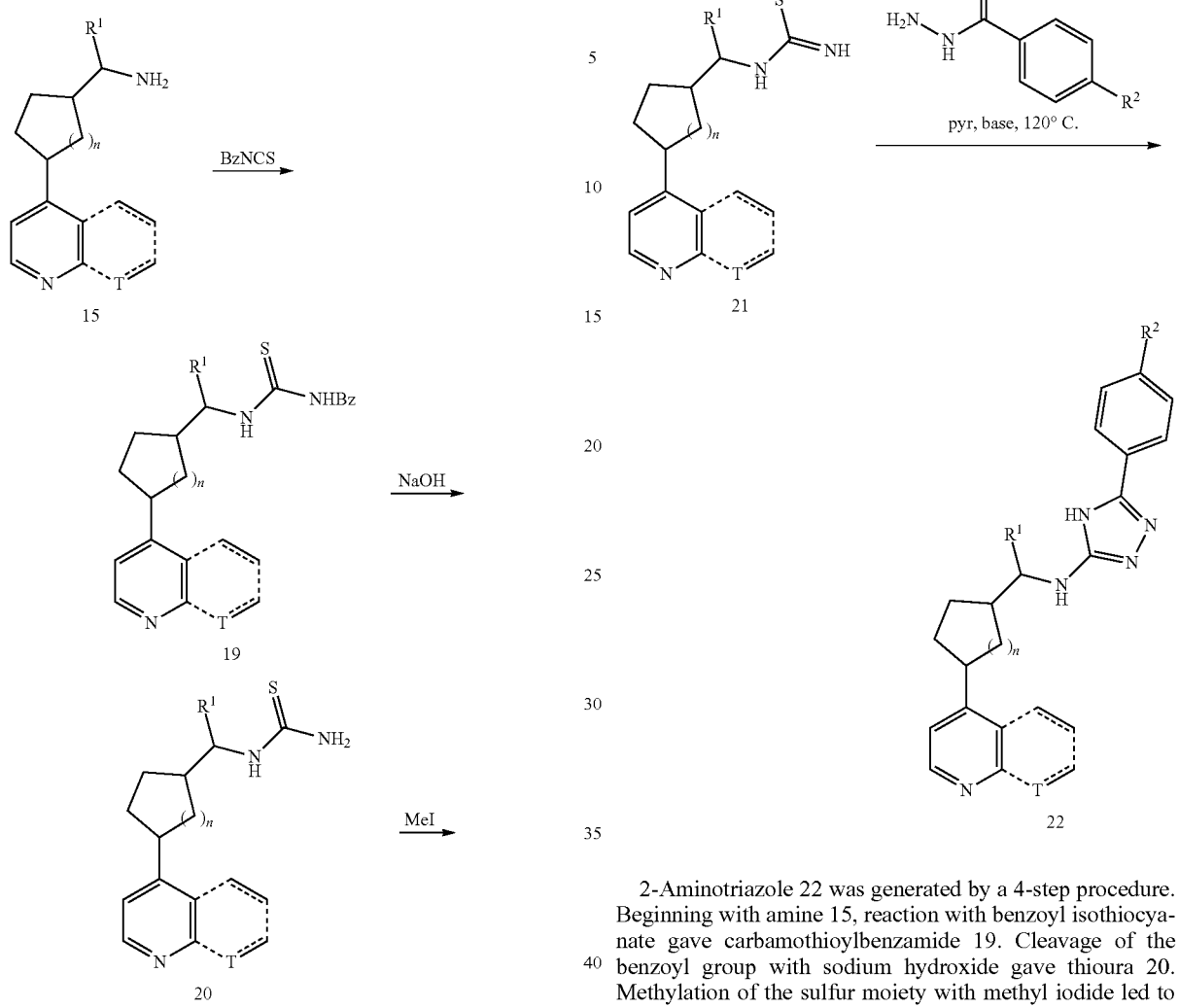

2-Aminotriazole 22 was generated by a 4-step procedure. Beginning with amine 15, reaction with benzoyl isothiocyanate gave carbamothioylbenzamide 19. Cleavage of the benzoyl group with sodium hydroxide gave thioura 20. Methylation of the sulfur moiety with methyl iodide led to carbamimidothioate 21. Finally, condensation with a substituted carbazate furnished 2-aminotriazole 22.

Scheme 9

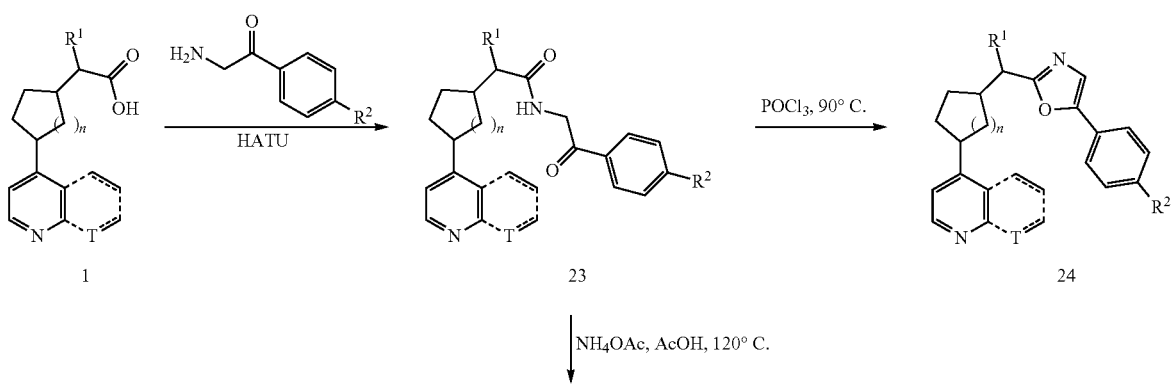

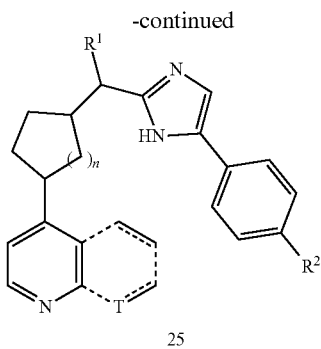

The synthesis of oxazole 24 or imidazole 25 was accomplished in two steps from acid 1. A HATU coupling with a substituted 2-aminoethanone afforded amide 23. Cyclization of this intermediate with POCl$_3$ gave oxazole 24, whereas treatment of intermediate 23 with ammonium acetate in the presence of acetic acid at 120° C. in a high boiling solvent gave imidazole 25.

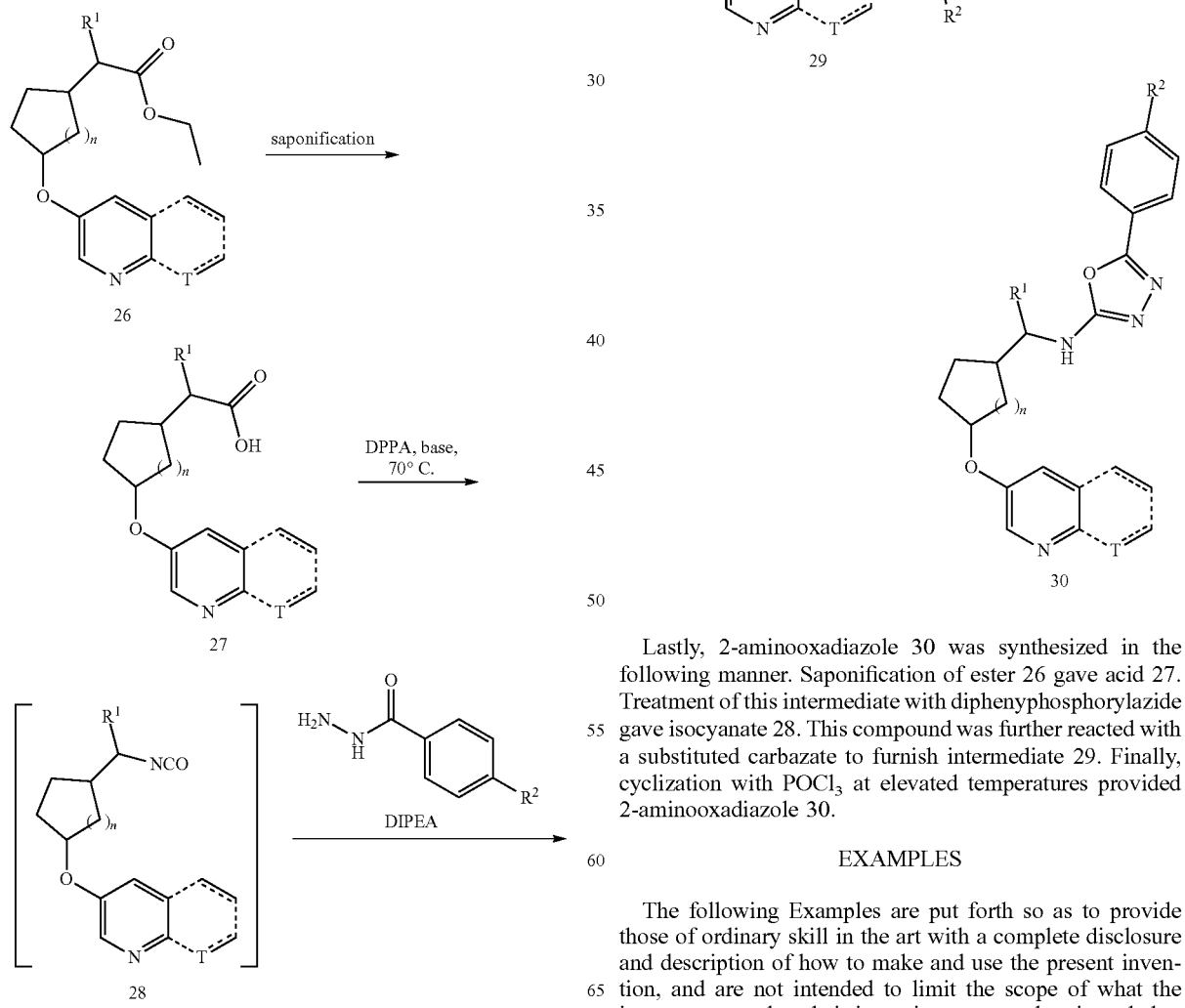

Lastly, 2-aminooxadiazole 30 was synthesized in the following manner. Saponification of ester 26 gave acid 27. Treatment of this intermediate with diphenyphosphorylazide gave isocyanate 28. This compound was further reacted with a substituted carbazate to furnish intermediate 29. Finally, cyclization with POCl$_3$ at elevated temperatures provided 2-aminooxadiazole 30.

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s): aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar: M=molar; kDa=kilodalton; i.m.=intramuscular(ly): i.p.=intraperitoneal(ly); SC or SQ=subcutaneous(ly); QD=daily: BID=twice daily; QW=weekly; QM=monthly; HPLC=high performance liquid chromatography; BW=body weight; U=unit; ns=not statistically significant; PBS=phosphate-buffered saline: IHC=immunohistochemistry; DMEM=Dulbecco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan et al., *Current Protocols in Protein Science*, Vols. 1-2, John Wiley and Sons, Inc., NY (2000)).

Software packages and databases for determining, e.g., antigenic fragments, leader sequences, protein folding, functional domains, glycosylation sites, and sequence alignments, are available (see, e.g., GCG® Wisconsin Package (Accelrys, Inc., San Diego, Calif.): and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 μL PBS containing a protease inhibitor cocktail (Set 2; Calbiochem, EMD Biosciences, San Diego, Calif.). The sonicate can be centrifuged for 10 min at 10,000×g, and the supernatant can be assayed in triplicate by incubating a 40 μl sample with an equal volume of 100 mmol/L potassium phosphate buffer, pH 6.5, containing 40 mmol/L ascorbic acid (neutralized to pH 7.0), 100 μmol/L methylene blue, 200 μg/mL catalase, and 400 μmol/l L-Trp for 30 min at 37° C. The assay can be terminated by the addition of 16 μL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 μg/mL; 500-2,000 units/mL) and 1-α-methyl Trp (1-MT; 40 μmol/L) can be added to the incubation media as indicated. This assay can also form the basis of a cell-based assay, and may be quantified via LCMS/MS as an alternative to UV/Vis detection.

Western Blot Analyses. Groups of 1,000-1,200 islets incubated for 24 h in Miami medium in the presence of cytokines can be harvested and sonicated in PBS as above, and 50 μg protein samples can be electrophoresed on 10% SDS-PAGE gels. COS7 cells (0.6-$10^6$ cells/60 mm3 petri dish) transfected with human-IDO plasmid (3 μg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-$STAT_{1\alpha}$ p91, and $STAT_{1\alpha}$ p91 (1:500; Zymed, San Francisco, Calif.). Immunoreactive proteins can be visualized with ECL PLUS® Western blotting detection reagent (Amersham BioSciences, Buckinghamshire. U.K.) after incubation for 1 h with anti-mouse horseradish peroxidase-conjugated secondary antibody (Jackson Immunolabs, West Grove, Pa.).

Immunohistochemical Detection of IDO. Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 μm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA TIER monochromatic CCD camera.

Alternative means for evaluating the IDO inhibitors of the present invention are described in WO 2010/0233166 and are summarized hereafter.

Biochemical Assay. cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif.*, 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-based Assay. COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^4$ cells per well. The following day, the wells can be washed and new media (phenol red free) containing 20 µg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Pharmacodynamic and Pharmacokinetic Evaluation. A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 µL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

Analytical HPLC/MS was performed using the following methods:

Method A: Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.): Flow rate: 0.8 ml/min: Mobile phase A: 100% Water, 0.05% TFA; Mobile phase B: 100% Acetonitrile, 0.05% TFA.

Method B: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.: Gradient: 0-100% B over 3 minutes, then a 0.75-minute hold at 100% B; Flow: 1.00 mL/min: Detection: UV at 220 nm.

Method C: Preparative Chromatographic Conditions: Instrument: Berger Prep SFC MGII (LVL-L4021 Lab): Column: Chiral IC 25×3 cm ID, 5 µm; Flow rate: 85.0 mL/min: Mobile Phase: 74/26 $CO_2$/MeOH; Detector Wavelength: 220 nm.

Method D: Preparative Chromatographic Conditions: Instrument: Berger Prep SFC MGII (LVL-L4021 Lab): Column: Chiral Phenomenex Cellulose-4 25×3 cm ID, 5 µm; Flow rate: 85.0 mL/min; Mobile Phase: 70/30 $CO_2$/MeOH: Detector Wavelength: 220 nm.

Method E: Preparative Chromatographic Conditions: Instrument: Berger Prep SFC MGII (LVL-L4021 Lab): Column: Chiral Phenomenex Cellulose-4 25×3 cm ID, 5 µm; Flow rate: 85.0 mL/min: Mobile Phase: 70/30 $CO_2$/MeOH w/0.1% DEA; Detector Wavelength: 220 nm.

Method F: Preparative Chromatographic Conditions: Instrument: Berger Prep SFC MGII (LVL-L4021 Lab): Column: Chiral IC-4 25×3 cm ID, 5 µm: Flow rate: 85.0 mL/min; Mobile Phase: 80/20 $CO_2$/MeOH: Detector Wavelength: 220 nm.

Method G: Preparative Chromatographic Conditions: Instrument: Berger Prep SFC MGII (LVL-L4021 Lab); Column: Chiral IC-4 250×4.6 mm ID, 5 µm; Flow rate: 2.0 mL/min; Mobile Phase: 80/20 $CO_2$/MeOH: Detector Wavelength: 220 nm.

Method H: Preparative Chromatographic Conditions: Instrument: Berger Prep SFC MGII (LVL-L4021 Lab); Column: Lux-Cellulose-4 250×4.6 mm ID, 5 µm; Flow rate: 2.0 mL/min; Mobile Phase: 80/20 $CO_2$/MeOH; Detector Wavelength: 220 nm.

Method I: Preparative Chromatographic Conditions: Instrument: Berger Prep SFC MGII Column: Chiral OJ 25×3 cm ID, 5 µm; Flow rate: 85.0 mL/min; Mobile Phase: 80/20 $CO_2$/IPA w/0.1% DEA; Detector Wavelength: 220 nm.

Method J: Preparative Chromatographic Conditions: Instrument: Berger Prep SFC MGII; Column: Chiral AD 25×3 cm ID, 5 µm; Flow rate: 85.0 mL/min; Mobile Phase: 65/35 $CO_2$/IPA w/0.1% DEA; Detector Wavelength: 220 nm.

Method K: Preparative Chromatographic Conditions: Instrument: Berger Prep SFC MGII. Column; Chiral AS-4 25×3 cm ID, 5 µm; Flow rate: 85.0 mL/min; Mobile Phase: 90/10 $CO_2$/MeOH w/0.1% DEA; Detector Wavelength: 220 nm.

Method L: Preparative Chromatographic Conditions: Instrument: Berger Prep SFC MGII; Column: Chiral OJ 25×3 cm ID, 5 μm; Flow rate: 85.0 mL/min; Mobile Phase: 80/20 CO$_2$/MeOH w/0.1% DEA; Detector Wavelength: 220 nm.

Method M: Preparative Chromatographic Conditions: Instrument: Berger Prep SFC MGII (LVL-L4021 Lab); Column: Chiral OD 25×3 cm ID, 5 μm; Flow rate: 80.0 mL/min; Mobile Phase: 85/15 CO$_2$/MeOH; Detector Wavelength: 220 nm.

Method N: Preparative Chromatographic Conditions: Instrument: Aurora SFC MGII (LVL-L4021 Lab); Column: Chiral OD 250×4.6 mm ID, 5 μm; Flow rate: 3.0 mL/min; Mobile Phase: 85/15 CO$_2$/MeOH; Detector Wavelength: 220 nm.

Preparation 1A

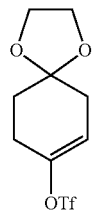

To a stirred solution of 1,4-dioxaspiro[4.5]decan-8-one (300 g, 1920.86 mmol, 1.0eq) and N-phenyltrifluoromethanesulfonimide (823.47 g, 2305.03 mmol, 1.2eq) in MTBE (7.5 L) under N2 at −78° C. was added 2.0 M NaHMDS in THF (1152.2 mL, 2305.03 mmol, 1.2eq) over 70 minutes, and the mixture was stirred for an additional 60 minutes. The reaction mixture was warmed to room temperature and stirred overnight until TLC showed complete consumption of the starting material. The mixture was quenched with aqueous KHSO$_4$ (100 ml), filtrated to remove the solid and concentrated the filtrate completely. To the residue was added 3 L MTBE, then washed with 5% NaOH (1.5 L×3). The organic phase was concentrated to obtain 567 g crude Preparation 1A (light yellow oil, yield 102%). The crude can be used directly in next step without further purification.

Preparation 1A: $^1$H NMR (400 MHz, CDCl$_3$): δ (ppm) 5.65 (t, J=4.0 Hz, 1H), 3.98 (d, J=1.5 Hz, 4H), 2.53 (s, 2H), 2.40 (s, 2H), 1.90 (t, J=6.6 Hz, 2H)

Preparation 1B

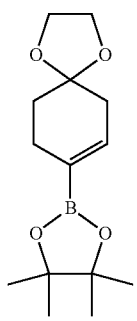

A mixture of crude Preparation 1A (600 g, 2.08 mol, 1eq), B$_2$Pin$_2$ (687.1 g, 2.71 mol, 1.3eq), KOAc (613 g, 6.24 mol, 3eq), NaBr (86 g, 0.833 mol, 0.4 eq) and Pd(dppf)Cl$_2$ (76 g, 0.1 mol, 0.05eq) in dioxane (6.5 L) was heated to reflux overnight. Once the reaction was complete, the mixture was concentrated and purified by FCC (2% 410% 420% EtOAc/PE) to give Preparation 1B (369 g, 66%).

Preparation 1B: LC-MS: 267.1 (M+1)+, $^1$H NMR (400 MHz, CDCl$_3$) δ 6.46 (s, 1H), 3.98 (s, 4H), 2.37-2.35 (m, 4H), 1.74-1.60 (t, 2H), 1.24 (s, 12H).

Preparation 1C

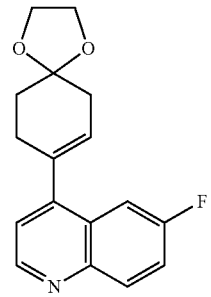

A mixture of Preparation 1B (368 g, 1.38 mol, 1.3eq), 4-chloro-6-fluoroquinoline (195 g, 1.07 mol, 1eq), K$_2$CO$_3$ (445 g, 3.22 mol, 3eq) and Pd(PPh$_3$)$_4$ (25 g, 22 mmol, 0.02eq) in dioxane-water (3 L, 4:1) was heated to reflux overnight. The solution was then concentrated and extracted with EtOAc. Purification by FCC (38% EtOAc/petrolium ether) gave Preparation 1C (236 g, 77%).

Preparation 1C: LC-MS: 286.1 (M+1)+, $^1$H NMR (400 MHz, CDCl$_3$) δ 8.80-8.29 (d, 1H), 8.11-8.07 (q, 1H), 7.63-7.61 (q, 1H), 7.47-7.46 (q, 1H), 7.26-7.22 (m, 1H), 5.75-5.74 (m, 1H), 4.08-4.05 (m, 4H), 2.63-2.59 (m, 2H), 2.59-2.53 (m, 2H), 2.0-1.97 (m, 2H).

Preparation 1D

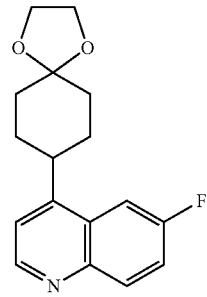

To Preparation 1C (125 g, 0.44 mol) in IPA (2 L) at 55° C. was added 10% Pd/C and the mixture was stirred under an atmosphere of H$_2$ overnight. The mixture was filtered and concentrated to give crude Preparation lD (130 g), which was used directly in the next step.

Preparation 1E

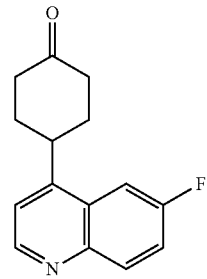

Preparation 1D (100 g, 0.348 mol) was treated with 4 N HCl (300 mL) in acetone (1200 mL) at 45° C. overnight. The mixture was monitored by TLC. Then the solution was then concentrated in vacuo. The residue was adjusted to pH 9 with 6 N NaOH and the mixture was partitioned between ethyl acetate and water. The organic layer was washed with brine, dried over anhydrous Na$_2$SO$_4$, filtered and concentrated to give light yellow solid, which was then purified by silica gel column using hexanes and ethyl acetate (from 20 percent ethyl acetate to 70% ethyl acetate) to afford Preparation 1E as a white solid, (47 g+20 g mixture, yield >55%). Preparation 1E: LC-MS: 244.0 (M+1)+, $^1$H NMR (400 MHz, CDCl$_3$) δ 8.84 (d, J=4.6 Hz, 1H), 8.16 (dd, J=9.3, 5.7 Hz, 1H), 7.72 (dd, J=10.3, 2.8 Hz, 1H), 7.52 (ddd, J=9.2, 7.8, 2.7 Hz, 1H), 7.29 (d, J=4.6 Hz, 1H), 3.69 (ddd, J=12.1, 9.0, 3.3 Hz, 1H), 2.77-2.54 (m, 4H), 2.37 (ddd, J=13.4, 5.9, 3.0 Hz, 2H), 204 (qd, J=12.6, 5.3 Hz, 2H).

Preparation 1F

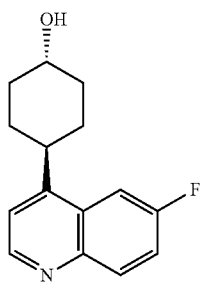

Intermediate 1E (57.8 g, 237.8 mmol) was dissolved in EtOH (240 mL) and cooled to 0° C. NaBH$_4$ (9.94 g, 261.6 mmol) was added portionwise maintaining the temperature within a range of 0-10° C. (exothermic reaction). The resulting suspension was stirred for 20 minutes. An LC/MS of an aliquot of the reaction mixture indicated consumption of ketone (m/z (M+H)−=244). The reaction was quenched at 0° C. by the slow addition of acetone (58 mL) over 15 minutes (exotherm). The reaction was poured slowly onto 500 mL of saturated aqueous ammonium chloride and 500 g of ice. The resulting aqueous solution was extracted with EtOAc (3×300 mL) and the combined organic fractions were washed with saturated aqueous ammonium chloride (250 mL) and saturated aqueous sodium chloride (250 mL). The organic portion was dried over anhydrous sodium sulfate and concentrated under reduced pressure. Sufficient silica to adsorb the oil was added and diluted with 10% MeOH in CH$_2$Cl$_2$. A similar quantity of silica was used as a silica plug to purify the material. The silica plug was washed with 10% MeOH in CH$_2$Cl$_2$ until UV-active material no longer could be detected by TLC (7:3 EtOAc/Hexanes, R$_f$=0.4). The filtrate was concentrated then suspended in 500 mL of toluene and concentrated again. Crude Preparation 1F was isolated as a yellow solid (58.2 g) that was used in the subsequent step without further purification.

Preparation 1G

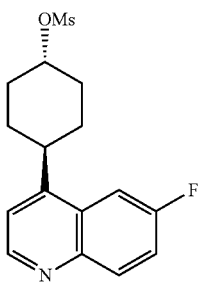

To Preparation 1F (58.2 g, 237.8 mmol) was added MeCN (125 mL) and pyridine (38.7 mL, 480 mmol) and the reaction mixture was cooled to 5° C. using an ice/water bath. Methanesulfonyl chloride (26.0 mL, 336 mmol) was added dropwise at 5° C. (exothermic reaction), the reaction mixture stirred for 1 hr at 5° C. and then brought up to room temperature and stirred for an additional 16 h during which time a white precipitate formed. The heterogeneous mixture was quenched by the addition of saturated aqueous ammonium chloride (200 mL) and extracted with CH$_2$Cl$_2$ (3×300 mL). The combined organic fractions were dried over anhydrous sodium sulfate and concentrated under reduced pressure. Excess pyridine was removed by azeotroping from toluene (3×300 mL). The crude material was recrystallized from H$_2$O/MeOH as follows: 1 mL/mmol of H$_2$O was added and the slurry was heated to 120° C. in an oil bath. MeOH was added until the solids went into solution (~0.5 L). After cooling white crystals were collected by filtration to give Preparation 1G (58.6 g, >20:1 dr, 76% over two steps). m/z (M+H)$_+$=324.1. H-NMR (400 MHz: CDCl$_3$): δ 8.82 (dd, J=4.6, 0.2 Hz, 1H), 8.15-8.11 (m, 1H), 7.64-7.61 (m, 1H), 7.52-7.46 (m, 1H), 7.25 (s, 1H), 4.78 (tt, J=10.9, 5.2 Hz, 1H), 3.24-3.16 (m, 1H), 3.07 (d, J=1.0 Hz, 3H), 2.42-2.38 (m, 2H), 2.16-2.12 (m, 2H), 1.93-1.66 (m, 4H).

Preparation 1H

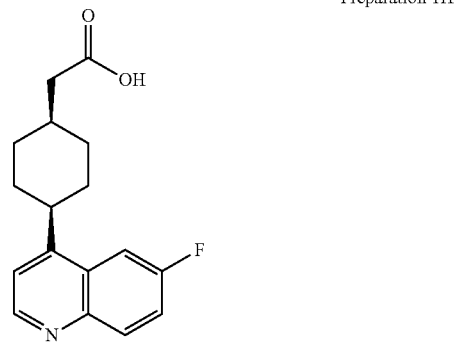

Di-tert-butyl malonate (33.5 mL, 150 mmol) was added dropwise to a stirred suspension of NaH (6.0 g, 60% suspension in oil, 150 mmol) in 1,2-dimethoxyethane (100 mL) under Ar, cooled in a water-ice bath. After stirring for 10 min, Preparation 1G (16.2 g, 50 mmol) was added and the reaction was heated at 85° C. for 20 h. After this time, acetic acid (100 mL) was added, the reaction flask was fitted with a distillation head and the temperature was raised to 130° C. 1,2-dimethoxyethane was distilled off under atmospheric pressure until the distillate was acidic (~100 mL). The distillation head was removed, a reflux condenser was attached, water (20 mL) was added and the reaction heated at 130° C. for 12 h. The reaction was concentrated under reduced pressure and poured onto 200 g of ice and 100 mL of saturated aqueous NaOAc. Preparation 1H was isolated as a white solid by filtration and further dried by refluxing with toluene in a Dean-Stark apparatus (11.0 g, 76%). m/z (M+H)$^+$=288.2. $^1$H-NMR (400 MHz; DMSO-d$_6$): δ 12.05 (bs, 1H), 8.79 (d, J=4.5 Hz, 1H), 8.06 (dd, J=9.2, 5.8 Hz, 1H), 7.94 (dd, J=11.0, 2.8 Hz, 1H), 7.66-7.61 (m, 1H), 7.50 (d, J=4.6 Hz, 1H), 2.41 (d, J=7.6 Hz, 2H), 2.28-2.23 (m, 1H), 1.87-1.78 (m, 2H), 1.73-1.64 (m, 6H).

Preparation 1I

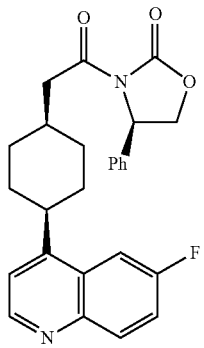

To a solution of Preparation 1H (1.4 g, 4.8 mmol) in THF (15 mL) was added NEt₃ (1.3 mL, 9.6 mmol). The reaction mixture was cooled to 0° C. and trimethylacetyl chloride (0.713 mL, 5.8 mmol) was added dropwise and the resulting solution stirred for 30 min at 0° C. In a separate flask, (R)-4-phenyloxazolidin-2-one (3, 1.01 g, 6.24 mmol) in THF (45 mL) at 0° C. was treated with 1 M LiHMDS solution in THF (dropwise addition of 6.24 mL, 6.24 mmol) and stirred at 0° C. The lithiate was added via cannula to the first flask. The reaction mixture was allowed to warm to rt and was stirred for 3 hours. LC/MS indicated the complete consumption of the starting carboxylic acid and formation of the desired imide. The reaction mixture was poured onto saturated aqueous ammonium chloride (50 mL) and the layers were separated. The aqueous layer was extracted with EtOAc (3×50 mL). The combined organic extracts were dried over anhydrous sodium sulfate and chromatographed on silica using EtOAc/Hexanes 0 to 100% gradient to give Preparation 1I as a white foam in 83% yield. m/z (M+H)⁺=433.3. ¹H-NMR (400 MHz; CDCl₃): δ 8.80 (d, J=4.5 Hz, 1H), 8.11 (dd, J=9.1, 5.7 Hz, 1H), 7.63 (dd, J=10.5, 2.5 Hz, 1H), 7.48-7.43 (m, 1H), 7.40-7.30 (m, 6H), 5.47-5.44 (m, 1H), 4.71 (t, J=8.9 Hz, 11H), 4.31-4.28 (m, 1H), 3.20-3.11 (m, 3H), 2.49-2.46 (m, 1H), 1.82-1.67 (m, 6H).

Preparation 1J

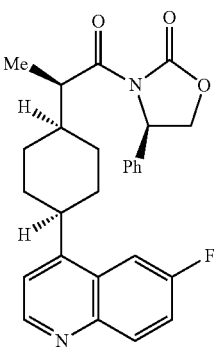

A solution of Preparation 1I (21.6 g, 50 mmol) in anhydrous THF (200 mL) was cooled to −40° C. (using acetonitrile/dry ice bath, some precipitation occurs) and 2 M NaHMDS solution in THF (30 mL, 60 mmol) was added over 5 min (a 5-8° C. rise in temperature was observed). The resulting yellow reaction mixture was stirred for 10 min, became homogeneous, and MeI (10.6 g, 75 mmol) was added dropwise over 2 min (a 10° C. rise in temperature was observed). The reaction mixture was stirred for 1 h at −40° C. and LC/MS indicated the complete consumption of the starting material and formation of the desired methyl imide. The reaction mixture was rapidly diluted with saturated aqueous ammonium chloride solution (400 mL) and the biphasic mixture was stirred for 15 min. ⁱPrOAc (100 mL) was added, the layers were separated, and the aqueous layer was extracted with ⁱPrOAc (3×50 mL). The combined organic extracts were dried over anhydrous magnesium sulfate filtered, and concentrated. The resulting residue was recrystallized by dissolving in 400 mL hot acetone and adding H₂O until a milky solution formed followed to re-dissolving with heating (~3:1 acetone/H₂O). Preparation 1J was obtained as white needles (15.04 g, 2 crops, 68%). m/z (M+H)⁺=447.3. ¹H-NMR (400 MHz: CDCl₃): δ 8.81 (d, J=4.6 Hz, 1H), 8.10 (dd, J=9.2, 5.7 Hz, 1H), 7.65 (dd, J=10.6, 2.7 Hz, 1H), 7.47-7.42 (m, 1H), 7.41-7.29 (m, 6H), 5.47 (dd, J=8.8, 3.8 Hz, 1H), 4.69 (t, J=8.9 Hz, 1H), 4.38-4.30 (m, 1H), 4.26 (dd, J=8.9, 3.9 Hz, 1H), 3.26-3.21 (m, 1H), 2.18-2.15 (m, 1H), 1.93-1.64 (m, 8H), 1.09 (d, J=6.9 Hz, 3H).

Preparation 1K

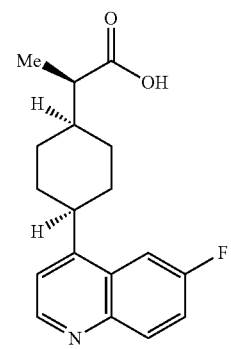

To a solution of Preparation 1J (82.0 g, 183.6 mmol) in THF (610 mL) at 0° C. was added aqueous H₂O₂ (35 wt %, 82 mL) and LiOH (7.04 g, 293.8 mmol) in H₂O (189 mL). The resulting reaction mixture was allowed to slowly warm to rt and stirred overnight. The reaction was cooled to 0° C. and saturated aqueous sodium bisulfite solution (250 mL) was added. After stirring for 30 min, the THF was removed under reduced pressure. Acetic acid (34 mL) was added followed by EtOAc (300 mL). The layers were separated, and the aqueous layer was extracted with EtOAc (3×500 mL). The combined organic extracts were dried over anhydrous Na₂SO₄, filtered, and concentrated under reduced pressure. The brown crude reaction mixture was suspended in MeCN (400 mL) and the suspension was brought to reflux with vigorous stirring. After cooling to rt, the solids were collected by filtration washing with additional MeCN. Preparation 1K was obtained as a white solid (45.4 g, 82%). m/z (M+H)⁺=302.2. ¹H-NMR (400 MHz; DMSO-d6): δ 12.10 (s, 1H), 8.79 (d, J=4.5 Hz, 1H), 8.07 (dd, J=9.2, 5.9 Hz, 1H), 7.97-7.94 (m, 1H), 7.67-7.62 (m, 1H), 7.49 (d, J=4.5 Hz, 1H), 3.41-3.36 (m, 1H), 2.73-2.65 (m, 1H), 1.83-1.61 (m, 9H), 1.08 (d, J=6.8 Hz, 3H). Chiral HPLC, >99% ee (ChiralPak IC-3, 3 μM, 4.6×250 mm, 15 min isocratic 70% heptane 30% i-PrOH with 230 nm detection) at a flow rate of 0.75 mL/min the desired enantiomer had a retention time of 8.6 min with the undesired enantiomer eluting at 9.5 min.

1L. tert-Butyl 2-((R)-2-((1s,4S)-4-(6-fluoroquinolin-4-yl)cyclohexyl)propanoyl)hydrazinecarboxylate To a solution of (R)-2-((1s,4S)-4-(6-fluoroquinolin-4-yl)cyclohexyl)propanoic acid (1K)(100 mg, 0.332 mmol) in DMF (3 mL) was added HATU (145 mg, 0.382 mmol). The reaction mixture was stirred at it for 10 min, followed by addition of tert-butyl carbazate (0.047 mL, 0.365 mmol) and N-methyl morpholine (0.16 mL, 1.33 mmol). The resulting mixture was stirred at rt for 2 h. The reaction mixture was diluted with ethyl acetate and saturated NaHCO$_3$ solution. The organic layer was separated, washed with brine, and dried over MgSO$_4$. The filtrate was concentrated in vacuo to give Intermediate 1L (white solid, 130 mg, 0.313 mmol, 94% yield). LC-MS Anal. Calc'd for C$_{23}$H$_{30}$FN$_3$O$_3$ 415.23, found [M+H] 416.3 T$_r$=0.68 min (Method A). $^1$H NMR (400 MHz, chloroform-d) δ: 8.80 (d, J=4.6 Hz, 1H), 8.12 (dd, J=9.2, 5.7 Hz, 1H), 7.65 (dd, J=10.5, 2.8 Hz, 1H), 7.52-7.43 (m, 2H), 7.32 (d, J=4.6 Hz, 1H), 3.37-3.23 (m, 1H), 2.61-2.46 (m, 1H), 2.17-2.04 (m, 1H), 1.98-1.57 (m, 9H), 1.48 (s, 9H), 1.25 (d, J=6.8 Hz, 3H).

1M. (R)-2-((1s,4S)-4-(6-fluoroquinolin-4-yl)cyclohexyl)propanehydrazide

To a solution of Intermediate 1L (330 mg, 0.794 mmol) in CH$_2$Cl$_2$ (5 mL) was added HCl solution (4.0 M solution in dioxane) (3.97 mL, 15.88 mmol). The reaction mixture was stirred at rt for 2 h. White solid precipitated out after 30 min. The reaction mixture was concentrated in vacuo to afford Intermediate 1M as 2HCl salt (white solid, 310 mg, 0.758 mmol, 95% yield). LC-MS Anal. Calc'd for C$_{18}$H$_{22}$FN$_3$O.2 HCl, 315.17 found [M+H] 316.1 T$_r$=0.55 min (Method A). $^1$H NMR (400 MHz, MeOH-d$_4$) δ:9.13 (d, J=5.7 Hz, 1H), 8.36 (d, J=2.4 Hz, 1H), 8.34-8.32 (m, 1H), 8.31 (d, J=4.8 Hz, 11H), 8.19 (d, J=5.7 Hz, 1H), 8.03 (ddd, J=9.3, 7.9, 2.6 Hz, 1H), 3.78-3.68 (m, 1H), 2.96-2.84 (m, 1H), 2.18-1.70 (m, 9H), 1.25 (d, J=6.8 Hz, 3H)

Example 1 4-((1s,4s)-4-((R)-1-(5-(4-Chlorophenyl)-4H-1,2,4-triazol-3-yl)ethyl)cyclohexyl)-6-fluoroquinoline The reaction mixture of Intermediate 1M (17.71 mg, 0.093 mmol), and 4-chlorobenzimidamide hydrochloride (17.7 mg, 0.093 mmol) in pyridine (1 mL) and TEA (0.065 mL, 0.464 mmol) in a sealed tube was purged with nitrogen stream for 1 min, then sealed and heated at 110° C. over night. The reaction mixture was cooled down and diluted with ethyl acetate and saturated NH$_4$Cl solution. The organic layer was separated and concentrated in vacuo. The residue was dissolved in MeOH, purified by preparative HPLC. Fractions containing the desired product were combined, dried via centrifugal evaporation to give Example 1 (10.8 mg, 0.024 mmol, 31% yield). LC-MS Anal. Calc'd for C$_{25}$H$_{24}$ClFN$_4$ 434.17, found [M+H]435.3. T$_r$=1.58 min (Method B). $^1$H NMR (500 MHz, DMSO-d$_6$)δ: 8.80 (d, J=4.1 Hz, 1H), 8.07 (dd, J=8.9, 6.0 Hz, 1H), 7.97 (d, J=8.0 Hz, 2H), 7.93 (d, J=10.6 Hz, 1H), 7.64 (t, J=8.5 Hz, 1H), 7.55 (d, J=4.1 Hz, 1H), 7.48 (d, J=7.4 Hz, 2H), 3.76 (d, J=4.2 Hz, 2H), 2.13-1.93 (m, 2H), 1.89-1.47 (m, 6H), 1.28 (d, J=6.1 Hz, 3H), 1.15 (br. s., 1H)

Example 2

2-(4-Fluorophenyl)-5-((R)-1-((1s,4s)-4-(6-fluoroquinolin-4-yl)cyclohexyl)ethyl)-1,3,4-oxadiazole

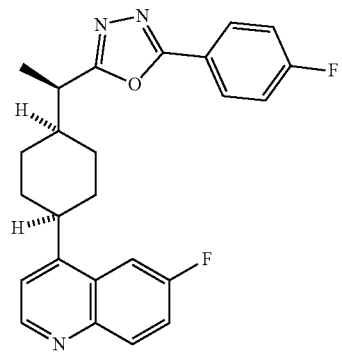 [SMILES: C[C@@H](c1nnc(-c2ccc(F)cc2)o1)[C@H]1CC[C@@H](c2ccnc3ccc(F)cc32)CC1]

The reaction mixture of 4-fluorobenzimidamide hydrochloride (17.6 mg, 0.100 mmol), and (R)-2-((1s,4S)-4-(6-fluoroquinolin-4-yl)cyclohexyl)propanehydrazide 2HCl salt (30 mg, 0.077 mmol) in pyridine (1 mL) and TEA (0.065 mL, 0.464 mmol) in a sealed tube was purged with nitrogen and then heated at 120° C. over night. The reaction mixture was cooled down and diluted with ethyl acetate and NH$_4$Cl solution. The organic layer was separated and concentrated in vacuo. The residue was dissolved in MeOH, purified by preparative HPLC/MS to give Example 2 (6.5 mg, 0.015 mmol, 20% yield). LC-MS Anal. Calc'd for C$_{25}$H$_{23}$F$_2$N$_3$O, 419.18 found [M+H] 420.3 T$_r$=1.67 min (Method B). $^1$H NMR (500 MHz, DMSO-d$_6$) δ: 8.78 (d, J=4.4 Hz, 1H), 8.15-8.00 (m, 3H), 7.93 (d, J=10.8 Hz, 1H), 7.64 (t, J=8.6 Hz, 1H), 7.57 (d, J=4.2 Hz, 1H), 7.40 (t, J=8.6 Hz, 2H), 3.84-3.79 (m, 1H), 3.64-3.51 (m, 1H), 2.13-1.92 (m, 2H), 1.90-1.57 (m, 6H), 1.35 (d, J=6.7 Hz, 3H), 1.29 (br. s., 1H).

Example 3

6-Fluoro-4-((1s,4s)-4-((R)-1-(5-(4-fluorophenyl)-4H-1,2,4-triazol-3-yl)ethyl)cyclohexyl)quinoline

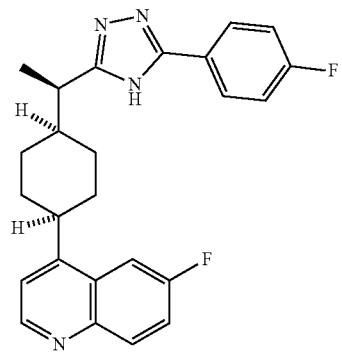 [SMILES: C[C@@H](c1nnc(-c2ccc(F)cc2)[nH]1)[C@H]1CC[C@@H](c2ccnc3ccc(F)cc32)CC1]

The reaction mixture of 4-fluorobenzimidamide hydrochloride (17.6 mg, 0.100 mmol), and (R)-2-((1s,4S)-4-(6-fluoroquinolin-4-yl)cyclohexyl)propanehydrazide.2HCl salt (30 mg, 0.077 mmol) in pyridine (1 mL) and TEA (0.065 mL, 0.464 mmol) in a sealed tube was purged with nitrogen and then heated at 120° C. over night. The reaction mixture was cooled down and diluted with ethyl acetate and NH$_4$Cl solution. The organic layer was separated and concentrated in vacuo. The residue was dissolved in MeOH, purified by preparative HPLC/MS to give Example 2 (above) and Example 3 (17 mg, 0.040 mmol, 52% yield). LC-MS Anal. Calc'd for C$_{25}$H$_{24}$F$_2$N$_4$, 418.48, found [M+H] 419.3. T$_r$=1.39 min (Method B). $^1$H NMR (500 MHz, DMSO-d$_6$) δ: 8.81 (d, J=4.1 Hz, 1H), 8.07 (dd, J=8.9, 5.9 Hz, 1H), 8.00 (t, J=6.4 Hz, 2H), 7.93 (d, J=10.5 Hz, 1H), 7.64 (t, J=8.5 Hz, 1H), 7.56 (d, J=4.0 Hz, 1H), 7.25 (br. s., 2H), 3.78-3.65 (m, 2H), 2.12-1.93 (m, 2H), 1.89-1.47 (m, 6H), 1.28 (d, J=6.1 Hz, 3H), 1.16 (br. s., 1H)

Example 4

2-(4-Chlorophenyl)-5-((R)-1-((1s,4s)-4-(6-fluoroquinolin-4-yl)cyclohexyl)ethyl)-1,3,4-oxadiazole

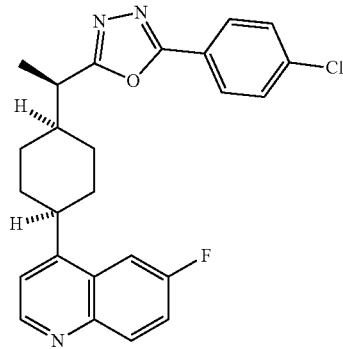 [SMILES: C[C@@H](c1nnc(-c2ccc(Cl)cc2)o1)[C@H]1CC[C@@H](c2ccnc3ccc(F)cc32)CC1]

4A. 4-chloro-N'—((R)-2-((1s,4S)-4-(6-fluoroquinolin-4-yl)cyclohexyl)propanoyl)benzohydrazide To a solution of 4-chlorobenzoic acid (14.5 mg, 0.093 mmol) in DMF (1 mL) was added HATU (39 mg, 0.10 mmol) and the reaction mixture was stirred at rt for 10 min, followed by addition of Intermediate 1B (R)-2-((1s,4S)-4-(6-fluoroquinolin-4-yl)cyclohexyl)propanehydrazide, 2 HCl (30 mg, 0.077 mmol) and 4-methylmorpholine (0.051 mL, 0.46 mmol). The resulting mixture was stirred at rt for 3 h. The reaction mixture was diluted with ethyl acetate and saturated NaHCO$_3$ solution. The organic layer was separated and washed with brine, and dried over MgSO$_4$. The filtrate was concentrated in vacuo. The residue was purified by silica gel flash chromatography to give intermediate 4A (white solid, 29 mg, 0.064 mmol, 83% yield). LC-MS Anal. Calc'd for C$_{25}$H$_{25}$ClFN$_3$O$_2$ 453.16, found [M+H] 454.3 T$_r$=0.71 min (Method A). $^1$H NMR (400 MHz, chloroform-d) δ: 10.31 (br. s., 1H), 9.97 (s, 1H), 8.69 (d, J=4.6 Hz, 1H), 8.11 (dd, J=9.2, 5.7 Hz, 1H), 7.74 (d, J=8.6 Hz, 2H), 7.59 (dd, J=10.5, 2.5 Hz, 1H), 7.45 (ddd, J=9.1, 7.9, 2.6 Hz, 1H), 7.34-7.25 (m, 2H), 7.18 (d, J=4.6 Hz, 1H), 3.19 (t, J=10.2 Hz, 1H), 2.86-2.75 (m, 1H), 2.15-2.01 (m, 1H), 1.95-1.64 (m, 7H), 1.61-1.47 (m, 1H), 1.21 (d, J=6.6 Hz, 3H)

Example 4 2-(4-Chlorophenyl)-5-((R)-1-((1s,4S)-4-(6-fluoroquinolin-4-yl)cyclohexyl)ethyl)-1,3,4-oxadiazole The reaction mixture of intermediate 4A 4-chloro-N'—((R)-2-((1s,4S)-4-(6-fluoroquinolin-4-yl)cyclohexyl)propanoyl)benzohydrazide (28 mg, 0.062 mmol) in POCl$_3$ (0.2 mL, 2.146 mmol) was heated at 90° C. over night. The reaction mixture was concentrated in vacuo and the residue was dissolved in MeOH, purified by preparative HPLC. Fractions containing the desired product were combined, dried via centrifugal evaporation to give Example 4 (15 mg, 0.034 mmol, 55.2% yield). LC-MS Anal. Calc'd for C$_{25}$H$_{23}$ClFN$_3$O, 435.15 found [M+H] 436.3 T$_r$=1.94 min (Method B). $^1$H NMR (500 MHz, DMSO-d$_6$) δ: 8.81 (d, J=4.4 Hz, 1H), 8.08 (dd, J=9.0, 5.8 Hz, 1H), 8.02-7.91 (m, 3H), 7.66 (d, J=8.3 Hz, 3H), 7.58 (d, J=4.4 Hz, 1H), 3.61 (s, 2H), 2.14-1.94 (m, 2H), 1.91-1.58 (m, 6H), 1.36 (d, J=6.8 Hz, 3H), 1.32 (br. s., 1H)

Example 5

2-(4-Chlorophenyl)-5-((R)-1-((1s,4S)-4-(6-fluoroquinolin-4-yl)cyclohexyl)ethyl)-1,3,4-thiadiazole

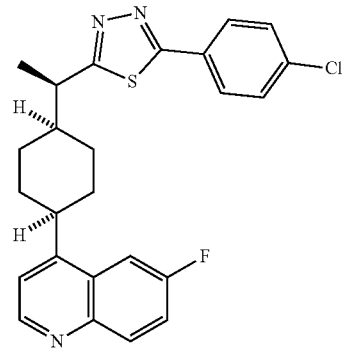 [SMILES: C[C@@H](c1nnc(-c2ccc(Cl)cc2)s1)[C@H]1CC[C@@H](c2ccnc3ccc(F)cc32)CC1]

Example 5 2-(4-chlorophenyl)-5-((R)-1-((1s,4S)-4-(6-fluoroquinolin-4-yl)cyclohexyl)ethyl)-1,3,4-thiadiazole The reaction mixture of 4-chloro-N'—((R)-2-((1s,4S)-4-(6-fluoroquinolin-4-yl)cyclohexyl)propanoyl)benzohydrazide (28 mg, 0.062 mmol) and lawesson's reagent (100 mg, 0.247 mmol) in toluene (4 mL) was heated at 120° C. for 1.5 h. The reaction mixture was cooled down and diluted with ethyl acetate and 1N NaOH solution. The organic layer was separated and concentrated in vacuo. The residue was dissolved in MeOH, purified by preparative HPLC. Fractions containing the desired product were combined, dried via centrifugal evaporation to give Example 5 (13.4 mg, 0.029 mmol, 47% yield). LC-MS Anal. Calc'd for C$_{25}$H$_{23}$ClFN$_3$S, 451.13 found [M+H] 452.3 T$_r$=1.97 min (Method B). $^1$H NMR (500 MHz, DMSO-d$_6$) δ: 8.83 (d, J=4.4 Hz, 1H), 8.08 (dd, J=9.0, 5.8 Hz, 1H), 7.97 (d, J=8.5 Hz, 3H), 7.65 (t, J=8.7 Hz, 1H), 7.61 (d, J=8.2 Hz, 3H), 3.86-3.78 (m, 1H), 3.61-3.50 (m, 1H), 2.12-1.97 (m, 2H), 1.92-1.76 (m, 3H), 1.72 (d, J=9.4 Hz, 2H), 1.61 (d, J=10.4 Hz, 1H), 1.39 (d, J=6.7 Hz, 3H), 1.34-1.36 (m, 1H)

Example 6

4-(5-((R)-1-((1s,4S)-4-(6-Fluoroquinolin-4-yl)cyclohexyl)ethyl)-1,3,4-thiadiazol-2-yl)benzonitrile

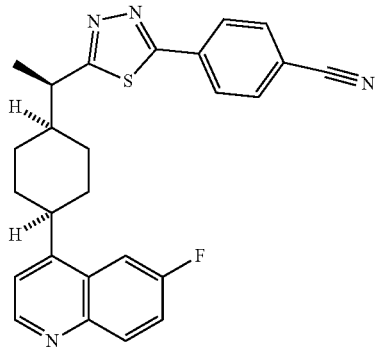 [SMILES: C[C@@H](c1nnc(-c2ccc(C#N)cc2)s1)[C@H]1CC[C@@H](c2ccnc3ccc(F)cc32)CC1]

6A. 4-cyano-N'—((R)-2-((1s,4S)-4-(6-fluoroquinolin-4-yl)cyclohexyl)propanoyl) benzohydrazide To a solution of 4-cyanobenzoic acid (16.79 mg, 0.114 mmol) in DMF (1 mL) was added HATU (47.0 mg, 0.124 mmol) and the reaction mixture was stirred at it for 10 min, followed by addition of (R)-2-((1s,4S)-4-(6-fluoroquinolin-4-yl)cyclohexyl)propanehydrazide (30 mg, 0.095 mmol) and 4-methylmorpholine (0.07 mL, 0.58 mmol). The resulting mixture was stirred at rt for 3 h. The reaction mixture was diluted with ethyl acetate and saturated NaHCO$_3$ solution. The organic layer was separated and washed with brine, dried over MgSO$_4$. The filtrate was concentrated in vacuo. The residue was dissolved in DCM and purified by silica gel flash chromatography, eluting with 0-60% ethyl acetate in DCM to give Intermediate 6A (white solid, 24 mg, 0.054 mmol, 57% yield). LC-MS Anal. Calc'd for $C_{26}H_{23}FN_4O_2$, 444.20 found [M+H] 445.2 T$_r$=0.68 min (Method A). $^1$H NMR (400 MHz, METHANOL-d$_4$) δ: 8.76 (d, J=4.8 Hz, 1H), 8.07 (dd, J=9.2, 5.7 Hz, 1H), 8.03-7.98 (m, 2H), 7.88 (dd, J=10.7, 2.8 Hz, 1H), 7.86-7.82 (m, 2H), 7.65-7.53 (m, 2H), 3.48-3.37 (m, 1H), 2.91-2.81 (m, 1H), 2.15-1.95 (m, 4H), 1.94-1.70 (m, 5H), 1.26 (d, J=6.8 Hz, 3H)

Example 6, 4-(5-((R)-1-((1s,4S)-4-(6-fluoroquinolin-4-yl)cyclohexyl)ethyl)-1,3,4-thiadiazol-2-yl)benzonitrile The reaction mixture of 4-cyano-N'—((R)-2-((1s,4S)-4-(6-fluoroquinolin-4-yl)cyclohexyl)propanoyl)benzohydrazide (24 mg, 0.054 mmol) and Lawesson's reagent (87 mg, 0.216 mmol) in toluene (4 mL) was heated at 120° C. for 1.5 h. The reaction mixture was cooled down and diluted with ethyl acetate and 1 N NaOH solution. The organic layer was separated and concentrated in vacuo and the residue was dissolved in MeOH, purified by preparative HPLC. Fractions containing the desired product were combined, dried via centrifugal evaporation to give Example 6 (12.9 mg, 0.029 mmol, 53.4% yield). LC-MS Anal. Calc'd for $C_{26}H_{23}FN_4S$ 442.16, found [M+H] 443.1 T$_r$=1.59 min (Method B). $^1$H NMR (500 MHz, DMSO-d$_6$) δ: 8.83 (d, J=4.4 Hz, 1H), 8.14 (d, J=8.2 Hz, 2H), 8.08 (dd, J=9.1, 5.9 Hz, 1H), 8.03-7.91 (m, 3H), 7.72-7.62 (m, 1H), 7.60 (d, J=4.5 Hz, 1H), 3.88 (dd, J=10.8, 6.6 Hz, 1H), 3.42 (br. s., 1H), 2.05 (br. s., 2H), 1.95-1.55 (m, 6H), 1.40 (d, J=6.7 Hz, 3H), 1.35 (d, J=13.0 Hz, 1H)

Example 7

N-(4-Fluorophenyl)-5-((R)-1-((1s,4S)-4-(6-fluoroquinolin-4-yl)cyclohexyl)ethyl)-1,3,4-thiadiazol-2-amine

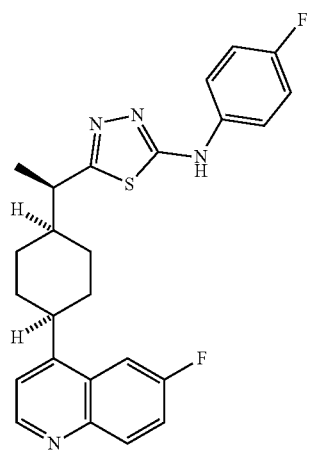 [SMILES: C[C@@H](c1nnc(Nc2ccc(F)cc2)s1)[C@H]1CC[C@@H](c2ccnc3ccc(F)cc32)CC1]

7A. N-(4-fluorophenyl)-2-((R)-2-((1s,4S)-4-(6-fluoroquinolin-4-yl)cyclohexyl)propanoyl)hydrazinecarboxamide To a suspension of (R)-2-((1s,4S)-4-(6-fluoroquinolin-4-yl)cyclohexyl)propanehydrazide, 2 HCl (42 mg, 0.108 mmol) in THF (2 mL) was added 4-fluorophenyl isocynate (17.05 mg, 0.124 mmol) in THF and TEA (0.09 mL, 0.649 mmol). The reaction mixture was stirred at rt for 2 h. The reaction mixture was quenched with MeOH and concentrated in vacuo. give Intermediate 7A (white solid, 44 mg, 0.097 mmol, 90% yield). The crude product was used in the next step reaction without purification. LC-MS Anal. Calc'd for $C_{25}H_{26}F_2N_4O_2$, 452.20 found [M+H] 453.2 T$_r$=0.71 min (Method A).

Example 7 N-(4-Fluorophenyl)-5-((R)-1-((1s,4S)-4-(6-fluoroquinolin-4-yl)cyclohexyl)ethyl)-1,3,4-thiadiazol-2-amine The reaction mixture of N-(4-fluorophenyl)-2-((R)-2-((1s,4S)-4-(6-fluoroquinolin-4-yl)cyclohexyl)propanoyl) hydrazinecarboxamide (20 mg, 0.044 mmol) and Lawesson's reagent (71.5 mg, 0.177 mmol) in toluene (4 mL) was heated at 120° C. for 20 h. The reaction mixture was cooled down and diluted with ethyl acetate and 1 N NaOH solution. The organic layer was separated and concentrated in vacuo. and the residue was dissolved in MeOH, purified by preparative HPLC. Fractions containing the desired product were combined, dried via centrifugal evaporation to give Example 7 (3.5 mg, 0.0072 mmol, 16.3% yield). LC-MS Anal. Calc'd for $C_{25}H_{24}F_2N_4S$ 450.17, found [M+H] 451.2 T$_r$=1.63 min (Method B). $^1$H NMR (500 MHz, DMSO-d$_6$) δ: 8.83 (d, J=3.9 Hz, 1H), 8.16-8.04 (m, 1H), 7.97 (d, J=10.5 Hz, 1H), 7.73-7.50 (m, 4H), 7.16 (t, J=8.4 Hz, 2H), 3.67-3.34 (m, 2H), 2.07-1.56 (m, 8H), 1.44 (d, J=12.1 Hz, 1H), 1.30 (d, J=6.5 Hz, 3H)

Examples 9-15

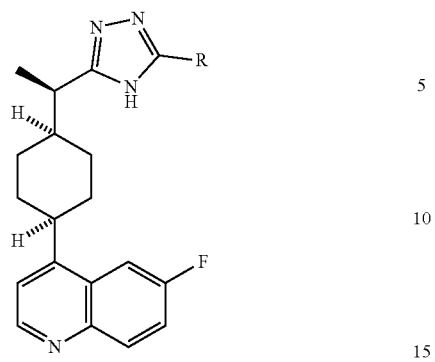

Examples 9-15 were prepared from Intermediate 1B following the procedure for Example 1 using the corresponding imidamide.

| Ex. No. | Name | R | Tr (min) Method B * | [M + H]+ |
|---|---|---|---|---|
| Example 9 | 6-fluoro-4-(1S,4s)-4-((R)-1-(5-(4-methoxyphenyl)-4H-1,2,4-triazol-3-yl)ethyl)cyclohexyl)quinoline | 4-methoxyphenyl | 1.27 | 431.3 |
| Example 10 | 6-fluoro-4-((1S,4s)-4-((R)-1-(5-(3-fluoro-4-methylphenyl)-4H-1,2,4-triazol-3-yl)ethyl)cyclohexyl)quinoline | 3-fluoro-4-methylphenyl | 1.55 | 433.2 |
| Example 11 | 4-((1S,4s)-4-((R)-1-(5-(3-chloro-4-fluorophenyl)-4H-1,2,4-triazol-3-yl)ethyl)cyclohexyl)-6-fluoroquinoline | 3-chloro-4-fluorophenyl | 1.66 | 453.1 |
| Example 12 | 6-fluoro-4-((1S,4s)-4-((R)-1-(5-(4-isopropoxyphenyl)-4H-1,2,4-triazol-3-yl)ethyl)cyclohexyl)quinoline | 4-isopropoxyphenyl | 1.50 | 459.4 |
| Example 13 | 6-fluoro-4-((1S,4s)-4-((R)-1-(5-phenyl-4H-1,2,4-triazol-3-yl)ethyl)cyclohexyl)quinoline | phenyl | 1.27 | 400.9 |
| Example 14 | 6-fluoro-4-((1S,4s)-4-((R)-1-(5-(3-fluorophenyl)-4H-1,2,4-triazol-3-yl)ethyl)cyclohexyl)quinoline | 3-fluorophenyl | 1.49 | 419.3 |

-continued

| Ex. No. | Name | R | Tr (min) Method B * | [M + H]+ |
|---|---|---|---|---|
| Example 15 | 6-fluoro-4-((1S,4s)-4-((R)-1-(5-p-tolyl-4H-1,2,4-triazol-3-yl)ethyl)cyclohexyl)quinoline | 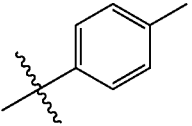 [SMILES: *c1ccc(C)cc1] | 1.35 | 415.3 |

* unless otherwise noted

Examples 16-19

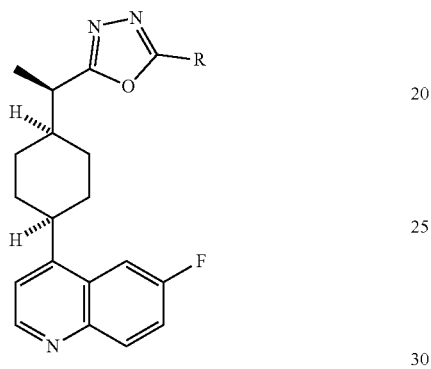

Examples 16-19 were prepared from Intermediate 1B following the procedure for Example 2 or Example 4 using the corresponding imidamide.

| Ex. No. | Name | R | Tr (min) Method B * | [M + H]+ |
|---|---|---|---|---|
| Example 16 | 2-(3-fluoro-4-methylphenyl)-5-((R)-1-((1s,4S)-4-(6-fluoroquinolin-4-yl)cyclohexyl)ethyl)-1,3,4-oxadiazole | 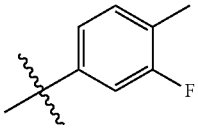 [SMILES: *c1ccc(C)c(F)c1] | 1.82 | 434.1 |
| Example 17 | 2-(3-chloro-4-fluorophenyl)-((R)-1-((1s,4S)-4-(6-fluoroquinolin-4-yl)cyclohexyl)ethyl)-1,3,4-oxadiazole | 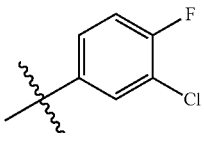 | 1.86 | 454.3 |
| Example 18 | 2-((R)-1-((1s,4S)-4-(6-fluoroquinolin-4-yl)cyclohexyl)ethyl)-5-(4-isopropoxyphenyl)-1,3,4-oxadiazole | 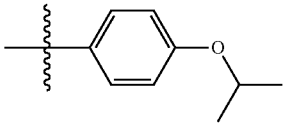 | 2.01 | 460.3 |
| Example 19 | 2-((R)-1-((1s,4S)-4-(6-fluoroquinolin-4-yl)cyclohexyl)ethyl)-5-phenyl-1,3,4-oxadiazole | 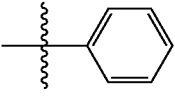 | 1.60 | 402.1 |

* unless otherwise noted

Example 20

5-((R)-1-((1s,4s)-4-(6-Fluoroquinolin-4-yl)cyclohexyl)ethyl)-NV-(4-methoxyphenyl)-4H-1,2,4-triazol-3-amine

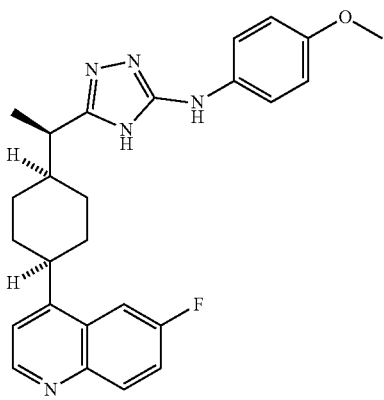 [SMILES: COc1ccc(Nc2nnc([C@H](C)[C@H]3CC[C@@H](c4ccnc5ccc(F)cc54)CC3)[nH]2)cc1]

20A. 1-(4-methoxyphenyl)thiourea

To a solution of 1-isothiocyanato-4-methoxybenzene (0.60 g, 3.63 mmol) in acetonitrile (5 mL) was added ammonium hydroxide solution (28% wt. solution) (4.55 g, 36.3 mmol). The reaction mixture was stirred at rt for 1 h. White solid crashed out. The solid was filtered to give Intermediate 20A (white solid, 0.65 g, 3.57 mmol, 98% yield). LC-MS Anal. Calc'd for $C_8H_{10}N_2OS$, 182.05 found [M+H] 183.0 $T_r$=0.55 min (Method A).

20B. methyl 4-methoxyphenylcarbamimidothioate

To a solution of 1-(4-methoxyphenyl)thiourea (0.65 g, 3.57 mmol) in acetonitrile (12 mL) was added methyl iodide (1.12 mL, 17.83 mmol). The reaction mixture was heated at 65° C. under nitrogen stream for 3 h. The reaction mixture was concentrated in vacuo to afford Intermediate 20B as HI salt (white solid, 1.1 g, 3.40 mmol, 95% yield). LC-MS Anal. Calc'd for $C_9H_{12}N_2OS.HI$ 196.07 found [M+H] 197.0 $T_r$=0.50 min (Method A $^1$H NMR (400 MHz, DMSO-$d_6$) δ: 7.27 (d, J=9.0 Hz, 2H), 7.06 (d, J=9.0 Hz, 2H), 3.80 (s, 3H), 2.67 (s, 3H)

Example 20 5-((R)-1-((1s,4s)-4-(6-Fluoroquinolin-4-yl)cyclohexyl)ethyl)-N-(4-methoxyphenyl)-4H-1,2,4-triazol-3-amine The reaction mixture of methyl (4-methoxyphenyl)carbamimidothioate, iodide salt (27.0 mg, 0.084 mmol), and (R)-2-((1s,4S)-4-(6-fluoroquinolin-4-yl)cyclohexyl)propanehydrazide, 2 HCl (25 mg, 0.064 mmol) (Intermediate 1B of Example 1) in pyridine (1.0 mL) and TEA (0.06 mL, 0.39 mmol) in a sealed tube was purged with nitrogen and then heated at 130° C. for 3 h. The reaction mixture was cooled down and diluted with ethyl acetate and NH$_4$Cl solution. The organic layer was separated and concentrated in vacuo. The residue was dissolved in MeOH, purified by preparative HPLC/MS to give Example 20 (8.4 mg, 0.018 mmol, 28.1% yield). LC-MS Anal. Calc'd for $C_{26}H_{28}FN_5O$ 445.22, found [M+H] 446.2 $T_r$=1.15 min (Method B). $^1$H NMR (500 MHz, DMSO-d6) δ: 8.82 (d, J=3.6 Hz, 1H), 8.70 (br. s., 1H), 8.08 (dd, J=8.8, 6.1 Hz, 1H), 7.95 (d, J=10.8 Hz, 1H), 7.65 (t, J=8.4 Hz, 1H), 7.53 (d, J=4.0 Hz, 1H), 7.41 (d, J=8.0 Hz, 2H), 6.79 (d, J=8.1 Hz, 2H), 3.71-3.51 (m, 3H), 3.38 (br. s., 1H), 3.27-3.09 (m, 1H), 2.03-1.52 (m, 8H), 1.24 (d, J=6.1 Hz, 4H)

Example 21

N-(4-Fluorophenyl)-5-((R)-1-((1s,4s)-4-(6-fluoroquinolin-4-yl)cyclohexyl)ethyl)-4H-1,2,4-triazol-3-amine

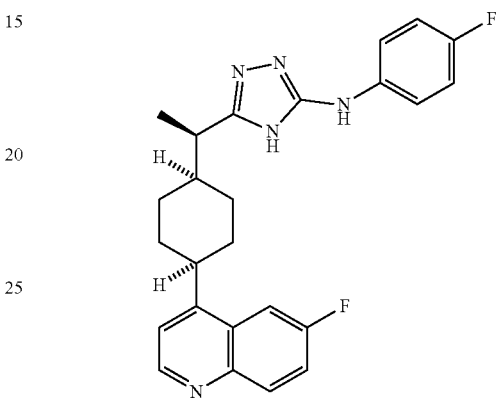

21A. 1-(4-fluorophenyl)thiourea

To a solution of I-fluoro-4-isothiocyanatobenzene (0.5 g, 3.26 mmol) in acetonitrile (5 mL) was added ammonium hydroxide solution (4.09 g, 32.6 mmol, 28% wt.). The reaction mixture was stirred at rt for 1 h. The reaction mixture was diluted with saturated NaHCO$_3$ solution and ethyl acetate. The organic layer was separated and dried over MgSO$_4$. The filtrate was concentrated in vacuo to give Intermediate 21A (white solid, 0.53 g, 3.11 mmol, 95% yield), LC-MS Anal. Calc'd for $C_7H_7FN_2S$ 170.03, found [M+H] 171.0. $T_r$=0.56 min (Method A).

21B. methyl 4-fluorophenylcarbamimidothioate

To a solution of 1-(4-fluorophenyl)thiourea (0.53 g, 3.11 mmol) in acetonitrile (18 mL) was added methyl iodide (0.98 mL, 15.57 mmol). The reaction mixture was heated at 65° C. under nitrogen stream for 3 h. The reaction mixture was cooled down and the mixture was concentrated in vacuo to small amount and to the residue was added ether and concentrated in vacuo to give Intermediate 21B (light yellow solid, 0.90 g, 2.89 mmol, 93% yield). LC-MS Anal. Calc'd for $C_8H_9FN_2S.HI$ 184.05, found [M+H] 185.0. $T_r$=0.48 min (Method A). $^1$H NMR (400 MHz, DMSO-$d_6$) δ: 9.26 (br. s., 2H), 7.48-7.30 (m, 4H), 2.68 (s, 3H).

Example 21, N-(4-Fluorophenyl)-5-((R)-1-((1s,4S)-4-(6-fluoroquinolin-4-yl)cyclohexyl)ethyl)-4H-1,2,4-triazol-3-amine The reaction mixture of methyl (4-fluorophenyl)carbamimidothioate, iodide salt (26.0 mg, 0.084 mmol), and (R)-2-((1s,4S)-4-(6-fluoroquinolin-4-yl)cyclohexyl)propanchydrazide, 2 HCl (25 mg, 0.064 mmol) (Intermediate 1B of Example 1) in pyridine (1 mL) and TEA (0.054 mL, 0.386 mmol) in a sealed tube was purged with nitrogen and then heated at 130° C. for 3 h. The reaction mixture was cooled down and diluted with ethyl acetate and NH₄Cl solution. The organic layer was separated and concentrated in vacuo. The residue was dissolved in MeOH, filtered, and purified via preparative HPLC to give Example 21 (8.9 mg, 0.020 mmol, 31.3%). LC-MS Anal. Calc'd for $C_{25}H_{25}F_2N_5$ 433.21, found [M+H] 434.3. $T_r$=1.25 min (Method B). ¹H NMR (500 MHz, DMSO-$d_6$) δ: 9.04 (br. s., 1H), 8.83 (d, J=4.0 Hz, 1H), 8.08 (dd, J=8.9, 5.9 Hz, 1H), 7.96 (d, J=10.6 Hz, 1H), 7.66 (t, J=8.5 Hz, 1H), 7.57-7.45 (m, 3H), 7.03 (t, J=8.5 Hz, 2H), 3.48 (d, J=3.9 Hz, 1H), 3.22 (br. s., 1H), 1.98 (d, J=10.5 Hz, 2H), 1.89-1.52 (m, 6H), 1.26 (d, J=6.4 Hz, 4H)

Example 22

5-((R)-1-((1s,4s)-4-(6-Fluoroquinolin-4-yl)cyclohexyl)ethyl)-N-phenyl-4H-1,2,4-triazol-3-amine

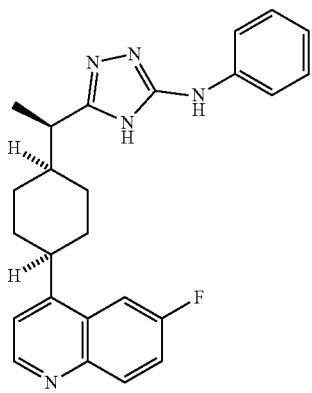 [SMILES: C[C@@H](c1nnc(Nc2ccccc2)[nH]1)[C@H]1CC[C@@H](c2ccnc3ccc(F)cc32)CC1]

Example 22 was prepared from (Intermediate 1B of Example 1) following the procedure for Example 20

The reaction mixture of methyl phenylcarbamimidothioate, iodide salt (25.5 mg, 0.087 mmol), and (R)-2-((1s,4S)-4-(6-fluoroquinolin-4-yl)cyclohexyl)propanehydrazide, 2 HCl (26 mg, 0.067 mmol) (Intermediate 1B of Example 1) in pyridine (1 mL) and TEA (0.06 mL, 0.41 mmol) in a sealed tube was purged with nitrogen and then heated at 120° C. for 3 h. The reaction mixture was cooled down and diluted with ethyl acetate and NH₄Cl solution. The organic layer was separated and concentrated in vacuo. The residue was dissolved in MeOH, filtered, and purified via preparative HPLC to give Example 22 (7.3 mg, 0.017 mmol, 26% yield). LC-MS Anal. Calc'd for $C_{25}H_{26}FN_5$ 415.51. found [M+H] 416.3. $T_r$=1.24 min (Method B). ¹H NMR (500 MHz, DMSO-$d_6$) δ: 8.88 (br. s., 1H), 8.81 (d, J=4.4 Hz, 1H), 8.07 (dd, J=9.1, 5.9 Hz, 1H), 7.94 (d, J=8.9 Hz, 1H), 7.65 (t, J=7.4 Hz, 1H), 7.54 (d, J=4.4 Hz, 1H), 7.47 (d, J=7.8 Hz, 2H), 7.18 (t, J=7.5 Hz, 2H), 6.76 (br. s., 1H), 3.71 (m, 1H), 3.20 (br. s., 1H), 1.96 (d, J=11.4 Hz, 2H), 1.87-1.51 (m, 6H), 1.24 (d, J=6.6 Hz, 4H)

Example 23 5-(4-Chlorophenyl)-N—((R)-1-((1s,4S)-4-(6-fluoroquinolin-4-yl)cyclohexyl)ethyl)-1,3,4-oxadiazol-2-amine

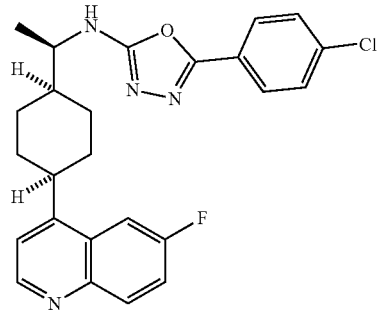 [SMILES: C[C@@H](Nc1nnc(-c2ccc(Cl)cc2)o1)[C@H]1CC[C@@H](c2ccnc3ccc(F)cc32)CC1]

23A tert-butyl 2-(4-chlorobenzoyl)hydrazinecarboxylate

To a solution of 4-chlorobenzoic acid (0.3 g, 1.916 mmol) in DMF (10 mL) was added HATU (0.801 g, 2.108 mmol). The reaction mixture was stirred at rt for 5 min, followed by addition of tert-butyl carbazate (0.28 mL, 2.11 mmol) and morpholine (0.46 mL, 3.83 mmol). The resulting mixture was stirred at rt for 1 h. The reaction mixture was diluted with ethyl acetate and saturated NaHCO₃ solution. The organic layer was separated and washed with brine, and dried over MgSO₄. The filtrate was concentrated in vacuo. The residue was dissolved in DCM and purified by silica gel flash chromatography, eluting with 0-30% ethyl acetate in hexane to give intermediate 23A (white solid, 0.45 g, 1.662 mmol, 87% yield). LC-MS Anal. Calc'd for $C_{12}H_{15}ClN_2O_3$ 270.08, found [M+H] 215.4 (M-55). $T_r$=0.82 min (Method A). ¹H NMR (400 MHz, CHLOROFORM-d) δ: 7.98 (br. s., 1H), 7.75 (d, J=8.6 Hz, 2H), 7.42 (d, J=8.6 Hz, 2H), 6.91-6.40 (m, 1H), 1.51 (s, 9H)

23B 4-chlorobenzohydrazide

To the reaction mixture of tert-butyl 2-(4-chlorobenzoyl)hydrazinecarboxylate (0.42 g, 1.551 mmol) in DCE (7 mL) was added 4 N HCl solution in dioxane (3.10 mL, 12.41 mmol). The resulting mixture was stirred at it for 3 h. The reaction mixture was diluted with DCM, filtered to give Intermediate 23B HCl salt (white solid, 0.3 g, 1.449 mmol, 93% yield). LC-MS Anal. Calc'd for $C_7H_{7Cl}N_2O$·HCl 170.03, found [M+H] 171.4. $T_r$=0.55 min (Method A). ¹H NMR (400 MHz, DMSO-$d_6$) δ: 12.12-11.43 (m, 1H), 10.97-9.58 (m, 2H), 8.11-7.84 (m, 2H), 7.76-7.48 (m, 2H)

23C 2-(4-chlorobenzoyl)-N—((R)-1-((1s,4S)-4-(6-fluoroquinolin-4-yl)cyclohexyl)ethyl)hydrazinecarboxamide To a suspension of (R)-2-((1s,4S)-4-(6-fluoroquinolin-4-yl)cyclohexyl)propanoic acid (0.1 g, 0.332 mmol) in toluene (3 mL) were added diphenylphosphoryl azide (0.083 mL, 0.382 mmol) and TEA (0.06 mL, 0.431 mmol). The reaction mixture in a sealed vial turned into clear solution after addition of TEA. The vial was sealed and heated to 70° C. for 2.5 h. The reaction mixture was cooled to rt. and concentrated under reduced pressure. To a suspension of the crude mixture 6-fluoro-4-((1S,4s)-4-((R)-1-isocyanatoethyl)

cyclohexyl)quinoline (45 mg, 0.151 mmol) in THF (2 mL) was added 4-chlorobenzohydrazide, HCl (35.9 mg, 0.173 mmol) and TEA (0.105 mL, 0.754 mmol). The reaction mixture was stirred at rt for 1 h. The reaction mixture was quenched with MeOH and concentrated in vacuo. The residue was dissolved in MeOH, purified by preparative HPLC. Fractions containing the product were combined and concentrated in vacuo to give Intermediate 23C as TFA salt (white solid, 69 mg, 0.110 mmol, 73% yield). LC-MS Anal. Calc'd for $C_{25}H_{26}ClFN_4O_2$. TFA 468.95, found [M+H] 469.6. $T_r$=0.74 min (Method A). $^1$H NMR (400 MHz, METHANOL-$d_4$) δ: 9.05 (d, J=5.7 Hz, 1H), 8.42-8.23 (m, 2H), 8.11 (d, J=5.7 Hz, 1H), 7.98 (ddd, J=9.3, 7.9, 2.6 Hz, 1H), 7.86 (d, J=8.6 Hz, 2H), 7.46 (d, J=8.6 Hz, 2H), 7.31-7.12 (m, 1H), 4.23 (dd, J=10.0, 6.5 Hz, 1H), 3.67 (d, J=7.0 Hz, 1H), 2.16-1.63 (m, 9H), 1.26-1.20 (m, 3H)

Example 23 5-(4-Chlorophenyl)-N—((R)-1-((1s,4S)-4-(6-fluoroquinolin-4-yl)cyclohexyl)ethyl)-1,3,4-oxadiazol-2-amine The reaction mixture of 2-(4-chlorobenzoyl)-N—((R)-1-((1s,4S)-4-(6-fluoroquinolin-4-yl)cyclohexyl)ethyl)hydrazinecarboxamide, TFA (30 mg, 0.051 mmol) in POCl$_3$ (0.2 mL, 2.146 mmol) was heated at 85° C. over night. The reaction mixture was concentrated in vacuo and the residue was dissolved in MeOH, filtered, and purified via preparative HPLC to give example Example 23 (10.7 mg, 0.023 mmol, 45% yield). LC-MS Anal. Calc'd for $C_{25}H_{24}ClFN_4O$ 450.16, found [M+H] 450.9 $T_r$=1.60 min (Method B). $^1$H NMR (500 MHz, DMSO-$d_6$) δ: 8.81 (d, J=4.4 Hz, 1H), 8.08 (dd, J=9.0, 5.9 Hz, 1H), 7.95 (d, J=10.8 Hz, 1H), 7.86-7.75 (m, 3H), 7.65 (t, J=7.4 Hz, 1H), 7.58 (d, J=8.4 Hz, 2H), 7.50 (d, J=4.3 Hz, 1H), 4.00 (d, J=6.5 Hz, 1H), 3.55-3.44 (m, 1H), 1.95-1.57 (m, 9H), 1.25 (d, J=6.2 Hz, 3H).

Example 24

5-(4-Chlorophenyl)-N—((R)-1-((1s,4S)-4-(6-fluoroquinolin-4-yl)cyclohexyl)ethyl)-1,3,4-thiadiazol-2-amine

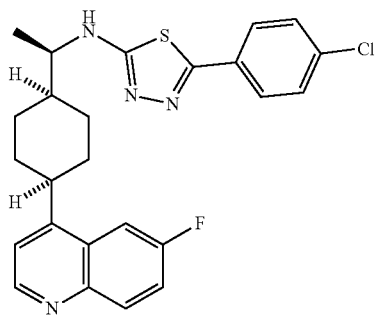 [SMILES: C[C@@H](Nc1nnc(-c2ccc(Cl)cc2)s1)[C@H]1CC[C@@H](c2ccnc3ccc(F)cc32)CC1]

The reaction mixture of 2-(4-chlorobenzoyl)-N—((R)-1-((1s,4S)-4-(6-fluoroquinolin-4-yl)cyclohexyl)ethyl)hydrazinecarboxamide, TFA (35 mg, 0.060 mmol) and lawesson's reagent (97 mg, 0.240 mmol) in toluene (4 mL) was heated at 116° C. for 20 h. The reaction mixture was cooled down and diluted with ethyl acetate and 1 N NaOH solution. The organic layer was separated and concentrated in vacuo. The residue was dissolved in MeOH, filtered, and purified via preparative HPLC to give example Example 24 (5.9 mg, 0.013 mmol, 21% yield). LC-MS Anal. Calc'd for $C_{25}H_{24}ClFN_4S$ 466.14, found [M+H] 467.2 $T_r$=1.62 min (Method B). $^1$H NMR (500 MHz, DMSO-$d_6$) δ: 8.82 (d, J=4.4 Hz, 1H), 8.08 (dd, J=9.0, 5.8 Hz, 1H), 7.96 (d, J=8.7 Hz, 2H), 7.74 (d, J=8.4 Hz, 2H), 7.68-7.60 (m, 11H), 7.51 (d, J=8.2 Hz, 3H), 4.18 (d, J=6.2 Hz, 11H), 3.52 (d, J=5.0 Hz, 1H), 1.98-1.59 (m, 9H), 1.24 (d, J=6.2 Hz, 3H).

Example 25

N—((R)-1-((1s,4S)-4-(6-Fluoroquinolin-4-yl)cyclohexyl)ethyl)-5-(4-methoxyphenyl)-1,3,4-oxadiazol-2-amine

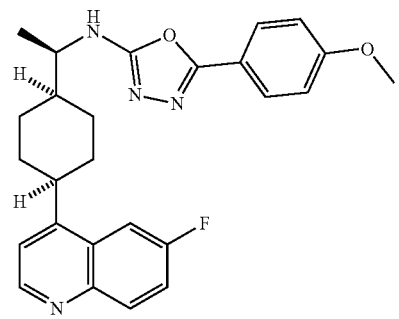

Example 25 was prepared in a similar method as Example 23.

25A tert-butyl 2-(4-methoxybenzoyl)hydrazinecarboxylate

To a solution of 4-methoxybenzoic acid (0.3 g, 1.972 mmol) in DMF (10 mL) was added HATU (0.83 g, 2.169 mmol). The reaction mixture was stirred at rt for 5 min. followed by addition of tert-butyl carbazate (0.287 g, 2.169 mmol) and N-methylmorpholine (0.46 mL, 3.83 mmol). The resulting mixture was stirred at rt for 1 h. The reaction mixture was diluted with ethyl acetate and saturated NaHCO$_3$ solution. The organic layer was separated and washed with brine, and dried over MgSO$_4$. The filtrate was concentrated in vacuo. The residue was dissolved in DCM and purified by silica gel flash chromatography, eluting with 0-35% ethyl acetate in hexane to give Intermediate 25A (white solid, 0.44 g, 1.652 mmol, 84% yield). LC-MS Anal. Calc'd for $C_{13}H_{18}N_2O_4$ 266.13, found [M+H] 211.4 (M-55). $T_r$=0.73 min (Method A). $^1$H NMR (400 MHz, CHLOROFORM-d) δ: 7.78 (d, J=9.0 Hz, 3H), 6.93 (d, J=8.8 Hz, 2H), 3.86 (s, 3H), 1.51 (s, 9H).

25B 4-methoxybenzohydrazide

To the reaction mixture of tert-butyl 2-(4-methoxybenzoyl)hydrazinecarboxylate (0.42 g, 1.551 mmol) in DCE (7 mL) was added 4 N HCl solution in dioxane (3.10 mL, 12.41 mmol). The resulting mixture was stirred at it for 3 h. The reaction mixture was diluted with DCM, filtered to give Intermediate 25B HCl salt (white solid, 0.32 g, 1.579 mmol, 96% yield). LC-MS Anal. Calc'd for $C_8H_{10}N_2O_2$·HCl 166.07, found [M+H] 167.4. $T_r$=0.48 min (Method A). 1H NMR (400 MHz, DMSO-$d_6$) δ:11.41 (br. s., 1H), 10.39 (br. s., 2H), 8.26-7.70 (m, 2H), 7.36-6.89 (m, 2H), 3.84 (s, 3H)

25C. N—((R)-1-((1s,4S)-4-(6-fluoroquinolin-4-yl)cyclohexyl)ethyl)-2-(4-methoxybenzoyl)hydrazinecarboxamide To a suspension of 6-fluoro-4-((1S,4s)-4-((R)-1-isocyanatoethyl)cyclohexyl)quinoline (45 mg, 0.151 mmol) in THF (2 mL) was added 4-methoxybenzohydrazide, HCl (35.1 mg, 0.173 mmol) and TEA (0.105 mL, 0.754 mmol). The reaction mixture was stirred at rt for 2 h. The reaction mixture was quenched with MeOH and concentrated in vacuo. The residue was dissolved in DCM and purified by silica gel flash chromatography, eluting with DCM to 50% of 10% MeOH in DCM to give Intermediate 25C (white solid, 38 mg, 0.082 mmol, 54.2% yield). LC-MS Anal. Calc'd for $C_{26}H_{29}FN_4O_3$ 464.22, found [M+H] 465.6. $T_r$=0.71 min (Method A). $^1$H NMR (400 MHz, METHANOL-$d_4$) δ: 8.21 (d, J=4.6 Hz, 1H), 7.53 (dd, J=9.2, 5.7 Hz, 1H), 7.38-7.25 (m, 3H), 7.12-6.97 (m, 2H), 6.45 (d, J=8.8 Hz, 2H), 5.93 (d, J=9.2 Hz, 1H), 3.78-3.60 (m, 1H), 2.93-2.81 (m, 1H), 1.62-1.09 (m, 9H), 0.69 (d, J=6.6 Hz, 3H).

Example 25 N—((R)-1-((1s,4S)-4-(6-fluoroquinolin-4-yl)cyclohexyl)ethyl)-5-(4-methoxyphenyl)-1,3,4-oxadiazol-2-amine The reaction mixture of N—((R)-1-((1s,4S)-4-(6-fluoroquinolin-4-yl)cyclohexyl)ethyl)-2-(4-methoxybenzoyl)hydrazinecarboxamide (17 mg, 0.037 mmol) in POCl$_3$ (0.2 mL, 2.146 mmol) was heated at 95° C. for 2 h. The reaction mixture was concentrated in vacuo and the residue was dissolved in MeOH, filtered, and purified via preparative HPLC to give example Example 25 (8.7 mg, 0.019 mmol, 52% yield). LC-MS Anal. Calc'd for $C_{26}H_{27}FN_4O_2$ 446.21, found [M+H] 447.1 $T_r$=1.42 min (Method B). $^1$H NMR (500 MHz, DMSO-$d_6$) δ: 8.81 (d, J=4.3 Hz, 1H), 8.08 (dd, J=9.0, 5.8 Hz, 1H), 7.95 (d, J=9.1 Hz, 1H), 7.73 (d, J=8.5 Hz, 2H), 7.65 (d, J=8.6 Hz, 2H), 7.51 (d, J=4.3 Hz, 1H), 7.06 (d, J=8.6 Hz, 2H), 3.97 (d, J=6.7 Hz, 1H), 3.80 (s, 3H), 3.55 (br. s., 1H), 1.96-1.57 (m, 9H), 1.24 (d, J=6.2 Hz, 3H).

Example 26

N—((R)-1-((1s,4S)-4-(6-Fluoroquinolin-4-yl)cyclohexyl)ethyl)-5-(4-methoxyphenyl)-1,3,4-thiadiazol-2-amine

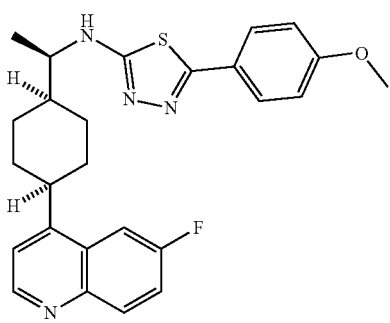 [SMILES: COc1ccc(-c2nnc(N[C@H](C)[C@H]3CC[C@@H](c4ccnc5ccc(F)cc54)CC3)s2)cc1]

Example 26 was prepared in a similar method as Example 24.

The reaction mixture of N—((R)-1-((1s,4S)-4-(6-fluoroquinolin-4-yl)cyclohexyl)ethyl)-2-(4-methoxybenzoyl)hydrazinecarboxamide (18 mg, 0.039 mmol) and lawesson's reagent (62.7 mg, 0.155 mmol) in toluene (3 mL) was heated at 16° C. for 26 h. The reaction mixture was cooled down and diluted with ethyl acetate and 1 N NaOH solution. The organic layer was separated and concentrated in vacuo. The residue was dissolved in MeOH, filtered, and purified via preparative HPLC to give example Example 26 (2.7 mg, 0.00578 mmol, 15% yield). LC-MS Anal. Calc'd for $C_{26}H_{27}FN_4OS$ 462.1, found [M+H] 463.1. $T_r$=1.41 min (Method B). $^1$H NMR (500 MHz, DMSO-$d_6$) δ: 8.82 (d, J=4.3 Hz, 1H), 8.08 (dd, J=9.0, 5.9 Hz, 1H), 7.96 (d, J=8.9 Hz, 1H), 7.77 (d, J=8.5 Hz, 1H), 7.65 (d, J=8.5 Hz, 3H), 7.50 (d, J=4.3 Hz, 1H), 7.01 (d, J=8.6 Hz, 2H), 4.15 (d, J=6.1 Hz, 1H), 3.78 (s, 3H), 3.50 (br. s., 1H), 1.99-1.57 (m, 9H), 1.24 (br. s., 3H).

Example 27

5-Cyclohexyl-N—((R)-1-((1s,4S)-4-(6-fluoroquinolin-4-yl)cyclohexyl)ethyl)-1,3,4-oxadiazol-2-amine

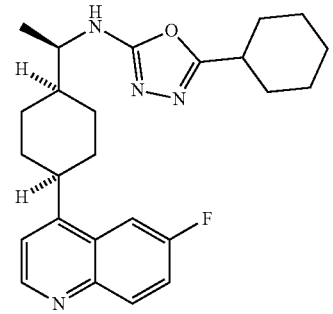 [SMILES: C[C@@H](Nc1nnc(C2CCCCC2)o1)[C@H]1CC[C@@H](c2ccnc3ccc(F)cc32)CC1]

27A 6-fluoro-4-((1S,4s)-4-((R)-1-isocyanatoethyl)cyclohexyl)quinoline

To a solution of (R)-2-((1s,4S)-4-(6-fluoroquinolin-4-yl)cyclohexyl)propanoic acid (400 mg, 1.327 mmol) in toluene (15 mL) were added diphenylphosphoryl azide (0.35 mL, 1.60 mmol) and triethylamine (0.20 mL, 1.73 mmol). The reaction mixture was heated to 70° C. for 2 h. The reaction mixture was cooled to rt. The reaction mixture was concentrated under reduced pressure. The residue was used in the next step reaction without purification.

27B. tert-butyl 2-((R)-1-((1s,4S)-4-(6-fluoroquinolin-4-yl)cyclohexyl)ethylcarbamoyl)hydrazinecarboxylate To a solution of 6-fluoro-4-((1S,4s)-4-((R)-1-isocyanatoethyl)cyclohexyl)quinoline (310 mg, 1.039 mmol) in THF (5 mL) were added tert-butyl hydrazinecarboxylate (165 mg, 1.247 mmol) and DIPEA (0.36 mL, 2.078 mmol). The reaction mixture was stirred at it for 1 h. The reaction mixture was concentrated in vacuo. The residue was dissolved in DCM and purified by silica gel flash chromatography, eluting with 0-10% ethyl acetate in hexane to give Intermediate 27B (white solid, 0.30 g, 0.697 mmol, 67% yield). LC-MS Anal. Calc'd for $C_{21}H_{31}FN_4O_3$ 430.24, found [M+H] 431.3. $T_r$=0.70 min (Method A). $^1$H NMR (400 MHz, CHLOROFORM-d) δ: 8.81 (d, J=4.6 Hz, 1H), 8.12 (dd, J=9.2, 5.7 Hz, 1H), 7.66 (dd, J=10.6, 2.7 Hz, 1H), 7.46 (ddd, J=9.2, 8.0, 2.8 Hz, 1H), 7.39 (d, J=4.6 Hz, 1H), 6.20 (s, 1H), 5.95 (s, 1H), 5.06 (d, J=9.3 Hz, 1H), 4.26 (tq, J=9.7, 6.5 Hz, 1H), 3.50 (d, J=4.9 Hz, 4H), 3.34-3.15 (m, 11H), 2.04-1.61 (m, 9H), 1.49 (s, 9H), 1.24-1.18 (m, 3H), 1.09-0.93 (m, 1H).

27C. N—((R)-1-((1s,4S)-4-(6-fluoroquinolin-4-yl)cyclohexyl)ethyl)hydrazinecarboxamide To a solution of tert-butyl 2-(((R)-1-((1s,4S)-4-(6-fluoroquinolin-4-yl)cyclohexyl)ethyl)carbamoyl)hydrazinecarboxylate (0.3 g, 0.697 mmol) in DCM (6 mL) was added HCl (4.0 M solution in dioxane) (3.5 mL, 13.94 mmol). The reaction mixture was stirred at rt for 2 h. White solid crashed out. The reaction mixture was concentrated in vacuo to give Intermediate 27C 2HCl salt (white solid, 0.25 g, 0.62 mmol, 89% yield). LC-MS Anal. Calc'd for $C_{18}H_{23}FN_4O\cdot 2$ HCl 330.19, found [M+H] 331.45. $T_r$=0.83 min (Method A). $^1$H NMR (400 MHz, METHANOL-$d_4$) δ: 9.11 (d, J=5.9 Hz, 1H), 8.41-8.25 (m, 2H), 8.12 (d, J=5.7 Hz, 1H), 8.02 (ddd, J=9.5, 7.9, 2.6 Hz, 1H), 4.33-4.09 (m, 1H), 3.78-3.69 (m, 1H), 2.17-1.65 (m, 9H), 1.25 (d, J=6.6 Hz, 3H)

27D. 2-(cyclohexanecarbonyl)-N—((R)-1-((1s,4S)-4-(6-fluoroquinolin-4-yl)cyclohexyl)ethyl)hydrazinecarboxamide To a solution of cyclohexanecarboxylic acid (12.39 mg, 0.097 mmol) in DMF (1 mL) was added HATU (36.8 mg, 0.097 mmol). The reaction mixture was stirred at rt for 5 min. followed by addition of N—((R)-1-((1s,4S)-4-(6-fluoroquinolin-4-yl)cyclohexyl)ethyl)hydrazinecarboxamide, 2 HCl (30 mg, 0.074 mmol) and DIPEA (0.13 mL, 0.744 mmol). The resulting mixture was stirred at rt for 2 h. The reaction mixture was extracted with ethyl acetate. The organic layer was separated and concentrated in vacuo. The crude extract was used in the next step reaction without purification.

Example 27 5-cyclohexyl-N—((R)-1-((1s,4S)-4-(6-fluoroquinolin-4-yl)cyclohexyl)ethyl)-1,3,4-oxadiazol-2-amine The reaction mixture of 2-(cyclohexanecarbonyl)-N—((R)-1-((1s,4S)-4-(6-fluoroquinolin-4-yl)cyclohexyl)ethyl)hydrazinecarboxamide (30 mg, 0.068 mmol) in POCl$_3$ (0.3 mL, 3.22 mmol) was purged with nitrogen stream for 1 min, then the vial was sealed and heated at 100° C. for 3 h. The reaction mixture was cooled down. The reaction mixture was concentrated in vacuo and the residue was dissolved in MeOH, filtered and purified via preparative HPLC to give Example 27 (13 mg, 0.030 mmol, 44% yield). LC-MS Anal. Calc'd for $C_{25}H_{31}FN_4O$ 422.25, found [M+H] 423.1, $T_r$=1.37 min (Method B). $^1$H NMR (500 MHz, DMSO-$d_6$) δ: 8.88 (d, J=4.6 Hz, 1H), 8.13 (dd, J=9.1, 5.8 Hz, 1H), 8.04 (d, J=8.7 Hz, 1H), 7.79-7.68 (m, 1H), 7.59 (d, J=4.6 Hz, 1H), 7.50 (d, J=8.7 Hz, 1H), 3.87 (d, J=6.3 Hz, 1H), 2.99-2.85 (m, 1H), 2.71 (t, J=10.8 Hz, 1H), 1.97-1.53 (m, 13H), 1.48-1.26 (m, 4H), 1.24-1.09 (m, 5H).

Examples 28-35 were prepared following the procedure for Example 25 or Example 27 using the corresponding acid.

| Ex. No. | Name | R | Tr (min) Method B * | [M + H]$^+$ |
|---|---|---|---|---|
| Example 28 | 5-cyclopropyl-N-((R)-1-((1s,4S)-4-(6-fluoroquinolin-4-yl)cyclohexyl)ethyl)-1,3,4-oxadiazol-2-amine | cyclopropyl | 1.29 | 380.9 |
| Example 29 | 4-(5-((R)-1-((1s,4S)-4-(6-fluoroquinolin-4-yl)cyclohexyl)ethylamino)-1,3,4-oxadiazol-2-yl)benzonitrile | 4-cyanophenyl | 1.37 | 442.2 |
| Example 30 | N-((R)-1-((1s,4S)-4-(6-fluoroquinolin-4-yl)cyclohexyl)ethyl)-5-(5-methylthiazol-2-yl)-1,3,4-oxadiazol-2-amine | 5-methylthiazol-2-yl | 1.28 | 437.9 |
| Example 31 | 5-(4-fluorophenyl)-N-((R)-1-((1s,4S)-4-(6-fluoroquinolin-4-yl)cyclohexyl)ethyl)-1,3,4-oxadiazol-2-amine | 4-fluorophenyl | 1.41 | 435.2 |
| Example 32 | N-((R)-1-((1s,4S)-4-(6-fluoroquinolin-4-yl)cyclohexyl)ethyl)-5-(4-methylthiazol-2-yl)-1,3,4-oxadiazol-2-amine | 4-methylthiazol-2-yl | 1.23 | 438.1 |

-continued

| Ex. No. | Name | R | Tr (min) Method B * | [M + H]+ |
|---|---|---|---|---|
| Example 33 | N-((R)-1-((1s,4S)-4-(6-fluoroquinolin-4-yl)cyclohexyl)ethyl)-5-(6-methoxypyridin-3-yl)-1,3,4-oxadiazol-2-amine | 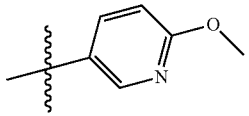 [SMILES: *c1ccc(OC)nc1] | 1.31 | 448.1 |
| Example 34 | N-((R)-1-((1s,4S)-4-(6-fluoroquinolin-4-yl)cyclohexyl)ethyl)-5-(methoxymethyl)-1,3,4-oxadiazol-2-amine | 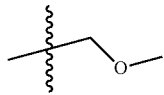 [SMILES: *COC] | 1.06 | 385.3 |
| Example 35 | N-((R)-1-((1s,4S)-4-(6-fluoroquinolin-4-yl)cyclohexyl)ethyl)-5-(4-(thiazol-2-yl)phenyl)-1,3,4-oxadiazol-2-amine | 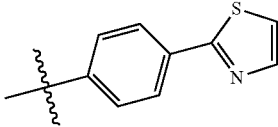 [SMILES: *c1ccc(-c2nccs2)cc1] | 1.45 | 500.0 |

* unless otherwise noted

Example 36

N—((R)-1-((1s,4S)-4-(6-Fluoroquinolin-4-yl)cyclohexyl)ethyl)-4-(4-methoxyphenyl)thiazol-2-amine

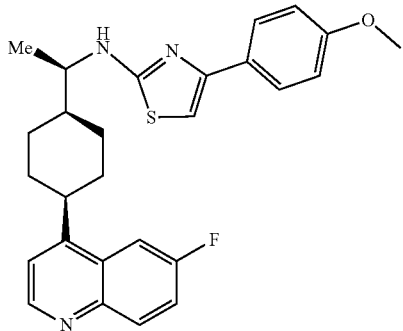 [SMILES: COc1ccc(-c2csc(N[C@H](C)[C@H]3CC[C@@H](c4ccnc5ccc(F)cc54)CC3)n2)cc1]

36A 1-((R)-1-((1s,4S)-4-(6-fluoroquinolin-4-yl)cyclohexyl)ethyl)thiourea

To the reaction mixture of O-((9H-fluoren-9-yl)methyl) carbonisothiocyanatidate (91 mg, 0.323 mmol) in DCE (2 mL) were added DIPEA (0.11 mL, 0.59 mmol) and (R)-1-((1s,4S)-4-(6-fluoroquinolin-4-yl)cyclohexyl)ethanamine (80 mg, 0.294 mmol) (Intermediate) in DCM (2 mL). The reaction mixture was stirred at rt for 1 h. To the reaction mixture was added more O-((9H-fluoren-9-yl)methyl) carbonisothiocyanatidate (20 mg) and THF (2 ml). The reaction mixture was stirred at rt over night. To the reaction mixture was added piperidine (0.60 mL, 5.9 mmol) and the reaction mixture was stirred at rt for 1 h. The reaction mixture was diluted with MeOH, concentrated in vacuo. The residue was dissolved in DCM and purified by silica gel flash chromatography, eluting with 0-50% of 10% MeOH in DCM to give Intermediate 36A (white solid, 11 mg, 0.033 mmol, 11.3% yield). LC-MS Anal. Calc'd for $C_{18}H_{22}FN_3S$ 331.45, found [M+H] 332.5. $T_r$=0.63 min (Method A).

Example 36 N—((R)-1-((1s,4S)-4-(6-Fluoroquinolin-4-yl)cyclohexyl)ethyl)-4-(4-methoxyphenyl)thiazol-2-amine To the reaction mixture of 1-((R)-1-((1s,4S)-4-(6-fluoroquinolin-4-yl)cyclohexyl)ethyl)thiourea (11 mg, 0.033 mmol) and 2-bromo-1-(4-methoxyphenyl)ethanone (11.40 mg, 0.050 mmol) was added 1,4-dioxane (3 mL). The resulting mixture was heated at 68° C. for 1.5 h. The reaction mixture was concentrated in vacuo and the residue was dissolved in MeOH, filtered, and purified via preparative HPLC to give example Example 36 (10.7 mg, 0.023 mmol, 69% yield). LC-MS Anal. Calc'd for $C_{27}H_{28}FN_3OS$ 461.19, found [M+H] 462.3 $T_r$=1.34 min (Method B). $^1$H NMR (500 MHz, DMSO-$d_6$) δ: 8.80 (d, J=4.5 Hz, 1H), 8.08 (dd, J=9.0, 5.8 Hz, 1H), 8.00-7.92 (m, 1H), 7.74 (d, J=8.5 Hz, 2H), 7.69-7.60 (m, 1H), 7.55-7.47 (m, 2H), 6.90 (d, J=8.6 Hz, 2H), 6.79 (s, 1H), 4.19 (d, J=6.3 Hz, 1H), 3.76 (s, 3H), 3.44 (br. s., 1H), 1.99-1.54 (m, 9H), 1.24 (d, J=6.3 Hz, 3H).

Example 37

4-(4-Chlorophenyl)-N—((R)-1-((1s,4S)-4-(6-fluoroquinolin-4-yl)cyclohexyl)ethyl)thiazol-2-amine

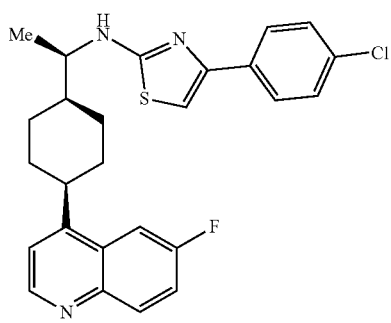 [SMILES: C[C@@H](Nc1nc(-c2ccc(Cl)cc2)cs1)[C@H]1CC[C@@H](c2ccnc3ccc(F)cc32)CC1]

37A 1-(4-chlorophenyl)-2-thiocyanatoethanone

The reaction mixture of 2-bromo-1-(4-chlorophenyl)ethanone (0.6 g, 2.57 mmol), ammonium thiocynate (0.26 g, 3.35 mmol) in acetonitrile (10 mL) was stirred at rt for 2 h. Solid was precipitated out. The upper layer solution was used for next step reaction. LC-MS Anal. Calc'd for $C_9H_6ClNOS$ 210.99, found [M+H] 211.9 $T_r$=0.92 min (Method A).

Example 37 4-(4-Chlorophenyl)-N—((R)-1-((1s,4S)-4-(6-fluoroquinolin-4-yl)cyclohexyl)ethyl)thiazol-2-amine To the solution of (R)-1-((1s,4S)-4-(6-fluoroquinolin-4-yl)cyclohexyl)ethanamine (30 mg, 0.110 mmol) in dioxane (2 mL) was added the crude solution of 1-(4-chlorophenyl)-2-thiocyanatoethanone (25.6 mg, 0.121 mmol) in $CH_3CN$. The reaction mixture was heated at 65° C. for 1 h. More solution of 1-(4-chlorophenyl)-2-thiocyanatoethanone (25.6 mg, 0.121 mmol) in $CH_3CN$ and TEA (0.3 mL) were added, then heated at 100° C. for 2.5 h. The reaction mixture was diluted with ethyl acetate and sat. $NaHCO_3$ solution. The organic layer was separated and washed with brine, and concentrated in vacuo. and the residue was dissolved in MeOH, filtered, and purified via preparative HPLC to give Example 37 (9.4 mg, 0.020 mmol, 18.1% yield). LC-MS Anal. Calc'd for $C_{26}H_{25}ClFN_3S$ 465.14, found [M+H] 465.9 $T_r$=1.55 min (Method B). $^1$H NMR (500 MHz, DMSO-$d_6$) δ: 8.80 (d, J=4.5 Hz, 1H), 8.08 (dd, J=9.0, 5.9 Hz, 1H), 8.00-7.91 (m, 1H), 7.83 (d, J=8.4 Hz, 2H), 7.70-7.56 (m, 2H), 7.49 (d, J=4.4 Hz, 1H), 7.40 (d, J=8.3 Hz, 2H), 7.04 (s, 1H), 4.21 (br. s., 1H), 3.89 (s, 1H), 1.98-1.51 (m, 9H), 1.24 (d, J=6.3 Hz, 3H).

Example 38

5-(4-Chlorophenyl)-N—((R)-1-((1s,4S)-4-(6-fluoroquinolin-4-yl)cyclohexyl)ethyl)oxazol-2-amine

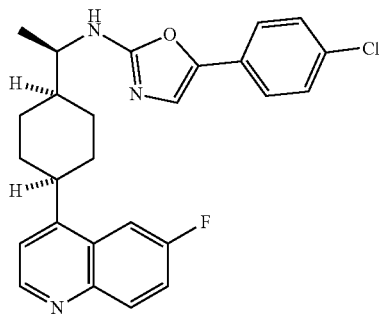 [SMILES: C[C@@H](Nc1ncc(-c2ccc(Cl)cc2)o1)[C@H]1CC[C@@H](c2ccnc3ccc(F)cc32)CC1]

38A 1-(2-(4-chlorophenyl)-2-oxoethyl)-3-((R)-1-((1s,4S)-4-(6-fluoroquinolin-4-yl)cyclohexyl)ethyl)urea To a solution of (R)-2-((1s,4S)-4-(6-fluoroquinolin-4-yl)cyclohexyl)propanoic acid (120 mg, 0.398 mmol) in Toluene (5 mL) were added DPPA (0.11 mL, 0.5 mmol) and triethylamine (0.1 mL, 0.6 mmol). The reaction mixture was heated to 70° C. for 2 h. The reaction was cooled to rt and concentrated under reduced pressure. The residue was used in the next step reaction without purification. To a solution of crude 6-fluor-4-((1S,4s)-4-((R)-1-isocyanatoethyl)cyclohexyl)quinoline (85 mg, 0.285 mmol) in THF (2 mL) were added 2-amino-1-(4-chlorophenyl)ethanone, HCl (88 mg, 0.427 mmol) (intermediate) and DIPEA (0.3 mL, 1.71 mmol). The reaction mixture was stirred at rt for 1 h. The reaction mixture was diluted with ethyl acetate and saturated $NaHCO_3$ solution. The organic layer was separated and concentrated in vacuo. and the residue was dissolved in MeOH, filtered, and purified via preparative HPLC to give Intermediate 38A as a TFA salt (white solid, 90 mg, 0.139 mmol, 49% yield). LC-MS Anal. Calc'd for $C_{26}H_{27}ClFN_3O_2$. TFA 467.17. found [M+H] 468.2. $T_r$=0.80 min (Method A).

Example 38, 5-(4-Chlorophenyl)-N—((R)-1-((1s,4S)-4-(6-fluoroquinolin-4-yl)cyclohexyl)ethyl)oxazol-2-amine The reaction mixture of 1-(2-(4-chlorophenyl)-2-oxoethyl)-3-((R)-1-((1s,4S)-4-(6-fluoroquinolin-4-yl)cyclohexyl)ethyl)urea, TFA (32 mg, 0.055 mmol) in $POCl_3$ (0.3 mL, 2.15 mmol) was heated at 110° C. over night. The reaction mixture was concentrated in vacuo and the residue was dissolved in MeOH, filtered, and purified via preparative HPLC to give example Example 38 (6.5 mg, 0.014 mmol, 26% yield). LC-MS Anal. Calc'd for $C_{26}H_{25}ClFN_3O$ 449.17, found [M+H] 450.1 $T_r$=1.50 min (Method B). $^1$H NMR (500 MHz, DMSO-$d_6$) δ: 8.81 (br. s., 1H), 8.08 (d, J=8.5 Hz, 1H), 7.94 (d, J=8.9 Hz, 1H), 7.75-7.60 (m, 1H), 7.53-7.33 (m, 6H), 4.01 (br. s., 1H), 1.97-1.48 (m, 10H), 1.20 (d, J=6.4 Hz, 3H).

Example 39

5-(4-Chlorophenyl)-N—((R)-1-((1s,4S)-4-(6-fluoroquinolin-4-yl)cyclohexyl)ethyl)thiazol-2-amine

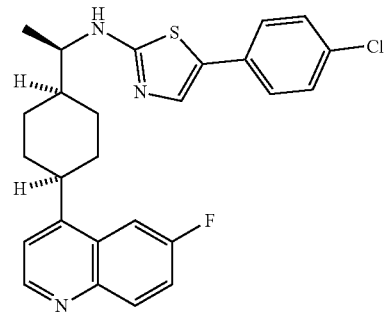

Example 39 5-(4-Chlorophenyl)-N—((R)-1-((1s,4S)-4-(6-fluoroquinolin-4-yl)cyclohexyl)ethyl)thiazol-2-amine The reaction mixture of 1-(2-(4-chlorophenyl)-2-oxoethyl)-3-((R)-1-((1s,4S)-4-(6-fluoroquinolin-4-yl)cyclohexyl)ethyl)urea, TFA (45 mg, 0.077 mmol) and Lawesson's Reagent (125 mg, 0.31 mmol) in Toluene (2 mL) and DIPEA (0.3 mL) was heated at 110° C. for 20 h. The reaction mixture was cooled down and diluted with ethyl acetate and 1 N NaOH solution. The organic layer was separated and concentrated in vacuo. and the residue was dissolved in MeOH, filtered, and purified via preparative HPLC to give example Example 39 (1.1 mg, 0.002 mmol, 2.8% yield). LC-MS Anal. Calc'd for $C_{26}H_{25}ClFN_3S$ 465.14, found [M+H] 466.3. $T_r$=1.59 min (Method B). $^1$H NMR (500 MHz, DMSO-$d_6$) δ: 8.82 (d, J=4.6 Hz, 1H), 8.08 (dd, J=9.0, 6.0 Hz, 1H), 7.96 (d, J=11.0 Hz, 1H), 7.75 (d, J=8.5 Hz, 1H), 7.66 (t, J=8.5 Hz, 1H), 7.54-7.27 (m, 5H), 4.12 (br. s., 1H), 3.85-3.71 (m, 1H), 1.99-1.56 (m, 9H), 1.21 (d, J=6.4 Hz, 3H).

Example 40

5-(4-Chlorophenyl)-N—((R)-1-((1s,4S)-4-(6-fluoro-quinolin-4-yl)cyclohexyl)ethyl)-4H-1,2,4-triazol-3-amine

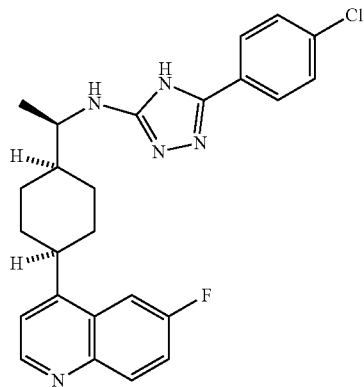 [SMILES: C[C@@H](Nc1nnc(-c2ccc(Cl)cc2)[nH]1)[C@H]1CC[C@@H](c2ccnc3ccc(F)cc32)CC1]

40A. N—((R)-1-((1s,4S)-4-(6-fluoroquinolin-4-yl)cyclohexyl)ethylcarbamothioyl)benzamide To a solution benzoyl isothiocyanate (79 mg, 0.485 mmol) in acetonitrile (4 mL) was added a solution of (R)-1-((1s,4S)-4-(6-fluoroquinolin-4-yl)cyclohexyl)ethanamine (110 mg, 0.404 mmol) (Intermediate) in THF (2 mL) and DIPEA (0.141 mL, 0.808 mmol). The reaction mixture was stirred at rt for 1 h. The reaction mixture was concentrated in vacuo. The residue was dissolved in DCM and purified by silica gel flash chromatography, eluting with 0-30% of ethyl acetate in hexane to give Intermediate 40A (white solid, 155 mg, 0.356 mmol, 88% yield). LC-MS Anal. Calc'd for $C_{25}H_{26}FN_3OS$, 435.18 found [M+H] 436.3 $T_r$=0.91 min (Method A). $^1$H NMR (400 MHz, CHLOROFORM-d) δ: 10.81 (d, J=8.6 Hz, 1H), 8.76 (d, J=4.6 Hz, 1H), 8.08 (dd, J=9.1, 5.6 Hz, 1H), 7.93-7.82 (m, 2H), 7.65 (dd, J=10.6, 2.6 Hz, 1H), 7.62-7.55 (m, 1H), 7.53-7.38 (m, 4H), 4.91 (dt, J=9.6, 6.4 Hz, 1H), 3.34-3.20 (m, 1H), 1.16-1.65 (m, 9H), 1.35 (d, J=6.6 Hz, 3H)

40B 1-((R)-1-((1s,4S)-4-(6-fluoroquinolin-4-yl)cyclohexyl)ethyl)thiourea

To the reaction mixture of N—(((R)-1-((1s,4S)-4-(6-fluoroquinolin-4-yl)cyclohexyl)ethyl)carbamothioyl)benzamide (155 mg, 0.356 mmol) in THF (3 mL) was added 1N sodium hydroxide solution (2.14 mL, 2.14 mmol). The reaction mixture was stirred at rt for 2 h. The reaction mixture was extracted with ethyl acetate, washed with saturated NaHCO$_3$ solution. The organic layer was concentrated in vacuo to give Intermediate 40B (white solid, 100 mg, 0.302 mmol, 85% yield). LC-MS Anal. Calc'd for $C_{18}H_{22}FN_3S$ 331.15, found [M+H] 332.3 $T_r$=0.61 min (Method A). $^1$H NMR (400 MHz, METHANOL-d$_4$) δ: 8.74 (d, J=4.6 Hz, 1H), 8.05 (dd, J=9.2, 5.7 Hz, 1H), 7.84 (dd, J=10.7, 2.5 Hz, 1H), 7.67-7.49 (m, 2H), 4.79-4.67 (m, 1H), 3.45-3.34 (m, 1H), 2.22-1.59 (m, 9H), 1.21 (d, J=6.4 Hz, 3H)

40C methyl (R)-1-((1s,4S)-4-(6-fluoroquinolin-4-yl)cyclohexyl)ethylcarbamimidothioate To a solution of 1-((R)-1-((1s,4S)-4-(6-fluoroquinolin-4-yl)cyclohexyl)thiourea (170 mg, 0.513 mmol) in acetonitrile (8 mL) was added iodomethane (0.1 mL, 1.6 mmol). The reaction mixture was stirred at rt under nitrogen stream for 18 h. The reaction mixture was diluted with ethyl acetate and saturated NaHCO$_3$ solution. The organic layer was separated and washed with brine, dried over MgSO$_4$. The filtrate was concentrated in vacuo to give Intermediate 40C (white solid, 106 mg, 0.307 mmol, 60% yield). LC-MS Anal. Calc'd for $C_{19}H_{24}FN_3S$ 345.17, found [M+H] 346.2 $T_r$=0.62 min (Method A). $^1$H NMR (400 MHz, CHLOROFORM-d) δ: 8.81 (d, J=4.6 Hz, 1H), 8.12 (dd, J=9.1, 5.8 Hz, 1H), 7.67 (dd, J=10.7, 2.8 Hz, 1H), 7.47 (ddd, J=9.2, 8.0, 2.6 Hz, 1H), 7.37 (d, J=4.6 Hz, 1H), 4.31 (br. s., 1H), 3.37-3.18 (m, 1H), 2.36 (s, 3H), 2.06-1.59 (m, 9H), 1.30-1.23 (m, 3H)

Example 40 5-(4-chlorophenyl)-N—((R)-1-((1s,4S)-4-(6-fluoroquinolin-4-yl)cyclohexyl)ethyl)-4H-1,2,4-triazol-3-amine The reaction mixture of 4-chlorobenzohydrazide, HCl (23.01 mg, 0.111 mmol), and methyl ((R)-1-((1s,4S)-4-(6-fluoroquinolin-4-yl)cyclohexyl)ethyl)carbamimidothioate (32 mg, 0.093 mmol) in pyridine (0.8 mL) and TEA (0.077 mL, 0.556 mmol) in a sealed tube was purged with nitrogen and then heated at 120° C. for 20 h. To the reaction mixture was added more 4-chlorobenzohydrazide, HCl (23.01 mg, 0.111 mmol) and TEA (0.077 mL, 0.556 mmol) and the reaction mixture was heated at 134° C. for another 2 h. The reaction mixture was cooled down and diluted with ethyl acetate and NH$_4$Cl solution. The organic layer was separated and concentrated in vacuo. The residue was dissolved in MeOH, filtered, and purified via preparative HPLC to give Example 40 (8.7 mg, 0.019 mmol, 20.7% yield). LC-MS Anal. Calc'd for $C_{25}H_{25}ClFN_5$ 449.18, found [M+H] 450.1, $T_r$=1.25 min (Method T). $^1$H NMR (500 MHz, DMSO-d$_6$) δ: 8.83 (d, J=4.3 Hz, 1H), 8.08 (dd, J=9.0, 5.9 Hz, 1H), 7.96 (d, J=9.2 Hz, 1H), 7.89 (d, J=8.2 Hz, 2H), 7.65 (t, J=7.7 Hz, 1H), 7.54 (d, J=4.0 Hz, 1H), 7.45 (d, J=8.0 Hz, 2H), 6.55 (br. s., 1H), 3.94 (d, J=6.2 Hz, 1H), 3.39 (br. s., 1H), 1.96 (d, J=10.9 Hz, 1H), 1.88-1.48 (m, 8H), 1.17 (d, J=6.0 Hz, 3H).

Example 41

4-(5-((R)-1-((1s,4S)-4-(6-Fluoroquinolin-4-yl)cyclohexyl)ethylamino)-4H-1,2,4-triazol-3-yl)benzonitrile

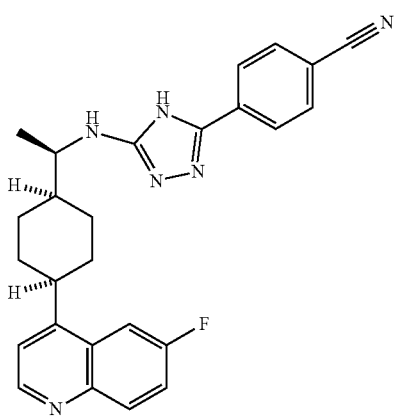 [SMILES: C[C@@H](Nc1nnc(-c2ccc(C#N)cc2)[nH]1)[C@H]1CC[C@@H](c2ccnc3ccc(F)cc32)CC1]

The reaction mixture of 4-cyanobenzohydrazide, HCl (21.97 mg, 0.111 mmol), and methyl ((R)-1-((1s,4S)-4-(6-fluoroquinolin-4-yl)cyclohexyl)ethyl)carbamimidothioate (32 mg, 0.093 mmol) in Pyridine (1 mL) and TEA (0.077 mL, 0.556 mmol) in a sealed tube was purged with nitrogen and then heated at 120° C. for 20 h. The reaction mixture was cooled down and diluted with ethyl acetate and NH$_4$Cl solution. The organic layer was separated and concentrated in vacuo. The residue was dissolved in MeOH, filtered, and purified via preparative HPLC to give Example 41 (11.5 mg, 0.025 mmol, 27% yield). LC-MS Anal. Calc'd for C$_{26}$H$_{25}$FN$_6$ 440.21, found [M+H] 441.2, T$_r$=1.14 min (Method T). $^1$H NMR (500 MHz, DMSO-d$_6$) δ: 8.84 (d, J=4.3 Hz, 1H), 8.13-8.02 (m, 3H), 7.97 (d, J=10.7 Hz, 1H), 7.86 (d, J=7.9 Hz, 2H), 7.66 (t, J=7.4 Hz, 1H), 7.54 (d, J=4.0 Hz, 1H), 6.70 (d, J=9.4 Hz, 1H), 3.95 (d, J=5.8 Hz, 1H), 2.02-1.55 (m, 9H), 1.24-1.12 (m, 4H)

Example 42

N—((R)-1-((1s,4S)-4-(6-Fluoroquinolin-4-yl)cyclohexyl)ethyl)-5-(4-methoxyphenyl)-4H-1,2,4-triazol-3-amine

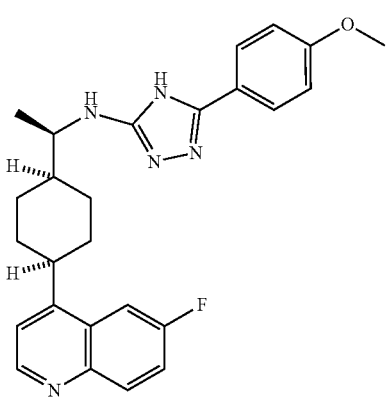 [SMILES: COc1ccc(-c2nnc(N[C@H](C)[C@H]3CC[C@@H](c4ccnc5ccc(F)cc54)CC3)[nH]2)cc1]

The reaction mixture of 4-methoxybenzohydrazide, HCl (22.52 mg, 0.111 mmol), and methyl ((R)-1-((1s,4S)-4-(6-fluoroquinolin-4-yl)cyclohexyl)ethyl)carbamimidothioate (32 mg, 0.093 mmol) in pyridine (1 mL) and TEA (0.077 mL, 0.556 mmol) in a sealed tube was purged with nitrogen and then heated at 120° C. for 20 h. The reaction mixture was cooled down and diluted with ethyl acetate and NH$_4$Cl solution. The organic layer was separated and concentrated in vacuo. The residue was dissolved in MeOH, filtered, and purified via preparative HPLC to give Example 42 (7.7 mg, 0.017 mmol, 18.3% yield). LC-MS Anal. Calc'd for C$_{26}$H$_{28}$FN$_5$O 445.23, found [M+H] 446.0. T$_r$=1.11 min (Method T). $^1$H NMR (500 MHz, DMSO-d$_6$) δ: 8.83 (d, J=4.1 Hz, 1H), 8.08 (dd, J=9.0, 5.9 Hz, 1H), 7.96 (d, J=9.2 Hz, 1H), 7.81 (d, J=8.5 Hz, 2H), 7.70-7.62 (m, 1H), 7.54 (br. s., 1H), 6.96 (d, J=6.8 Hz, 2H), 6.45 (br. s., 1H), 4.03-3.88 (m, 1H), 3.77 (s, 3H), 3.41 (br. s., 1H), 2.03-1.52 (m, 9H), 1.17 (d, J=6.1 Hz, 3H).

Example 43

5-(4-Chlorophenyl)-2-((R)-1-((1s,4S)-4-(6-fluoroquinolin-4-yl)cyclohexyl)ethyl)oxazole

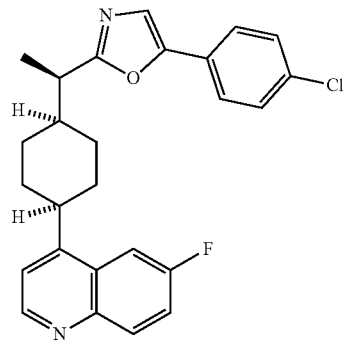 [SMILES: C[C@@H](c1ncc(-c2ccc(Cl)cc2)o1)[C@H]1CC[C@@H](c2ccnc3ccc(F)cc32)CC1]

43A 2-amino-1-(4-chlorophenyl)ethanone

The solution of 2-bromo-1-(4-chlorophenyl)ethanone (1.2 g, 5.14 mmol) and hexamethylenetetramine (0.92 mL, 8.74 mmol) in CHCl$_3$ (25 mL) was stirred at rt for 20 h. The precipitate was filtered out and the solid was washed with DCM, dried on high vacuum. To the solid was added ethanol (95%) (20 mL) and conc. HCl (4.7 mL, 154 mmol). The resulting mixture was heated under reflux for 2 h, then stirred at rt for 2 h. Solid precipitated out during cooling down and the solid was filtered out, washed with ether to give Intermediate 43A as a HCl salt (white solid, 1.0 g, 4.85 mmol, 94% yield). LC-MS Anal. Calc'd for C$_8$H$_8$ClNO. HCl 169.03, found [M+H] 170.0. T$_r$=0.51 min (Method A). $^1$H NMR (400 MHz, DMSO-d$_6$) δ: 8.49 (br. s., 2H), 8.15-7.93 (m, 2H), 7.78-7.63 (m, 2H), 4.74-4.45 (m, 2H).

43B. (R)—N-(2-(4-chlorophenyl)-2-oxoethyl)-2-((1s,4S)-4-(6-fluoroquinolin-4-yl)cyclohexyl)propanamide To a solution of (R)-2-((1s,4S)-4-(6-fluoroquinolin-4-yl)cyclohexyl)propanoic acid (50 mg, 0.166 mmol) in DMF (2 mL) was added HATU (76 mg, 0.199 mmol). The reaction mixture was stirred at it for 5 min, followed by addition of 2-amino-1-(4-chlorophenyl)ethanone, HCl (37.6 mg, 0.183 mmol) and N-methylmorholine (0.1 mL, 0.7 mmol). The resulting mixture was stirred at rt for 3 h.

The reaction mixture was diluted with ethyl acetate and saturated NaHCO$_3$ solution. The organic layer was separated and washed with brine, 1 N HCl solution, brine and dried over MgSO$_4$. The filtrate was concentrated in vacuo. and the residue was purified by silica gel flash chromatography, eluting with 0-60% ethyl acetate in DCM to give Intermediate 43B (white solid, 48 mg, 0.106 mmol, 64% yield). LC-MS Anal. Calc'd for C$_{26}$H$_{26}$ClFN$_2$O$_2$ 452.17, found [M+H] 453.3. T$_r$=0.78 min (Method A). $^1$H NMR (400 MHz, CHLOROFORM-d) δ: 8.83 (d, J=4.6 Hz, 1H), 8.12 (dd, J=9.2, 5.7 Hz, 1H), 7.98-7.88 (m, 2H), 7.66 (dd, J=10.5, 2.8 Hz, 1H), 7.53-7.44 (m, 3H), 7.37 (d, J=4.6 Hz, 1H), 6.57 (t, J=4.0 Hz, 1H), 4.77 (d, J=4.4 Hz, 2H), 3.37-3.21 (m, 1H), 2.72-2.60 (m, 1H), 2.00-1.59 (m, 9H), 1.27-1.20 (m, 3H).

Example 43 5-(4-chlorophenyl)-2-((R)-1-((1s,4S)-4-(6-fluoroquinolin-4-yl)cyclohexyl)ethyl)oxazole The reaction mixture of (R)—N-(2-(4-chlorophenyl)-2-oxoethyl)-2-((1s,4S)-4-(6-fluoroquinolin-4-yl)cyclohexyl)

propanamide (20 mg, 0.044 mmol) in POCl₃ (0.1 mL, 1.073 mmol) was heated at 90° C. over night. The reaction mixture was cooled down, and concentrated in vacuo. and the residue was dissolved in MeOH, filtered, and purified via preparative HPLC to give Example 43 (10.7 mg, 0.025 mmol, 56% yield). LC-MS Anal. Calc'd for $C_{26}H_{24}ClFN_2O$ 434.16, found [M+H] 435.1 $T_r$=1.95 min (Method B). ¹H NMR (500 MHz, DMSO-d₆) δ: 8.82 (d, J=4.5 Hz, 1H), 8.09 (dd, J=9.1, 6.0 Hz, 1H), 7.98 (d, J=10.9 Hz, 1H), 7.70 (d, J=8.4 Hz, 2H), 7.68-7.63 (m, 1H), 7.62 (s, 1H), 7.59 (d, J=4.4 Hz, 1H), 7.52 (d, J=8.5 Hz, 2H), 3.43 (br. s., 1H), 2.07 (br. s., 1H), 1.98 (br. s., 1H), 1.91-1.58 (m, 7H), 1.34 (d, J=6.9 Hz, 3H), 1.29 (d, J=10.7 Hz, 1H).

Example 44

4-((1s,4s)-4-((R)-1-(5-(4-Chlorophenyl)-1H-imidazol-2-yl)ethyl)cyclohexyl)-6-fluoroquinoline

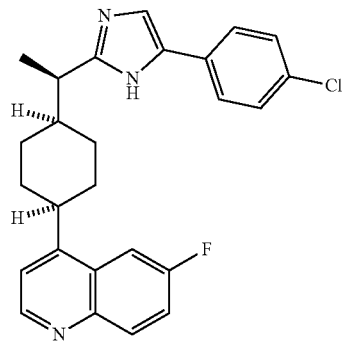 [SMILES: C[C@@H](c1ncc(-c2ccc(Cl)cc2)[nH]1)[C@H]1CC[C@@H](c2ccnc3ccc(F)cc32)CC1]

The reaction mixture of (R)—N-(2-(4-chlorophenyl)-2-oxoethyl)-2-((1s,4S)-4-(6-fluoroquinolin-4-yl)cyclohexyl)propanamide (20 mg, 0.044 mmol), ammonium acetate (68.1 mg, 0.883 mmol) in xylene (1 mL, 2.70 mmol) and acetic acid (0.253 mL, 4.42 mmol) was heated at 120° C. over night. The reaction mixture was cooled down and was extracted with ethyl acetate, dried over MgSO₄. The filtrate was concentrated in vacuo. and the residue was dissolved in MeOH, filtered, and purified via preparative HPLC to give example Example 44 as TFA salt (4.0 mg, 0.0073 mmol, 16.5% yield). LC-MS Anal. Calc'd for $C_{26}H_{25}ClFN_3$.TFA 433.17, found [M+H] 434.3. $T_r$=1.71 min (Method B). ¹H NMR (500 MHz, DMSO-d₆) δ: 8.87 (d, J=4.5 Hz, 1H), 8.14-8.10 (m, 2H), 8.00 (d, J=8.5 Hz, 1H), 7.81 (d, J=8.4 Hz, 2H), 7.69 (t, J=7.4 Hz, 1H), 7.64-7.55 (m, 3H), 3.68-3.40 (m, 1H), 2.17 (br. s., 1H), 2.08-1.68 (m, 7H), 1.59 (d, J=12.4 Hz, 1H), 1.41 (d, J=6.8 Hz, 3H), 1.06 (d, J=13.8 Hz, 1H).

Example 45

5-(4-Fluorophenyl)-2-((R)-1-((1s,4S)-4-(6-fluoroquinolin-4-yl)cyclohexyl)ethyl)oxazole

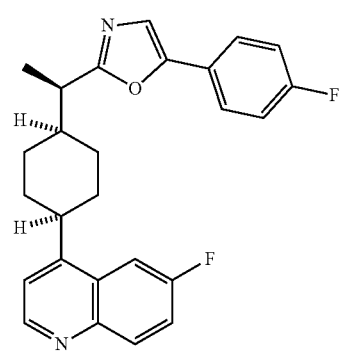 [SMILES: C[C@@H](c1ncc(-c2ccc(F)cc2)o1)[C@H]1CC[C@@H](c2ccnc3ccc(F)cc32)CC1]

Example 58 5-(4-fluorophenyl)-2-((R)-1-((1s,4S)-4-(6-fluoroquinolin-4-yl)cyclohexyl)ethyl)oxazole was prepared in a similar method as Example 43

The reaction mixture of (R)—N-(2-(4-fluorophenyl)-2-oxoethyl)-2-((1s,4S)-4-(6-fluoroquinolin-4-yl)cyclohexyl)propanamide (30 mg, 0.069 mmol) in POCl₃ (0.2 mL, 2.146 mmol) was heated at 100° C. for 2 h. The reaction mixture was concentrated in vacuo. and the residue was dissolved in MeOH, filtered, and purified via preparative HPLC to give Example 45 (21 mg, 0.050 mmol, 72% yield). LC-MS Anal. Calc'd for $C_{26}H_{24}F_2N_2O$ 418.19, found [M+H] 419.1. $T_r$=1.81 min (Method B). ¹H NMR (500 MHz, DMSO-d₆) δ: 8.78 (d, J=4.2 Hz, 1H), 8.06 (dd, J=8.8, 6.1 Hz, 1H), 7.92 (d, J=9.9 Hz, 1H), 7.73-7.66 (m, 2H), 7.63 (t, J=7.7 Hz, 1H), 7.55 (d, J=4.1 Hz, 1H), 7.47 (s, 1H), 7.26 (t, J=8.6 Hz, 2H), 3.80 (br. s., 1H), 2.02 (br. s., 1H), 1.94 (br. s., 1H), 1.87-1.55 (m, 7H), 1.30 (d, J=6.7 Hz, 3H), 1.22 (d, J=12.7 Hz, 1H).

Example 46

4-(2-((R)-1-((1s,4S)-4-(6-Fluoroquinolin-4-yl)cyclohexyl)ethyl)oxazol-5-yl)benzonitrile

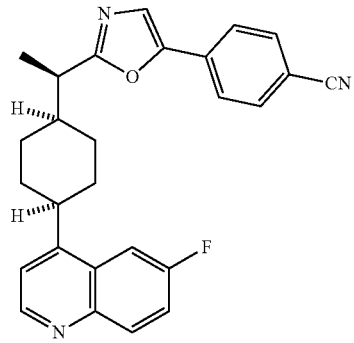 [SMILES: C[C@@H](c1ncc(-c2ccc(C#N)cc2)o1)[C@H]1CC[C@@H](c2ccnc3ccc(F)cc32)CC1]

Example 46 4-(2-((R)-1-((1s,4S)-4-(6-Fluoroquinolin-4-yl)cyclohexyl)ethyl)oxazol-5-yl)benzonitrile was prepared in a similar method as Example 43.

The reaction mixture of (R)—N-(2-(4-cyanophenyl)-2-oxoethyl)-2-((1s,4S)-4-(6-fluoroquinolin-4-yl)cyclohexyl)propanamide (18 mg, 0.041 mmol) in POCl₃ (0.2 mL, 2.146 mmol) was heated at 100° C. for 2 h. The reaction mixture was concentrated in vacuo. and the residue was dissolved in MeOH, filtered, and purified via preparative HPLC to give Example 46 (6.1 mg, 0.014 mmol, 35% yield). LC-MS Anal. Calc'd for $C_{27}H_{24}FN_3O$ 425.19, found [M+H] 426.1. $T_r$=1.66 min (Method B). ¹H NMR (500 MHz, DMSO-d₆) δ: 8.81 (d, J=4.4 Hz, 1H), 8.08 (dd, J=9.0, 5.9 Hz, 1H), 7.96 (d, J=8.8 Hz, 1H), 7.93-7.88 (m, 2H), 7.87-7.83 (m, 2H), 7.82 (s, 1H), 7.71-7.61 (m, 1H), 7.58 (d, J=4.4 Hz, 1H), 3.89 (s, 1H), 3.43-3.36 (m, 11H), 2.07 (d, J=10.6 Hz, 1H), 1.97 (br. s., 1H), 1.92-1.57 (m, 6H), 1.34 (d, J=6.8 Hz, 3H), 1.26 (d, J=12.0 Hz, 1H).

Example 47

6-Fluoro-4-((1S,4s)-4-((R)-1-(5-(4-fluorophenyl)-1H-imidazol-2-yl)ethyl)cyclohexyl)quinoline

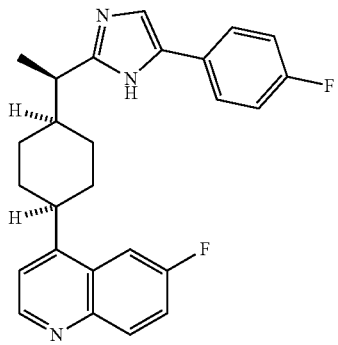 [SMILES: C[C@@H](c1ncc(-c2ccc(F)cc2)[nH]1)[C@H]1CC[C@@H](c2ccnc3ccc(F)cc32)CC1]

Example 47 was prepared in a similar method as Example 44.

The reaction mixture of (R)—N-(2-(4-fluorophenyl)-2-oxoethyl)-2-((1s,4S)-4-(6-fluoroquinolin-4-yl)cyclohexyl)propanamide (20 mg, 0.046 mmol), ammonium acetate (70.6 mg, 0.916 mmol) in xylene (1 mL, 2.70 mmol) and acetic acid (0.253 mL, 4.42 mmol) was heated at 120° C. over night. The reaction mixture was cooled down and was extracted with ethyl acetate, dried over MgSO$_4$. The filtrate was concentrated in vacuo. and the residue was dissolved in MeOH, filtered, and purified via preparative HPLC to give Example 47 (1.8 mg, 0.0043 mmol, 9.4% yield). LC-MS Anal. Calc'd for $C_{26}H_{29}F_2N_3$ 417.20, found [M+H] 418.4. T$_r$=1.29 min (Method B). $^1$H NMR (500 MHz, DMSO-d$_6$) δ: 8.80 (br. s., 1H), 8.07 (dd, J=8.9, 5.7 Hz, 1H), 7.93 (d, J=11.1 Hz, 1H), 7.78-7.70 (m, 2H), 7.67-7.61 (m, 1H), 7.57 (br. s., 1H), 7.41 (br. s., 1H), 7.14 (t, J=8.7 Hz, 2H), 3.71 (br. s., 1H), 3.39-3.20 (m, 1H), 2.12-1.43 (m, 8H), 1.25 (d, J=6.4 Hz, 3H), 1.20-1.09 (m, 1H).

Example 48

N-(1-((1s,4s)-4-(6-Fluoroquinolin-4-yl)cyclohexyl)propyl)-5-(4-methoxyphenyl)-1,3,4-oxadiazol-2-amine

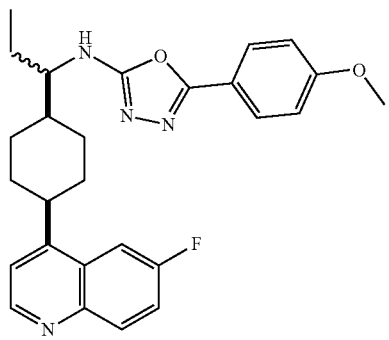

48A ethyl 2-(4-(6-fluoroquinolin-4-yl)cyclohex-3-en-1-yl)acetate

Ethyl 2-(4-(4,4,5,5-tetramethyl-1,3,2-dioxaborolan-2-yl)cyclohex-3-en-1-yl)acetate (Intermediate) (5 g, 17.00 mmol) was taken up in dioxane (28.3 ml) and water (7.08 ml). 4-chloro-6-fluoroquinoline (2.57 g, 14.15 mmol) was added followed by K$_2$CO$_3$ (5.87 g, 42.5 mmol). Mixture was bubble with nitrogen gas for 5 minutes before the addition of Pd(Ph$_3$P)$_4$ (0.327 g, 0.283 mmol). After addition, reaction was vacated and backfilled with N2 three times and then sealed (scaled vial parafilmed) and heated to 100° C. for 16 hours. The reaction was concentrated in vacuo and purified directly via silica gel flash column chromatography to give Intermediate 48A (4.22 g, 13.47 mmol, 95% yield). LC-MS Anal. Calc'd for $C_{19}H_{20}FNO_2$ 313.15, found [M+H] 314.1 T$_r$=0.75 min (Method A). $^1$H NMR (400 MHz, CHLOROFORM-d) δ: 8.80 (d, J=4.5 Hz, 1H), 8.10 (dd, J=9.2, 5.6 Hz, 1H), 7.60 (dd, J=10.1, 2.8 Hz, 1H), 7.46 (ddd, J=9.2, 8.0, 2.8 Hz, 1H), 7.19 (d, J=4.4 Hz, 1H), 5.82 (dd, J=2.9, 1.7 Hz, 1H), 4.19 (q, J=7.2 Hz, 2H), 2.61-2.16 (m, 6H), 2.08-1.96 (m, 2H), 1.59 (dtd, J=12.9, 10.6, 5.4 Hz, 1H), 1.36-1.26 (m, 3H).

48B. ethyl 2-(4-(6-fluoroquinolin-4-yl)cyclohexyl)acetate

Ethyl 2-(4-(6-fluoroquinolin-4-yl)cyclohex-3-en-1-yl)acetate (4.22 g, 13.47 mmol) was dissolved in MeOH (67.3 ml) and ammonium formate (4.25 g, 67.3 mmol) was added. The vessel was equipped with a reflux condenser and vacated and flushed with nitrogen gas 3 times. Then, palladium on carbon (0.143 g, 1.347 mmol) (wet, degussa type) was added and the reaction was heated to reflux for 1 hour. The reaction was cooled, concentrated in vacuo, and diluted with DCM. Solids were filtered off and the filtrate was concentrated to give crude Intermediate 48B (4.20 g, 13.32 mmol, 99% yield) as a mixture of cis- and trans-diastereomers. LC-MS Anal. Calc'd for $C_{19}H_{22}FNO_2$ 315.16, found [M+H] 316.2 T$_r$=0.76 min (Method A).

48C ethyl 2-(4-(6-fluoroquinolin-4-yl)cyclohexyl)butanoate

To the flask containing THF (6 mL) was added lithium diisopropylamide (2.0 M solution in THF) (3.17 mL, 6.34 mmol) at −78° C. followed by addition of 1,3-dimethyltetrahydropyrimidin-2(1H)-one (0.573 mL, 4.76 mmol) and a solution of ethyl 2-(4-(6-fluoroquinolin-4-yl)cyclohexyl)acetate (1.0 g, 3.17 mmol) in THF (10 mL) dropwise at −78° C. The resulting mixture turned into brown solution and stirred at −78° C. for 1 h, then iodoethane (0.51 mL, 6.34 mmol) was added slowly. The reaction mixture was then stirred at ice bath temperature for 1h, warmed to rt over night. The reaction was quenched by pouring into water and extracting with EtOAc. Combined organic layer was washed with brine, dried with MgSO$_4$, filtered and concentrated in vacuo. The residue was dissolved in DCM and purified by silica gel flash chromatography, eluting with 0-20% ethyl acetate in hexane to give Intermediate 48C (oil, 0.81 g, 2.359 mmol, 74.4% yield). LC-MS Anal. Calc'd for $C_{21}H_{26}FNO_2$, 343.19 found [M+H] 344.3. T$_r$=0.87-0.88 min (Method A). $^1$H NMR (400 MHz, CHLOROFORM-d) δ: 8.88-8.77 (m, 1H), 8.18-8.06 (m, 1H), 7.66 (dd, J=10.6, 2.6 Hz, 1H), 7.47 (ddd, J=9.2, 8.0, 2.9 Hz, 1H), 7.36 (d, J=4.6 Hz, 1H), 4.25-4.15 (m, 2H), 3.34-3.09 (m, 1H), 2.70-2.16 (m, 1H), 2.13-1.49 (m, 13H), 1.36-1.24 (m, 3H), 1.00-0.90 (m, 3H).

48D. 2-((1r,4r)-4-(6-fluoroquinolin-4-yl)cyclohexyl)butanoic acid

To a solution of ethyl 2-(4-(6-fluoroquinolin-4-yl)cyclohexyl)butanoate (0.81 g, 2.359 mmol) in THF (4 mL) and MeOH (7 mL) was added LiOH solution (7.1 mL, 14.2 mmol) slowly. The reaction mixture was stirred at rt over night. Next day, to the reaction mixture was added more LiOH solution (7.1 mL, 14.2 mmol) and the resulting reaction mixture was heated at 70° C. for 28 h. The reaction mixture was cooled down and to the mixture was added ethyl acetate. The aqueous layer was separated and to the aqueous layer was added 1 N HCl solution to adjust pH to 5-6. The resulting mixture was diluted with water and CHCl$_3$: 2-propanol (2:1). The organic layer was separated and dried over MgSO$_4$. The filtrate was concentrated in vacuo to give Intermediate 48D as a mixture of cis and trans (3:2) isomer (0.64 g, 2.029 mmol, 86% yield). LC-MS Anal. Calc'd for $C_{19}H_{22}FNO_2$ 315.16 found [M+H] 316.3. $T_r$=0.72 min (Method A). $^1$H NMR (400 MHz, CHLOROFORM-d) δ: 8.83 (d, J=4.4 Hz, 1H), 8.30-8.03 (m, 1H), 7.67 (dd, J=10.6, 2.4 Hz, 1H), 7.48 (ddd, J=9.2, 7.9, 2.6 Hz, 1H), 7.38 (d, J=4.6 Hz, 1H), 7.32-7.27 (m, 1H), 3.37-3.07 (m, 1H), 2.77-2.21 (m, 1H), 2.11-1.30 (m, 11H), 1.07-1.00 (m, 3H)

48E 6-fluoro-4-(4-(1-isocyanatopropyl)cyclohexyl)quinoline

To a suspension of 2-(4-(6-fluoroquinolin-4-yl)cyclohexyl)butanoic acid (150 mg, 0.476 mmol) in toluene (4 mL) were added diphenylphosphoryl azide (0.12 mL, 0.55 mmol) and TEA (0.09 mL, 0.62 mmol). The reaction mixture in a sealed vial turned into clear solution after addition of TEA. The vial was sealed and heated to 70° C. for 2 h. The reaction was cooled to rt. and concentrated under reduced pressure. The crude was used in the next step reaction. LC-MS Anal. Calc'd for $C_{19}H_{21}FN_2O$ 312.16, found [M+H] 313.3. $T_r$=0.90 min (Method A).

48F. N-(1-((1s,4s)-4-(6-fluoroquinolin-4-yl)cyclohexyl)propyl)-2-(4-methoxybenzoyl)hydrazinecarboxamide To a suspension of 6-fluoro-4-(4-(1-isocyanatopropyl)cyclohexyl)quinoline (75 mg, 0.240 mmol) in THF (2 mL) was added 4-methoxybenzohydrazide, HCl (58.4 mg, 0.288 mmol) and TEA (0.17 mL, 1.20 mmol). The reaction mixture was stirred at rt for 1 h. The reaction mixture was quenched with MeOH and concentrated in vacuo. and the residue was dissolved in MeOH, filtered, and purified via preparative HPLC to give major isomer Intermediate 48F as TFA salt (76 mg, 0.128 mmol, 53.4% yield). LC-MS Anal. Calc'd for $C_{27}H_{31}FN_4O_3$.TFA, 478.24 found [M+H] 479.3 $T_r$=0.75 min (Method A). $^1$H NMR (400 MHz, METHANOL-d$_4$) δ: 9.01 (d, J=5.7 Hz, 1-), 8.39-8.19 (m, 2H), 8.07 (d, J=5.7 Hz, 1H), 7.86 (d, J=8.8 Hz, 2H), 7.35-7.14 (m, 2H), 6.99 (d, J=8.8 Hz, 2H), 4.25-3.98 (m, 11H), 3.88-3.80 (m, 3H), 3.66 (d, J=6.6 Hz, 1H), 2.30-1.61 (m, 10H), 1.46-1.23 (m, 1H), 1.11-0.96 (m, 3H)

Example 48 N-(1-((1s,4s)-4-(6-Fluoroquinolin-4-yl)cyclohexyl)propyl)-5-(4-methoxyphenyl)-1,3,4-oxadiazol-2-amine The reaction mixture of N-(1-((1s,4s)-4-(6-fluoroquinolin-4-yl)propyl)-2-(4-methoxybenzoyl)hydrazinecarboxamide, TFA (50 mg, 0.084 mmol) in POCl$_3$ (0.2 mL, 2.146 mmol) was heated at 95° C. for 2 h. The reaction mixture was concentrated in vacuo and the residue was dissolved in MeOH, filtered, and purified via preparative HPLC to give example Example 48 (23 mg, 0.050 mmol, 59.2% yield). LC-MS Anal. Calc'd for $C_{27}H_{29}FN_4O_2$ 460.22, found [M+H] 461.0; $T_r$=1.42 min (Method B). $^1$H NMR (500 MHz, DMSO-d$_6$) δ: 8.80 (d, J=4.5 Hz, 1H), 8.07 (dd, J=9.1, 5.8 Hz, 1H), 7.93 (d, J=10.9 Hz, 1H), 7.73 (d, J=8.7 Hz, 2H), 7.68-7.55 (m, 2H), 7.51 (d, J=4.5 Hz, 1H), 7.06 (d, J=8.8 Hz, 2H), 3.79 (s, 1H), 3.64 (s, 3H), 3.39 (br. s., 1H), 1.91-1.56 (m, 10H), 1.51-1.35 (m, 1H), 0.90 (t, J=7.2 Hz, 3H)

Example 49

N-(1-((1s,4s)-4-(6-Fluoroquinolin-4-yl)cyclohexyl)propyl)-5-(4-methoxyphenyl)-1,3,4-oxadiazol-2-amine (absolute stereochemistry not determined)

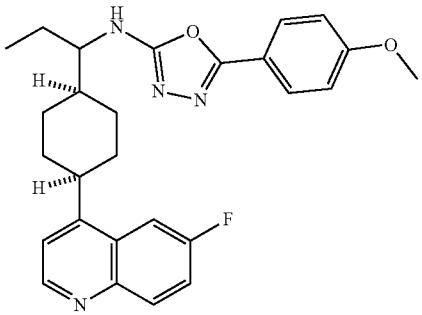 [SMILES: CCC(Nc1nnc(-c2ccc(OC)cc2)o1)[C@H]1CC[C@@H](c2ccnc3ccc(F)cc32)CC1]

Stereoisomer separation was developed as described in Method D. Approximately 15 mg sample was resolved. The fractions ("Peak-1" and "Peak-2") were collected in MeOH and concentrated in vacuo, lyophilized to give two isolates. Example 49-1, enantiomer 1, $T_r$=9.36 min over 30 min run (Method H). Example 2, enantiomer 2 $T_r$=11.12 min over 30 min (absolute stereochemistry was not determined).

First eluant, Example 49-1 (4.5 mg, 0.0097 mmol, 37.1% yield). LC-MS Anal. Calc'd for $C_{27}H_{29}FN_4O_2$ 460.23, found [M+H] 461.4, $T_r$=0.79 min (Method A). $^1$H NMR (400 MHz, METHANOL-d$_4$) δ: 8.77 (d, J=4.6 Hz, 1H), 8.07 (dd, J=9.2, 5.5 Hz, 1H), 7.88 (dd, J=10.7, 2.8 Hz, 1H), 7.84-7.76 (m, 2H), 7.63 (d, J=4.6 Hz, 1H), 7.58 (ddd, J=9.2, 8.1, 2.8 Hz, 1H), 7.05 (d, J=8.8 Hz, 2H), 4.12-3.91 (m, 1H), 3.88-3.82 (m, 3H), 3.54-3.39 (m, 1H), 2.18-1.72 (m, 10H), 1.64-1.46 (m, 1H), 1.02 (t, J=7.3 Hz, 3H)

Second eluant, Example 49-2 (4.5 mg, 0.0097 mmol, 37.1% yield). LC-MS Anal. Calc'd for $C_{27}H_{29}FN_4O_2$ 460.23, found [M+H] 461.4, $T_r$=0.79 min (Method A). $^1$H NMR (400 MHz, METHANOL-d$_4$) δ: 8.77 (d, J=4.6 Hz, 1H), 8.07 (dd, J=9.4, 5.6 Hz, 1H), 7.87 (dd, J=10.8, 2.6 Hz, 1H), 7.84-7.78 (m, 2H), 7.63 (d, J=4.6 Hz, 1H), 7.58 (ddd, J=9.2, 8.1, 2.8 Hz, 1H), 7.12-6.97 (m, 2H), 4.05-3.93 (m, 1H), 3.86 (s, 3H), 3.57-3.38 (m, 1H), 2.09-1.73 (m, 10H), 1.54 (dt, J=14.9, 7.4 Hz, 1H), 1.02 (t, J=7.4 Hz, 3H)

Example 50

N-(1-((1r,4r)-4-(6-Fluoroquinolin-4-yl)cyclohexyl)propyl)-5-(4-methoxyphenyl)-1,3,4-oxadiazol-2-amine

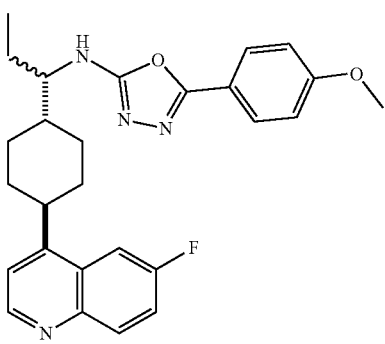

Example 50 was prepared in a similar method as Example 48 using the minor Intermediate 48F of Example 48

The reaction mixture of N-(1-(4-(6-fluoroquinolin-4-yl)cyclohexyl)propyl)-2-(4-methoxybenzoyl)hydrazinecarboxamide, TFA (36 mg, 0.061 mmol) in $POCl_3$ (0.2 mL, 2.146 mmol) was heated at 100° C. for 2 h. The reaction mixture was concentrated in vacuo and the residue was dissolved in MeOH, filtered, and purified via preparative HPLC to give Example 50 (10.2 mg, 0.022 mmol, 35.8% yield). LC-MS Anal. Calc'd for $C_{27}H_{29}FN_2O_2$ 460.22, found [M+H] 461.0 $T_r$=1.39 min (Method B). $^1$H NMR (500 MHz, DMSO-$d_6$) δ: 8.78 (d, J=4.4 Hz, 1H), 8.07 (dd, J=8.9, 5.8 Hz, 1H), 7.96 (d, J=9.0 Hz, 1H), 7.75 (d, J=8.7 Hz, 2H), 7.68-7.53 (m, 2H), 7.44 (d, J=4.4 Hz, 1H), 7.08 (d, J=8.6 Hz, 2H), 3.81 (s, 3H), 3.44 (br. s., 1H), 3.27 (br. s., 1H), 2.00-1.81 (m, 4H), 1.74-1.36 (m, 7H), 0.92 (t, J=7.2 Hz, 3H).

Example 51

6-Fluoro-4-(4-(1-(5-(4-isopropoxyphenyl)-4H-1,2,4-triazol-3-yl)propyl)cyclohexyl)quinoline

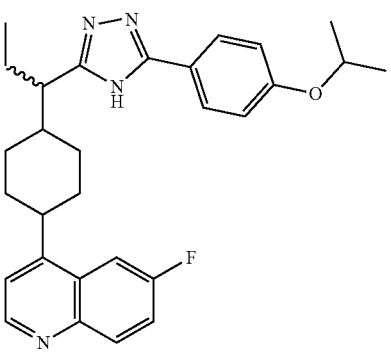 [SMILES: CCC(c1nnc(-c2ccc(OC(C)C)cc2)[nH]1)C1CCC(c2ccnc3ccc(F)cc23)CC1]

51A. tert-butyl 2-(2-((1s,4s)-4-(6-fluoroquinolin-4-yl)cyclohexyl)butanoyl)hydrazinecarboxylate To a solution of 2-(4-(6-fluoroquinolin-4-yl)cyclohexyl)butanoic acid (170 mg, 0.539 mmol) in DMF (3 mL) was added HATU (246 mg, 0.647 mmol) and the reaction mixture was stirred at rt for 5 min, followed by addition of tert-butyl carbazate (85 mg, 0.647 mmol) and DIPEA (0.15 mL, 0.862 mmol). The resulting mixture was stirred at rt for 2 h. The reaction mixture was diluted with ethyl acetate and saturated $NaHCO_3$ solution. The organic layer was separated and washed with brine, dried over $MgSO_4$. The filtrate was concentrated in vacuo. The residue was dissolved in DCM, purified by flash silica gel column chromatography, eluting with 0 to 40% of (10% MeOH in DCM) to give major isomer Intermediate 51A (white solid, 125 mg, 0.291 mmol, 54% yield). LC-MS Anal. Calc'd for $C_{24}H_{32}FN_3O_3$ 429.24 found [M+H] 430.4. $T_r$=0.72 min (Method A). $^1$H NMR (400 MHz, CHLOROFORM-d) δ: 8.98-8.81 (m, 1H), 8.71 (t, J=4.6 Hz, 1H), 8.12 (dd, J=9.0, 5.5 Hz, 1H), 7.73-7.56 (m, 1H), 7.52-7.38 (m, 1H), 7.22 (t, J=5.1 Hz, 1H), 6.94-6.72 (m, 1H), 3.25 (br. s., 1H), 3.15-2.89 (m, 1H), 2.58-2.33 (m, 1H), 2.17-1.54 (m, 10H), 1.44 (d, J=2.4 Hz, 9H), 1.01 (t, J=7.4 Hz, 3H)

51B. 2-(4-(6-fluoroquinolin-4-yl)cyclohexyl)butanehydrazide

To a solution of tert-butyl 2-(2-(4-(6-fluoroquinolin-4-yl)cyclohexyl)butanoyl)hydrazinecarboxylate (125 mg, 0.291 mmol) in DCM (1.0 mL) was added HCl (4.0 M solution in dioxane) (1.09 mL, 4.37 mmol). The reaction mixture was stirred at rt for 1 h. White solid crashed out. The mixture was concentrated in vacuo to give Intermediate 51B as 2.HCl salt (white solid, 117 mg, 0.291 mmol, 100% yield). LC-MS Anal. Calc'd for $C_{19}H_{24}FN_3O_2$.HCl 329.19, found [M+H] 330.3. $T_r$=0.64 min (Method A). $^1$H NMR (400 MHz, DMSO-$d_6$&) δ: 11.33 (s, 1H), 9.08 (d, J=4.8 Hz, 1H), 8.30 (dd, J=9.2, 5.3 Hz, 1H), 8.23 (d, J=8.1 Hz, 1H), 7.99-7.83 (m, 2H), 3.55-3.45 (m, 1H), 2.83-2.70 (m, 1H), 2.07-1.53 (m, 10H), 1.51-1.33 (m, 1H), 0.88 (t, J=7.4 Hz, 3H)

Example 51 6-fluoro-4-(4-(1-(5-(4-isopropoxyphenyl)-4H-1,2,4-triazol-3-yl)propyl)cyclohexyl)quinoline The reaction mixture of 4-(propan-2-yloxy)benzene-1-carboximidamide (23.04 mg, 0.129 mmol), and 2-(4-(6-fluoroquinolin-4-yl)cyclohexyl)butanehydrazide, 2 HCl (40 mg, 0.099 mmol) in pyridine (1 mL) and TEA (0.055 mL, 0.398 mmol) (0.1 mL) in a sealed tube was purged with nitrogen stream and heated at 120° C. over night. The reaction mixture was then heated at 135° C. for another 3 h. The reaction mixture was diluted with ethyl acetate and $NH_4Cl$ solution. The organic layer was separated and concentrated in vacuo. and the residue was dissolved in MeOH, filtered, and purified via preparative HPLC to give Example 51 (13.8 mg, 0.028 mmol, 28% yield). LC-MS Anal. Calc'd for $C_{29}H_{33}FN_4O$ 472.26, found [M+H] 473.0. $T_r$=1.45 min (Method B). $^1$H NMR (400 MHz, DMSO-$d_6$) δ: 8.84 (d, J=4.4 Hz, 1H), 8.09 (dd, J=9.1, 5.9 Hz, 1H), 7.97 (d, J=8.8 Hz, 1H), 7.89 (d, J=8.5 Hz, 2H), 7.72-7.62 (m, 1H), 7.56 (d, J=4.2 Hz, 1H), 6.97 (d, J=8.2 Hz, 2H), 4.79-4.49 (m, 1H), 2.22-1.95 (m, 2H), 1.92-1.46 (m, 9H), 1.27 (d, J=5.9 Hz, 6H), 1.23-1.09 (m, 2H), 0.73 (t, J=7.2 Hz, 3H)

Example 52

2-(1-(4-(6-Fluoroquinolin-4-yl)cyclohexyl)propyl)-5-(4-isopropoxyphenyl)-1,3,4-oxadiazole

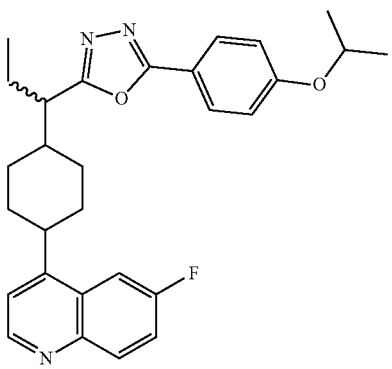 [SMILES: CCC(c1nnc(-c2ccc(OC(C)C)cc2)o1)C1CCC(c2ccnc3ccc(F)cc23)CC1]

The reaction mixture of 4-(propan-2-yloxy)benzene-1-carboximidamide (23.04 mg, 0.129 mmol), and 2-(4-(6-fluoroquinolin-4-yl)cyclohexyl)butanehydrazide, 2 HCl (40 mg, 0.099 mmol) in pyridine (1 mL) and TEA (0.055 mL, 0.398 mmol) (0.1 mL) in a sealed tube was purged with nitrogen stream and heated at 120° C. overnight. The reaction mixture was then heated at 135° C. for another 3 h. The reaction mixture was diluted with ethyl acetate and NH₄Cl solution. The organic layer was separated and concentrated in vacuo. and the residue was dissolved in MeOH, filtered, and purified via preparative HPLC to give another compound Example 52 (4.6 mg, 0.0097 mmol, 9.7% yield). LC-MS Anal. Calc'd for $C_{29}H_{32}FN_3O_2$, 473.25, found [M+H] 474.3. $T_r$=2.01 min (Method B). ¹H NMR (400 MHz, DMSO-d₆) δ: 8.81 (d, J=4.4 Hz, 1H), 8.08 (dd, J=9.0, 5.9 Hz, 1H), 7.95 (d, J=9.1 Hz, 1H), 7.92-7.78 (m, 2H), 7.65 (t, J=7.6 Hz, 1H), 7.58 (d, J=4.3 Hz, 1H), 7.09 (d, J=8.7 Hz, 2H), 4.72 (d, J=11.8, 5.9 Hz, 1H), 3.53-3.40 (m, 1H), 2.15 (br. s., 1H), 2.04-1.54 (m, 9H), 1.28 (d, J=5.9 Hz, 6H), 1.21 (br. s., 2H), 0.81 (t, J=7.2 Hz, 3H)

Example 53

6-Fluoro-4-(4-(1-(5-(4-isopropoxyphenyl)-4H-1,2,4-triazol-3-yl)propyl)cyclohexyl)quinoline

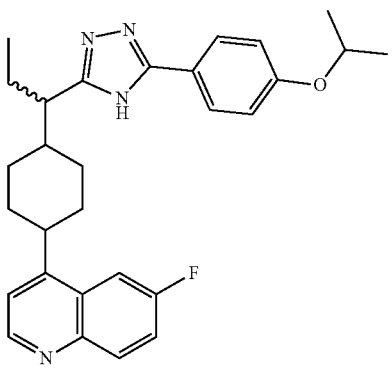 [SMILES: CCC(c1nnc(-c2ccc(OC(C)C)cc2)o1)C1CCC(c2ccnc3ccc(F)cc23)CC1]

Example 53 6-fluoro-4-(4-(1-(5-(4-isopropoxyphenyl)-4H-1,2,4-triazol-3-yl)propyl)cyclohexyl)quinoline was prepared in a similar method as Example 51 using the minor isomer Intermediate 51B of Example 51.

The reaction mixture of 4-(propan-2-yloxy)benzene-1-carboximidamide (18.43 mg, 0.103 mol), and 2-(4-(6-fluoroquinolin-4-yl)cyclohexyl)butanehydrazide, 2 HCl (32 mg, 0.080 mmol) in pyridine (1 mL) and TEA (0.044 mL, 0.318 mmol) (0.1 mL) in a sealed tube was purged with nitrogen stream and heated at 130° C. over night. The reaction mixture was concentrated in vacuo and the residue was dissolved in MeOH, filtered, and purified via preparative HPLC to give Example 53 (7.5 mg, 0.016 mmol, 19.8% yield). LC-MS Anal. Calc'd for $C_{29}H_{33}FN_4O$, 472.26 found [M+H] 473.2 $T_r$=1.38 min (Method B). ¹H NMR (500 MHz, DMSO-d₆) δ: 8.77 (d, J=4.0 Hz, 1H), 8.14-8.00 (m, 1H), 7.97-7.82 (m, 3H), 7.63 (t, J=7.7 Hz, 1H), 7.42 (d, J=4.0 Hz, 1H), 6.98 (d, J=6.0 Hz, 2H), 4.65 (br. s., 1H), 3.53 (br. s., 1H), 3.34-3.09 (m, 1H), 2.12-1.67 (m, 61H), 1.62-1.41 (m, 3H), 1.37-1.21 (m, 8H), 0.74 (t, J=6.9 Hz, 3H).

Example 54

2-(1-(4-(6-Fluoroquinolin-4-yl)cyclohexyl)propyl)-5-(4-isopropoxyphenyl)-1,3,4-oxadiazole

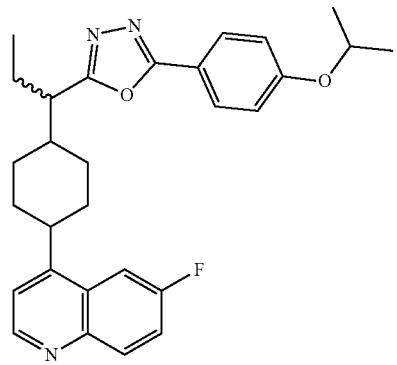

Example 54 2-(1-(4-(6-Fluoroquinolin-4-yl)cyclohexyl)propyl)-5-(4-isopropoxyphenyl)-1,3,4-oxadiazole The reaction mixture of 4-(propan-2-yloxy)benzene-1-carboximidamide (18.4 mg, 0.103 mmol), and the minor isomer intermediate 2-(4-(6-fluoroquinolin-4-yl)cyclohexyl)butanehydrazide, 2 HCl (32 mg, 0.080 mmol) in pyridine (1 mL) and TEA (0.055 mL, 0.398 mmol) (0.1 mL) in a sealed tube was purged with nitrogen stream and heated at 120° C. over night. The reaction mixture was then heated at 135° C. for another 3 h. The reaction mixture was diluted with ethyl acetate and NH₄Cl solution. The organic layer was separated and concentrated in vacuo. and the residue was dissolved in MeOH, filtered, and purified via preparative HPLC to give another compound Example 54 (10.6 mg, 0.017 mmol, 21.8% yield). LC-MS Anal. Calc'd for $C_{29}H_{32}FN_3O_2$, 473.25, found [M+H] 474. $T_r$=1.84 min (Method B). ¹H NMR (400 MHz, DMSO-d₆) δ: 8.80 (d, J=4.4 Hz, 1H), 8.07 (dd, J=8.8, 5.7 Hz, 1H), 7.97 (d, J=9.6 Hz, 1H), 7.91 (d, J=8.5 Hz, 2H), 7.65 (t, J=7.5 Hz, 1H), 7.45 (d, J=4.4 Hz, 1H), 7.11 (d, J=8.6 Hz, 2H), 4.82-4.63 (m, 1H), 3.34-3.20 (m, 1H), 2.91 (br. s., 1H), 2.03-1.78 (m, 6H), 1.73-1.47 (m, 3H), 1.40 (br. s., 2H), 1.29 (d, J=5.9 Hz, 6H), 0.85 (t, J=7.1 Hz, 3H).

Example 55

5-(1-(4-(6-Fluoroquinolin-4-yl)cyclohexyl)propyl)-N-(4-methoxyphenyl)-4H-1,2,4-triazol-3-amine

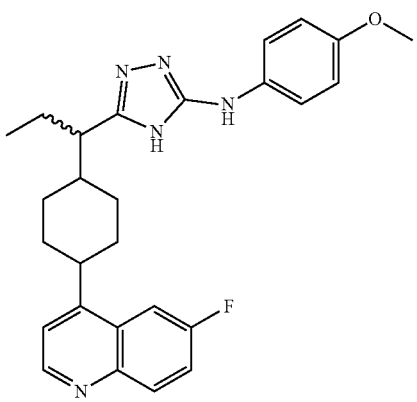 [SMILES: CCC(c1nnc(Nc2ccc(OC)cc2)[nH]1)C1CCC(c2ccnc3ccc(F)cc23)CC1]

The reaction mixture of methyl (4-methoxyphenyl)carbamimidothioate, iodide salt (47.0 mg, 0.145 mmol), and the major isomer intermediate 2-(4-(6-fluoroquinolin-4-yl)cyclohexyl)butanehydrazide, 2 HCl (45 mg, 0.112 mmol) in pyridine (1 mL) and TEA (0.1 mL, 0.68 mmol) in a sealed tube was purged with nitrogen and then heated at 120° C. for 20 h. The reaction mixture was cooled down and diluted with ethyl acetate and NH$_4$Cl solution. The organic layer was concentrated in vacuo and the residue was dissolved in MeOH, filtered, and purified via preparative HPLC to give example Example 55 (8.3 mg, 0.018 mmol, 15.7% yield). LC-MS Anal. Calc'd for C$_{27}$H$_{30}$FN$_5$O 459.24, found [M+H] 460.0. T$_r$=1.13 min (Method B). $^1$H NMR (500 MHz, DMSO-d$_6$) δ: 8.83 (br. s., 1H), 8.71 (br. s., 1H), 8.08 (dd, J=9.0, 5.8 Hz, 1H), 7.95 (d, J=9.8 Hz, 1H), 7.65 (t, J=7.5 Hz, 1H), 7.53 (d, J=3.8 Hz, 1H), 7.42 (d, J=8.2 Hz, 2H), 6.79 (d, J=8.2 Hz, 2H), 3.71-3.42 (m, 3H), 2.99 (br. s., 1H), 2.11-1.44 (m, 10H), 1.21 (br. s., 2H), 0.74 (t, J=7.1 Hz, 3H)

Example 56

5-(1-(4-(6-Fluoroquinolin-4-yl)cyclohexyl)propyl)-N-(4-methoxyphenyl)-4H-1,2,4-triazol-3-amine

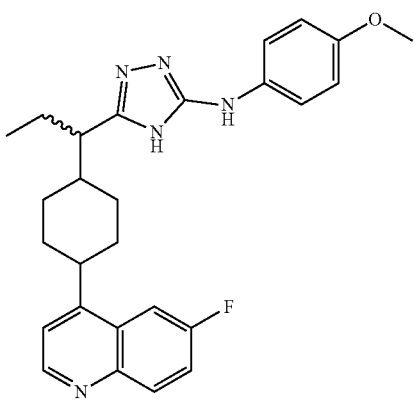 [SMILES: CCC(c1nnc(Nc2ccc(OC)cc2)[nH]1)C1CCC(c2ccnc3ccc(F)cc23)CC1]

The reaction mixture of methyl (4-methoxyphenyl)carbamimidothioate, iodide salt (39.7 mg, 0.123 mmol), and the minor isomer intermediate 2-(4-(6-fluoroquinolin-4-yl)cyclohexyl)butanehydrazide, 2 HCl (38 mg, 0.094 mmol) in pyridine (1 mL) and TEA (0.1 mL, 0.68 mmol) in a sealed tube was purged with nitrogen and then heated at 120° C. for 20 h. The reaction mixture was cooled down and diluted with ethyl acetate and NH$_4$Cl solution. The organic layer was concentrated in vacuo and the residue was dissolved in MeOH, filtered, and purified via preparative HPLC to give example Example 56 (7.7 mg, 0.016 mmol, 16.5% yield). LC-MS Anal. Calc'd for C$_{27}$H$_{30}$FN$_5$O 459.24, found [M+H] 460.2. T$_r$=1.09 min (Method B). $^1$H NMR (500 MHz, DMSO-d$_6$) δ: 8.79 (d, J=4.5 Hz, 1H), 8.07 (dd, J=9.1, 5.9 Hz, 1H), 7.96 (d, J=8.7 Hz, 1H), 7.76-7.60 (m, 1H), 7.51-7.37 (m, 3H), 6.81 (d, J=8.8 Hz, 2H), 3.68 (s, 3H), 3.33-3.18 (m, 1H), 2.10-1.66 (m, 6H), 1.64-1.43 (m, 3H), 1.41-1.27 (m, 2H), 1.22 (s, 1H), 0.77 (t, J=7.2 Hz, 3H).

Example 57

N-(2-Ethoxy-1-((1s,4s)-4-(2-fluoro-3-methylpyridin-4-yl)cyclohexyl)ethyl)-5-(4-methoxyphenyl)-1,3,4-oxadiazol-2-amine (absolute stereochemistry not determined)

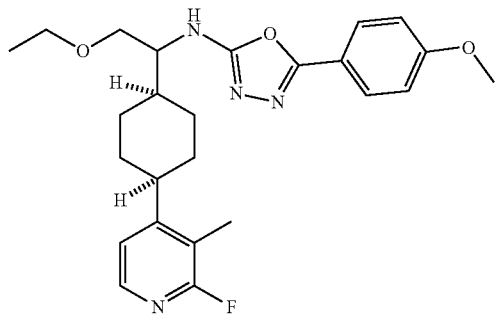 [SMILES: CCOCC(Nc1nnc(-c2ccc(OC)cc2)o1)[C@H]1CC[C@@H](c2ccnc(F)c2C)CC1]

57A. Ethyl 3-ethoxy-2-(4-(2-fluoro-3-methylpyridin-4-yl)cyclohex-3-enyl)propanoate To a flask containing THF (15 mL) was added LDA (1.5 M solution in cyclohexane) (16.7 mL, 24.99 mmol) at −78° C., followed by addition of a solution of ethyl 2-(4-(2-fluoro-3-methylpyridin-4-yl)cyclohex-3-en-1-yl)acetate (63B) (3.3 g, 11.90 mmol) in THF (8 mL) dropwise at −78° C. and DMPU (2.2 mL, 17.9 mmol). The resulting mixture was stirred at −78° C. for 1.5 h, then chloromethyl ethyl ether (2.3 mL, 23.80 mmol) was added. The reaction mixture was stirred at −78° C., then gradually warmed up for 3 h. The reaction mixture was quenched with NH$_4$Cl aqueous solution. The resulting mixture was extracted with ethyl acetate two times. The organic layers were combined, washed with brine, dried over MgSO$_4$. The filtrate was concentrated in vacuo. The extract was purified via silica gel flash column chromatography, eluting with 0-20% ethyl acetate in hexane to give Intermediate 57A (oil, 1.8 g, 5.37 mmol, 45.1% yield). LC-MS Anal. Calc'd for C$_{19}$H$_{26}$FNO$_3$, 335.19 found [M+H] 336.3. T$_r$=1.05 min (Method A). $^1$H NMR (400 MHz, CHLOROFORM-d) δ: 7.94 (d, J=5.1 Hz, 1H), 6.87 (dd, J=5.1, 0.7 Hz, 1H), 5.73-5.49 (m, 1H), 4.31-4.12 (m, 2H), 3.79-3.60 (m, 2H), 3.58-3.38 (m, 2H), 2.76-2.57 (m, 1H), 2.42-2.14 (m, 6H), 2.11-1.81 (m, 3H), 1.54-1.41 (m, 1H), 1.35-1.25 (m, 3H), 1.19 (td, J=6.9, 1.3 Hz, 3H).

57B. Ethyl 3-ethoxy-2-((1s,4s)-4-(2-fluoro-3-methylpyridin-4-yl)cyclohexyl)propanoate The solution of ethyl 3-ethoxy-2-(4-(2-fluoro-3-methylpyridin-4-yl)cyclohex-3-en-1-yl)propanoate (1.8 g, 5.37 mmol) in MeOH (40 mL) was evacuated, then under nitrogen stream were added ammonium formate (1.69 g, 26.8 mmol) and Pd—C (0.571 g, 0.537 mmol) (10% wt. wet) at rt. The resulting mixture was heated at 80° C. for 5 h. After heating, lots of bubbles formed. The reaction mixture was cooled down and filtered through a celite pad. The filtrate was concentrated in vacuo. The residue was extracted with ethyl acetate two times. The organic layers were combined, washed with brine, dried over $MgSO_4$. The filtrate was concentrated in vacuo. The mixture was further purified by SFC to give two fractions. The major fraction was concentrated in vacuo to give the title compound Intermediate 57B as a cis isomer (oil, 0.76 g, 2.25 mmol, 42%). LC-MS Anal. Calc'd for $C_{19}H_{28}FNO_3$, 337.21 found [M+H] 338.2. $T_r$=1.04 min (Method A). $^1$H NMR (400 MHz, CHLOROFORM-d) δ: 7.99 (d, J=5.3 Hz, 1H), 7.06 (d, J=5.3 Hz, 1H), 4.30-4.17 (m, 2H), 3.71-3.40 (m, 4H), 3.06 (ddd, J=11.2, 9.0, 5.5 Hz, 1H), 2.89-2.73 (m, 1H), 2.23 (d, J=1.1 Hz, 3H), 2.06 (dt, J=11.0, 3.4 Hz, 1H), 1.90-1.57 (m, 8H), 1.28 (t, J=7.2 Hz, 3H), 1.19 (t, J=7.0 Hz, 3H).

57C. 3-Ethoxy-2-((1s,4s)-4-(2-fluoro-3-methylpyridin-4-yl)cyclohexyl)propanoic acid To a solution of ethyl 3-ethoxy-2-((1s,4s)-4-(2-fluoro-3-methylpyridin-4-yl)cyclohexyl)propanoate (0.72 g, 2.134 mmol) in THF (10 mL) and MeOH (4 mL) was added LiOH solution (2 M) (10.7 mL, 21.34 mmol). The resulting mixture was heated at 45° C. for 5.5 h. The reaction mixture was cooled down and to the reaction mixture was added 1 N HCl solution to adjust pH to about 5. White solid precipitated out. The resulting mixture was extracted with ethyl acetate. The organic layer was dried over $MgSO_4$. The filtrate was concentrated in vacuo to give Intermediate 57C as viscous solid (white solid, 0.6 g, 1.94 mmol, 91%). LC-MS Anal. Calc'd for $C_{17}H_{24}FNO_3$ 309.17, found [M+H]310.2. $T_r$=0.86 min (Method A). $^1$H NMR (400 MHz, METHANOL-d$_4$) δ: 8.00-7.93 (m, 1H), 7.25 (d, J=5.3 Hz, 1H), 3.79-3.41 (m, 4H), 3.04 (ddd, J=11.1, 9.3, 4.7 Hz, 1H), 2.98-2.85 (m, 1H), 2.25 (s, 3H), 2.01 (br. s., 1H), 1.93-1.48 (m, 8H), 1.17 (t, J=7.0 Hz, 3H).

57D. N-(2-ethoxy-1-((1s,4s)-4-(2-fluoro-3-methylpyridin-4-yl)cyclohexyl)ethyl)-2-(4-methoxybenzoyl)hydrazinecarboxamide To a suspension of crude 3-ethoxy-2-(4-(2-fluoro-3-methylpyridin-4-yl)cyclohexyl)propanoic acid (0.38 g, 1.228 mmol) in Toluene (10 mL) were added diphenylphosphoryl azide (0.32 mL, 1.47 mmol) and TEA (0.34 mL, 2.46 mmol). The reaction mixture in a sealed vial turned into clear solution after addition of TEA. The reaction mixture was heated to 70° C. for 2 h. The reaction was cooled to rt. The reaction mixture was concentrated under reduced pressure. To a solution of a portion of the crude intermediate 4-((1s,4s)-4-(2-ethoxy-1-isocyanatoethyl)cyclohexyl)-2-fluoro-3-methylpyridine (50 mg, 0.163 mmol) in THF (3 mL) was added 4-methoxybenzohydrazide, HCl (49.6 mg, 0.245 mmol) and DIPEA (0.11 mL, 0.65 mmol). The reaction mixture was stirred at rt for 3 h. The reaction mixture was concentrated in vacuo. The residue was dissolved in MeOH, filtered, and purified via preparative HPLC to give Intermediate 57D as TFA salt (white solid, 60 mg, 0.102 mmol, 62.7%). LC-MS Anal. Calc'd for $C_{25}H_{13}FN_4H_4$.TFA, 472.5, found [M+H] 473.2. $T_r$=0.88 min (Method A). $^1$H NMR (400 MHz, METHANOL-d$_4$) δ: 7.98-7.78 (m, 3H), 7.51-7.35 (m, 1H), 7.31-7.17 (m, 3H), 6.99 (d, J=8.8 Hz, 2H), 4.24 (d, J=10.8 Hz, 1H), 3.84 (s, 3H), 3.64 (d, J=3.5 Hz, 1H), 3.56-3.42 (m, 2H), 3.05-2.83 (m, 1H), 2.24 (s, 3H), 2.09-1.44 (m, 9H), 1.16 (d, J=13.9 Hz, 3H)

Example 57, Two isomers N-(2-Ethoxy-1-((1s,4s)-4-(2-fluoro-3-methylpyridin-4-yl)cyclohexyl)ethyl)-5-(4-methoxyphenyl)-1,3,4-oxadiazol-2-amine The reaction mixture of N-(2-ethoxy-1-((1s,4s)-4-(2-fluoro-3-methylpyridin-4-yl)cyclohexyl)ethyl)-2-(4-methoxybenzoyl)hydrazinecarboxamide, TFA (60 mg, 0.102 mmol) in POCl$_3$ (0.4 mL, 4.29 mmol) in a sealed tube was purged with nitrogen stream for 1 min and then sealed, heated at 95° C. for 2 h. The reaction mixture was concentrated in vacuo and the residue was dissolved in MeOH, filtered, and purified via preparative HPLC to give a mixture of two isomers. The isomers were further separated by preparative SFC (Method 10% MeOH-DEA on AS column) to give two products. Example 57-1, enantiomer, $T_r$=4.68 min over 10 min run (Method K). Example 57-2, enantiomer 2. $T_r$=7.30 min over 10 min (absolute stereochemistry was not determined).

First eluant, Example 57-1 (10.6 mg, 0.023 mmol, 22.3% yield). LC-MS Anal. Calc'd for $C_{25}H_{31}FN_4O_3$ 454.23, found [M+H] 455.2. $T_r$=1.98 min (Method B). $^1$H NMR (500 MHz, DMSO-d$_6$) δ: 7.97 (d, J=4.9 Hz, 1H), 7.74 (d, J=8.5 Hz, 2H), 7.65 (d, J=9.2 Hz, 1H), 7.24 (d, J=4.9 Hz, 1H), 7.07 (d, J=8.5 Hz, 2H), 4.02 (br. s., 1H), 3.80 (s, 3H), 3.55-3.34 (m, 4H), 2.86 (br. s., 1H), 2.17 (s, 3H), 2.00-1.77 (m, 3H), 1.74-1.40 (m, 6H), 1.06 (t, J=7.0 Hz, 3H).
Second eluant, Example 57-2 (10.7 mg, 0.023 mmol, 22.5% yield). LC-MS Anal. Calc'd for $C_{25}H_{31}FN_4O_3$ 454.23, found [M+H] 455.2. $T_r$=1.99 min (Method B). $^1$H NMR (500 MHz, DMSO-d$_6$) δ: 7.97 (d, J=4.9 Hz, 1H), 7.74 (d, J=8.5 Hz, 2H), 7.65 (d, J=9.2 Hz, 1H), 7.24 (d, J=4.9 Hz, 1H), 7.07 (d, J=8.5 Hz, 2H), 4.02 (br. s., 1H), 3.80 (s, 3H), 3.55-3.34 (m, 4H), 2.86 (br. s., 1H), 2.17 (s, 3H), 2.00-1.77 (m, 3H), 1.74-1.40 (m, 6H), 1.06 (t, J=7.0 Hz, 3H).

Example 58

5-(4-Chlorophenyl)-N-(1-((1s,4s)-4-(6-(trifluoromethyl)quinolin-4-yl)cyclohexyl)propyl)-1,3,4-oxadiazol-2-amine (absolute stereochemistry unknown)

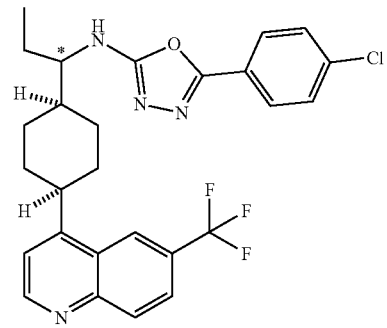 [SMILES: CCC(Nc1nnc(-c2ccc(Cl)cc2)o1)[C@H]1CC[C@@H](c2ccnc3ccc(C(F)(F)F)cc32)CC1]

58A. Ethyl 2-(4-(6-(trifluoromethyl)quinolin-4-yl)cyclohex-3-enyl)acetate

To a solution of 4-chloro-6-(trifluoromethyl)quinoline (2.05 g, 8.85 mmol), ethyl 2-(4-(4,4,5,5-tetramethyl-1,3,2-dioxaborolan-2-yl)cyclohex-3-en-1-yl)acetate (3.12 g, 10.62 mmol) in 1,4-dioxane (35 mL) was added potassium carbonate (3.67 g, 26.6 mmol) and water (7 mL). The reaction mixture was purged with nitrogen stream for 3 min, followed by addition of Pd(Ph$_3$P)$_4$ (0.409 g, 0.354 mmol). The resulting mixture was heated at 100° C. under nitrogen stream for over night. The reaction mixture was cooled down and diluted with ethyl acetate and saturated NaHCO$_3$ solution. The organic layer was separated and washed with sat. NaHCO$_3$ solution, and dried over MgSO$_4$. The filtrate was concentrated in vacuo and the residue was purified via silica gel flash column chromatography, eluting with 0-50% ethyl acetate in hexane to give Intermediate 58A (oil, 3.0 g, 8.26 mmol, 93% yield). LC-MS Anal. Calc'd for C$_{20}$H$_{20}$F$_3$NO$_2$, 363.14, found [M+H] 364.5. T$_r$=0.97 min (Method A). $^1$H NMR (400 MHz, CHLOROFORM-d) δ: 8.95 (d, J=4.5 Hz, 1H), 8.31 (s, 1H), 8.22 (d, J=8.8 Hz, 1H), 7.87 (dd, J=8.8, 2.0 Hz, 1H), 7.29 (d, J=4.5 Hz, 1H), 5.86 (dd, J=2.8, 1.7 Hz, 1H), 4.20 (q, J=7.2 Hz, 2H), 2.65-2.24 (m, 5H), 2.15-1.96 (m, 2H), 1.73-1.54 (m, 2H), 1.36-1.29 (m, 3H)

58B. Ethyl 2-(4-(6-(trifluoromethyl)quinolin-4-yl)cyclohexyl)acetate

The reaction mixture of ethyl 2-(4-(6-(trifluoromethyl)quinolin-4-yl)cyclohex-3-en-1-yl)acetate (3.0 g, 8.26 mmol), ammonium formate (2.08 g, 33.0 mmol) in MeOH (50 mL) was purged with nitrogen stream for 3 min, followed by addition of Pd—C (0.88 g, 0.41 mmol). The resulting mixture was heated at 85° C. for 2 h. The reaction mixture was cooled down. The reaction mixture was filtered through a celite pad and the filter cake was washed with MeOH. The filtrate was concentrated in vacuo. The residue was extracted with ethyl acetate and washed with saturated NaHCO$_3$ solution, brine successively. The organic layer was dried over MgSO$_4$ and the filtrate was concentrated in vacuo to give Intermediate 58B (oil, 2.6 g, 7.12 mmol, 86% yield) as a mixture of cis- and trans-diastereomers. LC-MS Anal. Calc'd for C$_{20}$H$_{22}$F$_3$NO$_2$ 365.16, found [M+H] 366.2. T$_r$=0.94 min (Method A). $^1$H NMR (400 MHz, CHLOROFORM-d) δ: 9.05-8.85 (m, 1H), 8.36 (s, 1H), 8.24 (d, J=8.8 Hz, 1H), 7.88 (dd, J=8.9, 1.7 Hz, 11H), 7.51-7.33 (m, 1H), 4.29-4.03 (m, 2H), 3.51-3.23 (m, 1H), 2.61-2.29 (m, 2H), 2.12-1.35 (m, 9H), 1.32-1.21 (m, 3H)

58C Ethyl 2-((1s,4s)-4-(6-(trifluoromethyl)quinolin-4-yl)cyclohexyl)butanoate To the flask containing THF (15 mL) was added lithium diisopropylamide (2.0 M solution in THF) (7.65 mL, 15.30 mmol) at −78° C., followed by addition of 1,3-dimethyltetrahydropyrimidin-2(1H)-one (1.29 mL, 10.67 mmol) and a solution of ethyl 2-(4-(6-(trifluoromethyl)quinolin-4-yl)cyclohexyl)acetate (2.6 g, 7.12 mmol) in THF (10 mL) dropwise at −78° C. The resulting mixture turned into dark brown solution and stirred at −78° C. for 1 h, then iodoethane (1.14 mL, 14.23 mmol) was added slowly. The reaction mixture was warmed to rt and stirred for 3 h. The reaction was quenched by pouring into water and extracted with EtOAc. Combined organics was washed with brine, dried with MgSO$_4$, filtered and the filtrate was concentrated in vacuo. The extract was purified via silica gel flash column chromatography, eluting with 0-20% ethyl acetate in hexane to give the minor trans isomer and the major cis isomer Intermediate 58C (oil, 1.1 g, 2.77 mmol, 39% yield). The cis isomer contaminated with small amount of trans isomer. LC-MS Anal. Calc'd for C$_{22}$H$_{26}$F$_3$NO$_2$393.19, found [M+H] 394.3. T$_r$=0.97 min (Method A). $^1$H NMR (400 MHz, CHLOROFORM-d) δ: 8.97 (d, J=4.6 Hz, 1H), 8.37 (s, 1H), 8.24 (d, J=8.8 Hz, 1H), 7.88 (dd, J=8.8, 2.0 Hz, 1H), 7.46 (d, J=4.6 Hz, 11H), 4.20 (q, J=7.2 Hz, 2H), 3.57-3.32 (m, 1H), 2.64 (td, J=10.8, 4.0 Hz, 1H), 2.14-1.58 (m, 11H), 1.29 (t, J=7.2 Hz, 3H), 0.95 (t, J=7.4 Hz, 3H).

58D. 2-((1s,4s)-4-(6-(Trifluoromethyl)quinolin-4-yl)cyclohexyl)butanoic acid To the reaction mixture of major isomer ethyl 2-((1s,4s)-4-(6-(trifluoromethyl)quinolin-4-yl)cyclohexyl)butanoate (1.1 g, 2.80 mmol) in THF (20 mL) and MeOH (8 mL) was added lithium hydroxide solution (2.0 M solution) (13.98 mL, 28.0 mmol). The resulting mixture was heated at 65° C. over weekend. The reaction mixture was cooled down and diluted with water. To the mixture was added 1 N HCl solution to adjust pH to about 5. White solid crashed out at pH 5-6. The resulting mixture was extracted with ethyl acetate twice. The organic layer was separated, washed with brine, and dried over MgSO$_4$. The filtrate was concentrated in vacuo to give Intermediate 58D as a racemate (yellow solid, 0.93 g, 2.55 mmol, 91% yield). LC-MS Anal. Calc'd for C$_{20}$H$_{22}$F$_3$NO$_2$ 365.16, found [M+H] 366.3. T$_r$=0.81 min (Method A). $^1$H NMR (400 MHz, DMSO-d$_6$) δ: 12.10 (br. s., 1H), 8.99 (d, J=4.6 Hz, 1H), 8.57 (s, 1H), 8.23 (d, J=8.8 Hz, 1H), 8.00 (dd, J=8.7, 1.9 Hz, 1H), 7.65 (d, J=4.6 Hz, 1H), 3.61 (d, J=10.3 Hz, 1H), 1.96-1.54 (m, 11H), 1.49-1.29 (m, 1H), 0.90 (t, J=7.4 Hz, 3H).

58E. 2-(4-Chlorobenzoyl)-N-(1-((1s,4s)-4-(6-(trifluoromethyl)quinolin-4-yl)cyclohexyl)propyl)hydrazinecarboxamide To a solution of 2-((1s,4s)-4-(6-(trifluoromethyl)quinolin-4-yl)cyclohexyl)butanoic acid (100 mg, 0.274 mmol) in Toluene (5 mL) were added DPPA (0.1 mL, 0.4 mmol) and triethylamine (0.05 mL, 0.4 mmol). The reaction mixture was heated to 70° C. for 2 h. The reaction was cooled to rt. and was concentrated under reduced pressure. The residue was used in the next step reaction without purification. To a solution of crude 4-((1s,4s)-4-(1-isocyanatopropyl)cyclohexyl)-6-(trifluoromethyl)quinoline (33 mg, 0.091 mmol) in THF (3 mL) were added 4-chlorobenzohydrazide, HCl (23 mg, 0.11 mmol) and DIPEA (0.1 mL, 0.6 mmol). The reaction mixture was stirred at rt over night. The reaction mixture was diluted with ethyl acetate and sat. NaHCO$_3$ solution. The organic layer was separated and concentrated in vacuo.

LC-MS Anal. Calc'd for C$_{27}$H$_{28}$ClF$_3$N$_4$O$_2$ 532.18, found [M+H] 533.1. T$_r$=0.89 min (Method A).

Example 58 5-(4-Chlorophenyl)-N-(1-((1s,4s)-4-(6-(trifluoromethyl)quinolin-4-yl)cyclohexyl)propyl)-1,3,4-oxadiazol-2-amine The crude reaction mixture of 2-(4-chlorobenzoyl)-N-(1-((1s,4s)-4-(6-(trifluoromethyl)quinolin-4-yl)cyclohexyl)propyl)hydrazinecarboxamide (36 mg, 0.068 mmol) in POCl$_3$ (0.4 mL, 4.29 mmol) was heated at 90° C. over night. The reaction mixture was concentrated in vacuo and the residue was dissolved in MeOH, filtered, and purified via preparative HPLC to give a mixture of two isomers. The isomers were further separated by preparative SFC (Method F) to give two isolates. Example 58-1, enantiomer 1, T$_r$=15.36 min over 30 min run (Method C). Example 58-2, enantiomer 2. T$_r$=16.89 min over 30 min (absolute stereochemistry was not determined).

First eluant, Example 58-1 (8.6 mg, 0.017 mmol, 24.5% yield). LC-MS Anal. Calc'd for $C_{27}H_{26}ClF_3N_4O$ 514.17, found [M+H] 515.4. $T_r$=1.86 min (Method B). $^1$H NMR (500 MHz, DMSO-$d_6$) δ: 9.01 (d, J=4.3 Hz, 1H), 8.55 (br. s., 1H), 8.23 (d, J=8.8 Hz, 1H), 7.99 (d, J=8.5 Hz, 1H), 7.85-7.71 (m, 3H), 7.67-7.52 (m, 3H), 3.90 (d, J=7.3 Hz, 1H), 3.62 (br. s., 1H), 1.94-1.61 (m, 10H), 1.55-1.37 (m, 1H), 0.93 (t, J=7.2 Hz, 3H).

Second eluant, Example 58-2 (7.9 mg, 0.015 mmol, 22.5% yield). LC-MS Anal. Calc'd for $C_{27}H_{26}ClF_3N_4O$ 514.17, found [M+H] 515.4. $T_r$=1.86 min (Method B). $^1$H NMR (500 MHz, DMSO-$d_6$) δ: 9.01 (d, J=4.6 Hz, 1H), 8.55 (s, 1H), 7.99 (d, J=8.5 Hz, 11H), 7.85-7.71 (m, 3H), 7.63 (d, J=4.3 Hz, 1H), 7.59 (d, J=8.5 Hz, 2H), 3.90 (d, J=8.5 Hz, 1H), 3.62 (br. s., 1H), 2.00-1.58 (m, 10H), 1.46 (dt, J=14.5, 7.4 Hz, 1H), 0.92 (t, J=7.2 Hz, 3H).

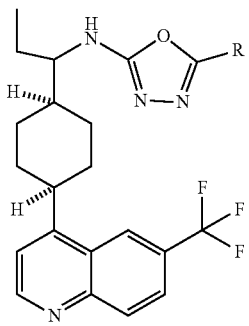

Examples 59-62 were prepared following the procedure for Example 58 using the corresponding acid.

Example 63, Two Isomers

N-(1-((1s,4s)-4-(2-Fluoro-3-methylpyridin-4-yl)cyclohexyl)propyl)-5-(4-methoxyphenyl)-1,3,4-oxadiazol-2-amine

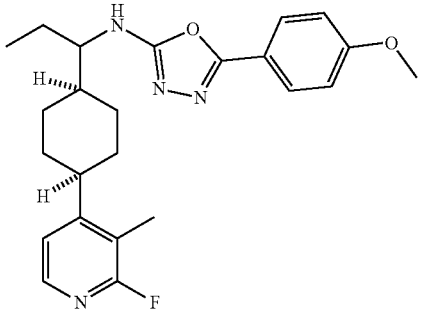 [SMILES: CCC(Nc1nnc(-c2ccc(OC)cc2)o1)[C@H]1CC[C@@H](c2ccnc(F)c2C)CC1]

4-Bromo-2-fluoro-3-methylpyridine

To a homogeneous mixture of LDA (2M solution) (34 mL, 68.0 mmol) in THF (65 mL) at −70° C. under argon, was slowly added a solution of 4-bromo-2-fluoropyridine (9.3 g, 52.8 mmol) in THF (5 mL). The mixture was stirred for 5 hours at −70° C. before EtI (6.9 mL, 111 mmol) was added while keeping the reaction temperature below −65° C. The reaction was allowed to warm to −60° C. before water (100 mL) was added. The mixture was stirred and allowed to warm to rt overnight. The reaction mixture was trans-

| Ex. No. | Name | R | Tr (min) Method B * | [M + H]⁺ |
|---|---|---|---|---|
| Example 59 | 5-(4-methoxyphenyl)-N-(1-((1s,4s)-4-(6-(trifluoromethyl)quinolin-4-yl)cyclohexyl)propyl)-1,3,4-oxadiazol-2-amine | 4-methoxyphenyl | 1.68 | 511.3 |
| Example 60 | 5-(4-methoxyphenyl)-N-(1-((1s,4s)-4-(6-(trifluoromethyl)quinolin-4-yl)cyclohexyl)propyl)-1,3,4-oxadiazol-2-amine | 4-methoxyphenyl | 1.68 | 511.3 |
| Example 61 | 5-(4-fluorophenyl)-N-(1-((1s,4s)-4-(6-(trifluoromethyl)quinolin-4-yl)cyclohexyl)propyl)-1,3,4-oxadiazol-2-amine | 4-fluorophenyl | 1.89 | 499.3 |
| Example 62 | 5-(4-fluorophenyl)-N-(1-((1s,4s)-4-(6-(trifluoromethyl)quinolin-4-yl)cyclohexyl)propyl)-1,3,4-oxadiazol-2-amine | 4-fluorophenyl | 1.88 | 499.3 |

* unless otherwise noted ferred to separational funnel. The aqueous phase is extracted with ether, washed with water, brine, dried over $Na_2SO_4$ and concentrated in vacuo to afford a yellow-orange oil. The extract was purified via silica gel flash column chromatography, eluting with 0-25% ethyl acetate in hexane to give Intermediate 63A (oil, 6.66 g, 35.0 mmol, 66% yield). LC-MS Anal. Calc'd for $C_6H_5BrFN$, 188.96, found [M+H] 191.9. $T_r$=0.85 min (Method A). $^1$H NMR (400 MHz, DMSO-$d_6$) δ: 7.96 (d, J=5.4 Hz, 1H), 7.62 (d, J=5.4 Hz, 1H), 2.30-2.28 (m, 3H).

63B. Ethyl 2-(4-(2-fluoro-3-methylpyridin-4-yl)cyclohex-3-enyl)acetate

To a reaction flask containing a solution of ethyl 2-(4-(4,4,5,5-tetramethyl-1,3,2-dioxaborolan-2-yl)cyclohex-3-en-1-yl)acetate (5.93 g, 20.17 mmol) in Dioxane (120 mL) was added 4-bromo-2-fluoro-3-methylpyridine (3.72 g, 19.58 mmol), Water (40.0 mL) and $Na_2CO_3$ (8.30 g, 78 mmol). After the mixture was degassed with Ar for 10-15 min, $Pd(Ph_3P)_4$ (1.13 g, 0.979 mmol) was added. The flask was sealed and the mixture was heated to 100° C. overnight. The reaction mixture was cooled to rt. Some solid white material is present at bottom of reaction flask. Reaction was diluted with EtOAc and water, plus sonication to break up solids, then transferred to a separational funnel. The layers were separated and the aqueous layer was extracted once more with EtOAc. The organic layers were combined, washed with brine, dried over anhyd $Na_2SO_4$, filtered and concentrated in vacuo to afford a white precipitate in a pale gold residue. The extract was purified via silica gel flash column chromatography, eluting with 0-20% ethyl acetate in hexane to give Intermediate 63B (pale gold oil, 5.01 g, 17.72 mmol, 91% yield). LC-MS Anal. Calc'd for $C_{16}H_{20}FNO_2$ 277.15, found [M+H] 278.1. $T_r$=1.02 min (Method A). $^1$H NMR (400 MHz, CHLOROFORM-d) δ: 7.93 (d, J=5.0 Hz, 1H), 6.91-6.85 (m, 1H), 5.64-5.57 (m, J=2.9, 1.7 Hz, 1H), 4.17 (q, J=7.1 Hz, 2H), 2.41-2.28 (m, 5H), 2.21-2.18 (m, 4H), 1.98-1.87 (m, 2H), 1.54-1.42 (m, J=12.8, 10.6, 10.6, 5.4 Hz, 1H), 1.28 (t, J=7.2 Hz, 3H).

63C. Ethyl 2-((1s,4s)-4-(2-fluoro-3-methylpyridin-4-yl)cyclohexyl)butanoate

To a flask containing THF (15 mL) was added LDA (1.5 M solution in cyclohexane) (11.0 mL, 16.54 mmol) and DMPU (1.36 mL, 11.28 mmol) at −78° C. followed by addition of a solution of ethyl 2-((1s,4s)-4-(2-fluoro-3-methylpyridin-4-yl)cyclohexyl)acetate (2.1 g, 7.52 mmol) in THF (8 mL) dropwise at −78° C. The resulting orange solution mixture was stirred at −78° C. for 1 h, then iodoethane (0.97 mL, 12.03 mmol) was added. The reaction mixture was stirred at −78° C., then gradually warmed up to rt for 4 h. The reaction mixture turned into a cloudy yellow mixture. The reaction mixture was quenched with $NH_4Cl$ aqueous solution. The resulting mixture was extracted with ethyl acetate. The organic layers of extract were combined, washed with brine, dried over $MgSO_4$. The filtrate was concentrated in vacuo. The extract was purified via silica gel flash column chromatography, eluting with 0-20% ethyl acetate in hexane to give Intermediate 63C (oil, 1.31 g, 4.26 mmol, 56.7% yield). LC-MS Anal. Calc'd for $C_{18}H_{26}FNO_2$ 307.1, found [M+H] 308.2. $T_r$=1.08 min (Method A). $^1$H NMR (400 MHz, CHLOROFORM-d) δ: 7.98 (d, J=5.1 Hz, 1H), 7.08 (d, J=5.3 Hz, 1H), 4.19 (q, J=7.1 Hz, 2H), 2.93-2.74 (m, 1H), 2.62 (td, J=10.8, 3.9 Hz, 1H), 2.23 (d, J=1.1 Hz, 3H), 2.04-1.86 (m, 2H), 1.77-1.43 (m, 9H), 1.28 (t, J=7.2 Hz, 3H), 0.94 (t, J=7.4 Hz, 3H).

63D. 2-((1s,4s)-4-(2-Fluoro-3-methylpyridin-4-yl)cyclohexyl)butanoic acid

To the reaction mixture of ethyl 2-((1s,4s)-4-(2-fluoro-3-methylpyridin-4-yl)cyclohexyl)butanoate (0.9 g, 2.93 mmol) in THF (10 mL) and MeOH (6 mL) was added LiOH solution (2 M) (14.64 mL, 29.3 mmol). The reaction mixture was heated at 70° C. for over night.
The reaction was not complete. To the reaction mixture was added more LiOH solution (2 M) (4 mL, 8 mmol) and MeOH (6 mL). The reaction mixture was heated at 70° C. for another 20 h. The reaction mixture was cooled down and to the reaction mixture was added 2 mL of acetic acid to adjust pH to about 5. The resulting mixture was extracted with ethyl acetate twice and the organic layers was washed with brne, dried over $MgSO_4$. The filtrate was concentrated in vacuo. and the residue was dissolved in MeOH, filtered, and purified via preparative HPLC to give Intermediate 63D (425 mg, 1.506 mmol, 51.4% yield). LC-MS Anal. Calc'd for $C_{16}H_{22}FNO_2$ 279.16, found [M+H] 280.1. $T_r$=0.89 min (Method A). $^1$H NMR (400 MHz, METHANOL-$d_4$) δ: 7.94 (d, J=5.3 Hz, 1H), 7.24 (d, J=5.3 Hz, 1H), 2.93 (d, J=4.2 Hz, 1H), 2.65 (td, J=10.8, 3.7 Hz, 1H), 2.25 (d, J=0.9 Hz, 3H), 1.95 (br. s., 2H), 1.83-1.40 (m, 9H), 0.97 (t, J=7.4 Hz, 3H).

63E. N-(1-((1s,4s)-4-(2-fluoro-3-methylpyridin-4-yl)cyclohexyl)propyl)-2-(4-methoxybenzoyl)hydrazinecarboxamide To a suspension of 2-(4-(2-fluoro-3-methylpyridin-4-yl)cyclohexyl)butanoic acid (0.24 g, 0.859 mmol) in Toluene (8 mL) were added diphenylphosphoryl azide (0.23 mL, 1.03 mmol) and TEA (0.42 mL, 3.01 mmol). The reaction mixture in a sealed vial turned into clear solution after addition of TEA. The reaction mixture was heated to 70° C. for 2 h. The reaction was cooled to rt. and concentrated under reduced pressure. A portion of the intermediate 2-fluoro-4-((1s,4s)-4-(1-isocyanatopropyl)cyclohexyl)-3-methylpyridine (45 mg, 0.163 mmol) in THF (1 mL) was added to a suspension of 4-methoxybenzohydrazide, HCl (39.6 mg, 0.195 mmol) in THF (1 mL), followed by addition of DIPEA (0.11 mL, 0.65 mmol). The reaction mixture was stirred at rt for 2 h. The reaction mixture was concentrated in vacuo to give the crude product. It was used in the next step without purification. LC-MS Anal. Calc'd for $C_{24}H_{31}FN_4O_3$ 442.2, found [M+H] 443.1. $T_r$=0.89 min (Method A).

Example 63, Two isomers N-(1-((1s,4s)-4-(2-fluoro-3-methylpyridin-4-yl)cyclohexyl)propyl)-5-(4-methoxyphenyl)-1,3,4-oxadiazol-2-amine The crude reaction mixture of N-(1-((s,4s)-4-(2-fluoro-3-methylpyridin-4-yl)cyclohexyl)propyl)-2-(4-methoxybenzoyl)hydrazinecarboxamide (60 mg, 0.136 mmol) in $POCl_3$ (0.4 mL, 4.29 mmol) was heated at 90° C. over night. The reaction mixture was concentrated in vacuo and the residue was dissolved in MeOH, filtered, and purified via preparative HPLC to give a mixture of two isomers. The isomers were further separated by preparative SFC (Method J) to give two isolates. Example 63-1, enantiomer 1, $T_r$=3.73 min over 8 min run (Method J). Example 63-2, enantiomer 2. $T_r$=5.80 min over 8 min (absolute stereochemistry was not determined).

First eluant, Example 63-1 (6.9 mg, 0.016 mmol, 11.9% yield). LC-MS Anal. Calc'd for $C_{24}H_{29}FN_4O_2$ 424.22, found [M+H] 425.2. $T_r$=1.93 min (Method B). $^1$H NMR (500 MHz, DMSO-$d_6$) δ: 7.99 (d, J=4.9 Hz, 1H), 7.73 (d, J=8.5 Hz, 2H), 7.56 (d, J=9.2 Hz, 1H), 7.25 (d, J=4.9 Hz, 1H), 7.07 (d, J=8.5 Hz, 2H), 4.01-3.73 (m, 4H), 2.87 (br. s., 1H), 2.18 (s, 3H), 1.92-1.34 (m, 11H), 0.91 (t, J=7.3 Hz, 3H)

Second eluant, Example 63-2 (6.7 mg, 0.016 mmol, 11.5% yield). LC-MS Anal. Calc'd for $C_{24}H_{29}FN_4O_2$ 424.22, found [M+H] 425.1. $T_r$=1.93 min (Method B). $^1$H NMR (500 MHz, DMSO-$d_6$) δ: 7.99 (d, J=4.9 Hz, 1H), 7.73 (d, J=8.5 Hz, 2H), 7.56 (d, J=9.2 Hz, 1H), 7.25 (d, J=4.9 Hz, 1H), 7.07 (d, J=8.5 Hz, 2H), 4.01-3.73 (m, 4H), 2.87 (br. s., 1H), 2.18 (s, 3H), 1.92-1.34 (m, 11H), 0.91 (t, J=7.3 Hz, 3H)

Example 64, Two Isomers 5-(4-Methoxyphenyl)-N—((R)-1-((1r,4R)-4-(quinolin-4-yloxy)cyclohexyl)propyl)-1,3,4-oxadiazol-2-amine

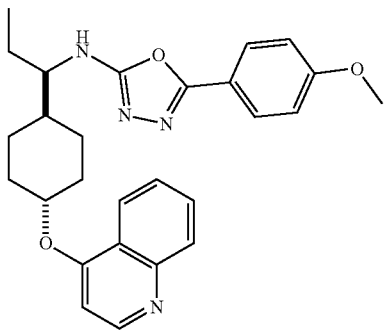

64A. 2-((1r,4r)-4-(quinolin-4-yloxy)cyclohexyl)butanoic acid

To a solution of ethyl 2-((1r,4r)-4-(quinolin-4-yloxy)cyclohexyl)butanoate (0.13 g, 0.381 mmol) in THF (6 mL) and MeOH (1 mL) was added LiOH solution (2 M) (1.91 mL, 3.81 mmol). The reaction mixture was heated at 45° C. for 4 days. To the reaction mixture was added water and 1 N HCl solution to adjust pH to about 6. The resulting mixture was extracted with ethyl acetate. The organic layer was separated and dried over MgSO$_4$. The filtrate was concentrated in vacuo. The extract was dissolved in MeOH, purified by preparative HPLC. Fractions containing the desired product were combined and concentrated in vacuo to give Intermediate 64A (white solid, 0.1 g, 0.319 mmol, 84% yield). LC-MS Anal. Calc'd for $C_{19}H_{23}NO_3$ 313.17, found [M+H] 314.2. $T_r$=0.68 min (Method A). $^1$H NMR (400 MHz, METHANOL-$d_4$) δ: 8.93 (d, J=6.8 Hz, 1H), 8.47 (d, J=8.1 Hz, 1H), 8.24-7.99 (m, 2H), 7.87 (ddd, J=8.4, 6.9, 1.2 Hz, 1H), 7.56 (d, J=7.0 Hz, 1H), 5.18-4.91 (m, 1H), 2.55-2.29 (m, 2H), 2.21-2.02 (m, 2H), 1.98-1.87 (m, 1H), 1.83-1.56 (m, 5H), 1.50-1.25 (m, 2H), 0.95 (t, J=7.4 Hz, 3H).

64B. 2-(4-Methoxybenzoyl)-N-(1-((1r,4r)-4-(quinolin-4-yloxy)cyclohexyl)propyl)hydrazinecarboxamide To a solution of 2-((1r,4r)-4-(quinolin-4-yloxy)cyclohexyl)butanoic acid (0.1 g, 0.319 mmol) in toluene (6 mL) was added TEA (0.14 mL, 0.96 mmol) and diphenylphosphoryl azide (0.1 mL, 0.42 mmol). The reaction mixture was heated at 70° C. for 1.5 h. The reaction mixture was concentrated in vacuo to give the intermediate. To a suspension of 4-methoxybenzohydrazide, HCl (42.4 mg, 0.209 mmol) in THF (2 mL) were added DIPEA (0.17 mL, 0.97 mmol) and the intermediate solution of 4-(((1r,4r)-4-(1-isocyanatopropyl)cyclohexyl)oxy)quinoline (50 mg, 0.161 mmol) in THF (2 mL). The reaction mixture was stirred at rt for 3 h. The reaction mixture was concentrated in vacuo and the residue was extracted with ethyl acetate. The organic layer was concentrated in vacuo. The crude product was dissolved in MeOH, purified by preparative HPLC. Fractions containing the desired product were combined and concentrated in vacuo to give Intermediate 64B TFA salt (white solid, 60 mg, 0.102 mmol, 63% yield). LC-MS Anal. Calc'd for $C_{27}H_{32}N_4O_4$. TFA, 476.24, found [M+H] 477.2. $T_r$=0.70 min (Method A). $^1$H NMR (400 MHz, METHANOL-$d_4$) δ: 8.89 (d, J=6.6 Hz, 1H), 8.42 (d, J=8.6 Hz, 1H), 8.07 (d, J=2.9 Hz, 2H), 7.91-7.79 (m, 3H), 7.52 (d, J=6.8 Hz, 1H), 7.34-7.13 (m, 3H), 7.01-6.91 (m, 2H), 3.84 (s, 3H), 3.63-3.47 (m, 1H), 2.35 (d, J=10.1 Hz, 2H), 2.13-1.83 (m, 2H), 1.78-1.15 (m, 8H), 0.97 (t, J=7.3 Hz, 3H)

Example 64, Two isomers 5-(4-Methoxyphenyl)-N—((R)-1-((1r,4R)-4-(quinolin-4-yloxy)cyclohexyl)propyl)-1,3,4-oxadiazol-2-amine The reaction mixture of 2-(4-methoxybenzoyl)-N-(1-((1r,4r)-4-(quinolin-4-yloxy)cyclohexyl)propyl)hydrazinecarboxamide, TFA (60 mg, 0.102 mmol) in POCl$_3$ (0.4 mL, 4.29 mmol) in a sealed tube was purged with nitrogen stream, then sealed and heated at 90° C. over night. The reaction mixture was concentrated in vacuo and the residue was dissolved in MeOH, filtered, and purified via preparative HPLC to give a mixture of two isomers. The isomers were further separated by preparative SFC (Method L) to give two isolates. Example 64-1, enantiomer 1, $T_r$=63.46 min over 10 min run (Method L). Example 64-2, enantiomer 2. $T_r$=6.20 min over 10 min (absolute stereochemistry was not determined).

First eluant, Example 64-1 (8.2 mg, 0.017 mmol, 17.4% yield). LC-MS Anal. Calc'd for $C_{27}H_{30}N_4O_3$, 458.23, found [M+H] 459.3. $T_r$=1.58 min (Method B). $^1$H NMR (600 MHz, DMSO-$d_6$) δ: 8.65 (d, J=5.2 Hz, 1H), 8.11 (d, J=8.3 Hz, 1H), 7.91 (d, J=8.3 Hz, 11H), 7.75 (d, J=8.7 Hz, 2H), 7.71 (t, J=7.6 Hz, 11H), 7.58 (d, J=9.1 Hz, 1H), 7.52 (t, J=7.6 Hz, 1H), 7.15-6.98 (m, 3H), 4.83-4.35 (m, 1H), 3.81 (s, 3H), 3.45-3.32 (m, 1H), 2.22 (d, J=10.7 Hz, 2H), 1.93-1.79 (m, 2H), 1.72-1.25 (m, 7H), 0.90 (t, J=7.3 Hz, 3H)

Second eluant, Example 64-2 (8.1 mg, 0.017 mmol, 17.2% yield). LC-MS Anal. Calc'd for $C_{27}H_{30}N_4O_3$, 458.23, found [M+H] 459.0. $T_r$=1.58 min (Method B). $^1$H NMR (600 MHz, DMSO-$d_6$) δ: 8.65 (d, J=4.8 Hz, 1H), 8.11 (d, J=8.3 Hz, 1H), 7.91 (d, J=8.3 Hz, 1H), 7.81-7.66 (m, 3H), 7.58 (d, J=9.1 Hz, 1H), 7.52 (t, J=7.6 Hz, 1H), 7.20-6.97 (m, 3H), 4.75-4.46 (m, 1H), 3.81 (s, 3H), 3.47-3.30 (m, 1H), 2.22 (d, J=10.1 Hz, 2H), 1.85 (br. s., 2H), 1.70-1.41 (m, 5H), 1.32 (br. s., 2H), 0.90 (t, J=7.3 Hz, 3H)

Example 65, Two Isomers

N-(1-((1s,4s)-4-(6-Fluoroquinolin-4-yl)cyclohexyl)-2-methoxyethyl)-5-(4-methoxyphenyl)-1,3,4-oxadiazol-2-amine

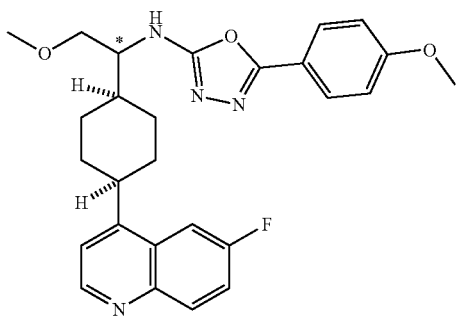

65A. Ethyl 2-(4-(6-fluoroquinolin-4-yl)cyclohex-3-en-1-yl)acetate

Ethyl 2-(4-(4,4,5,5-tetramethyl-1,3,2-dioxaborolan-2-yl)cyclohex-3-en-1-yl)acetate (Intermediate BBRC provide) (5 g, 17.00 mmol) was taken up in dioxane (28.3 ml) and water (7.08 ml). 4-chloro-6-fluoroquinoline (2.57 g, 14.15 mmol) was added followed by K$_2$CO$_3$ (5.87 g, 42.5 mmol). Mixture was bubble with nitrogen gas for 5 minutes before the addition of Pd(Ph$_3$P)$_4$ (0.327 g, 0.283 mmol). After addition, reaction was vacated and backfilled with N2 three times and then sealed (sealed vial parafilmed) and heated to 100° C. for 16 hours. The reaction was concentrated in vacuo and purified directly via silica gel flash column chromatography to give Intermediate 65A (4.22 g, 13.47 mmol, 95% yield). LC-MS Anal. Calc'd for C$_{19}$H$_{20}$FNO$_2$ 313.15, found [M+H] 314.1 T$_r$=0.75 min (Method A). $^1$H NMR (400 MHz, CHLOROFORM-d) δ: 8.80 (d, J=4.4 Hz, 1H), 8.10 (dd, J=9.2, 5.6 Hz, 1H), 7.60 (dd, J=10.2, 2.9 Hz, 1H), 7.46 (ddd, J=9.2, 8.1, 2.8 Hz, 1H), 7.19 (d, J=4.4 Hz, 1H), 5.82 (dd, J=2.9, 1.7 Hz, 1H), 4.19 (q, J=7.2 Hz, 2H), 2.60-2.20 (m, 6H), 2.10-1.94 (m, 2H), 1.67-1.51 (m, 1H), 1.37-1.28 (m, 3H).

65B. Ethyl 2-(4-(6-fluoroquinolin-4-yl)cyclohex-3-enyl)-3-methoxypropanoate

To the flask containing THF (8 mL) was added LDA (1.5 M solution in hexane) (4.89 mL, 7.34 mmol) at −78° C., followed by addition of 1,3-dimethyltetrahydropyrimidin-2(1H)-one (0.54 mL, 4.47 mmol) and a solution of ethyl 2-(4-(6-fluoroquinolin-4-yl)cyclohex-3-en-1-yl)acetate (1.0 g, 3.19 mmol) in THF (3 mL) dropwise at −78° C. The resulting mixture turned into green and stirred at −78° C. for 1 h, then MOMCl (0.39 mL, 5.11 mmol) was added slowly. The reaction mixture was stirred at −78° C. for 0.5 h, then warmed up to about −20° C. for 4 h, then warmed to rt over night. The reaction mixture was quenched with water and the resulting mixture was extracted with ethyl acetate. The organic layer was separated and washed with brine, dried over MgSO$_4$. The filtrate was concentrated in vacuo. The residue was dissolved in DCM, purified via silica gel flash column chromatography, eluting with 0-30% ethyl acetate in DCM to give Intermediate 65B (light brown oil, 0.8 g, 2.238 mmol, 70% yield). LC-MS Anal. Calc'd for C$_{21}$H$_{24}$FNO$_3$ 357.17, found [M+H] 358.2. T$_r$=0.78 min (Method A). $^1$H NMR (400 MHz, CHLOROFORM-d) δ: 8.80 (d, J=4.4 Hz, 1H), 8.10 (dd, J=9.2, 5.5 Hz, 1H), 7.60 (dt, J=10.1, 2.9 Hz, 1H), 7.47 (ddd, J=9.1, 8.0, 2.9 Hz, 1H), 7.18 (d, J=4.4 Hz, 1H), 5.97-5.69 (m, 1H), 4.45-4.13 (m, 2H), 3.92-3.59 (m, 2H), 3.39 (s, 3H), 2.83-2.63 (m, 1H), 2.57-1.83 (m, 6H), 1.70-1.59 (m, 1H), 1.33 (td, J=7.2, 1.8 Hz, 3H).

65C. Ethyl 2-((1s,4s)-4-(6-fluoroquinolin-4-yl)cyclohexyl)-3-methoxypropanoate To a solution of ethyl 2-(4-(6-fluoroquinolin-4-yl)cyclohex-3-en-1-yl)-3-methoxypropanoate (1.08 g, 3.02 mmol) in methanol (20 mL) was added Pd—C (10% wt. wet) (0.64 g, 0.30 mmol). The reaction mixture was evacuated and then filled with hydrogen, evacuated again and under hydrogenation with a hydrogen balloon at rt over night. The reaction mixture was filtered through a celite pad and the pad was washed with ethyl acetate and MeOH. The filtrate was concentrated in vacuo. The crude product was separated by for SFC purification (method: 10% IPA on Waters BEH 2-ethylpyridine column). The major product fractions were collected and concentrated in vacuo to give Intermediate 65C (colorless oil, 0.44 g, 1.224 mmol, 40.5% yield). LC-MS Anal. Calc'd for C$_{21}$H$_{26}$FNO$_3$, 359.19 found [M+H] 360.2. T$_r$=0.74 min (Method A). $^1$H NMR (400 MHz, CHLOROFORM-d) δ: 8.83 (d, J=4.6 Hz, 1H), 8.13 (dd, J=9.2, 5.7 Hz, 1H), 7.65 (dd, J=10.6, 2.6 Hz, 1H), 7.48 (ddd, J=9.2, 7.9, 2.8 Hz, 1H), 7.35 (d, J=4.6 Hz, 1H), 4.22 (dd, J=12.0, 7.2 Hz, 2H), 3.74-3.48 (m, 2H), 3.37 (s, 3H), 3.32-3.19 (m, 1H), 3.06 (ddd, J=10.9, 9.2, 5.0 Hz, 1H), 2.12 (d, J=10.6 Hz, 1H), 1.98-1.64 (m, 8H), 1.29 (t, J=7.2 Hz, 3H)

65D. 2-((1s,4s)-4-(6-Fluoroquinolin-4-yl)cyclohexyl)-3-methoxypropanoic acid To a solution of ethyl 2-((1s,4s)-4-(6-fluoroquinolin-4-yl)cyclohexyl)-3-methoxypropanoate (0.44 g, 1.22 mmol) in THF (5 mL) and MeOH (5 mL) was added LiOH solution (2.0 m solution) (3.67 mL, 7.34 mmol). The reaction mixture was stirred at rt over night. To the reaction mixture was added more MeOH (5 mL) (2 mL) and LiOH solution (2.0 m solution) (3.67 mL, 7.34 mmol) (4 mL) and the reaction mixture was heated at 65° C. for 6 h, then stirred at 40° C. over weekend. The reaction was cooled down and diluted with water, and 1 N HCl solution to adjust pH to 4-5 and the resulting mixture was extracted with ethyl acetate twice. The organic layer was separated and dried over MgSO$_4$. The filtrate was concentrated in vacuo to give Intermediate 65D (light brown oil, 0.38 g, 1.147 mmol, 94% yield). LC-MS Anal. Calc'd for C$_{19}$H$_{22}$FNO$_3$ 331.15, found [M+H] 332.2. T$_r$=0.62 min (Method A). $^1$H NMR (400 MHz, METHANOL-d$_4$) δ: 8.99 (d, J=5.5 Hz, 1H), 8.32-8.16 (m, 2H), 7.95 (d, J=5.5 Hz, 1H), 7.89 (ddd, J=9.2, 7.9, 2.6 Hz, 1H), 3.82-3.54 (m, 3H), 3.36 (s, 3H), 3.07 (ddd, J=11.1, 9.0, 4.8 Hz, 1H), 2.09 (d, J=11.0 Hz, 1H), 2.03-1.74 (m, 8H)

65E. N-(1-((1s,4s)-4-(6-fluoroquinolin-4-yl)cyclohexyl)-2-methoxyethyl)-2-(4-methoxybenzoyl)hydrazinecarboxamide To a suspension of 2-((1s,4s)-4-(6-fluoroquinolin-4-yl)cyclohexyl)-3-methoxypropanoic acid, TFA (50 mg, 0.112 mmol) in Toluene (4 mL) were added diphenylphosphoryl azide (0.03 mL, 0.146 mmol) and TEA (0.063 mL, 0.449 mmol). The reaction mixture in a sealed vial turned into clear solution after addition of TEA. The reaction mixture was heated to 70° C. for 2 h. The reaction was cooled to rt. and concentrated under reduced pressure. To the crude 6-fluoro-4-((1s,4s)-4-(1-isocyanato-2-methoxyethyl)cyclohexyl)quinoline (30 mg, 0.091 mmol) in THF (2 mL) was added 4-methoxybenzohydrazide, HCl (24.07 mg, 0.119 mmol) and TEA (0.064 mL, 0.457 mmol). The reaction mixture was stirred at rt for 2 h. The reaction mixture was concentrated in vacuo. The residue was extracted with ethyl acetate. The organic layer was concentrated in vacuo. The crude product was used in the next step reaction without purification. LC-MS Anal. Calc'd for $C_{27}H_{31}FN_4O_4$ 494.23, found [M+H] 495.3. $T_r$=0.67 min (Method A).

Example 65, Two Isomers N-(1-((1s,4s)-4-(6-Fluoroquinolin-4-yl)cyclohexyl)-2-methoxyethyl)-5-(4-methoxyphenyl)-1,3,4-oxadiazol-2-amine The mixture of crude N-(1-((1s,4s)-4-(6-fluoroquinolin-4-yl)cyclohexyl)-2-methoxyethyl)-2-(4-methoxybenzoyl)hydrazinecarboxamide (35 mg, 0.071 mmol) in $POCl_3$ (0.35 mL, 3.75 mmol) was heated at 90° C. overnight. The reaction mixture was concentrated in vacuo and the residue was dissolved in MeOH, filtered, and purified via preparative HPLC to give a mixture of two isomers. The isomers were further separated by preparative SFC (Method I) to give two isolates. Example 65-1, enantiomer 1. $T_r$=3.87 min over 10 min run (Method I). Example 65-2, enantiomer 2. $T_r$=5.58 min over 10 min (absolute stereochemistry was not determined).
First eluant, Example 65-1 (2.9 mg, 0.006 mmol, 8.4% yield). LC-MS Anal. Calc'd for $C_{27}H_{29}FN_4O_3$ 476.22, found [M+H] 477.3. $T_r$=1.41 min (Method B). $^1$H NMR (500 MHz, DMSO-$d_6$) δ: 8.81 (d, J=4.4 Hz, 1H), 8.08 (dd, J=9.1, 5.8 Hz, 1H), 7.96 (d, J=8.8 Hz, 1H), 7.73 (d, J=8.7 Hz, 3H), 7.68-7.61 (m, 1H), 7.50 (d, J=4.4 Hz, 1H), 7.07 (d, J=8.8 Hz, 2H), 4.05 (br. s., 1H), 3.80 (s, 3H), 3.28 (s, 3H), 2.02-1.58 (m, 10H), 1.21 (s, 2H)
Second eluant, Example 65-2 (3.0 mg, 0.006 mmol, 8.6% yield). LC-MS Anal. Calc'd for $C_{27}H_{29}FN_4O_3$ 476.22, found [M+H] 477.3. $T_r$=1.43 min (Method B). $^1$H NMR (500 MHz, DMSO-$d_6$) δ: 8.81 (d, J=4.4 Hz, 1H), 8.08 (dd, J=9.1, 5.8 Hz, 1H), 7.96 (d, J=8.8 Hz, 1H), 7.73 (d, J=8.7 Hz, 3H), 7.68-7.61 (m, 1H), 7.50 (d, J=4.4 Hz, 1H), 7.07 (d, J=8.8 Hz, 2H), 4.05 (br. s., 1H), 3.80 (s, 3H), 3.28 (s, 3H), 2.02-1.58 (m, 10H), 1.21 (s, 2H).

Example 66

N-(2-Methoxy-1-((1s,4s)-4-(6-(trifluoromethyl)quinolin-4-yl)cyclohexyl)ethyl)-5-(4-methoxyphenyl)-1,3,4-oxadiazol-2-amine

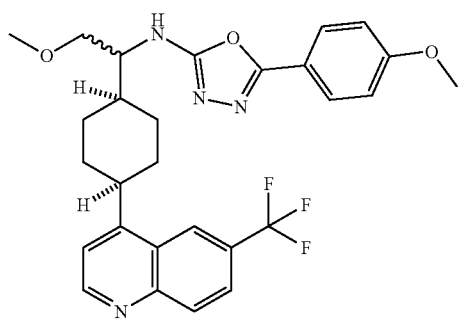

66A. Ethyl 2-((1s,4s)-4-(6-(trifluoromethyl)quinolin-4-yl)cyclohexyl)acetate The reaction mixture of ethyl 2-(4-(6-(trifluoromethyl)quinolin-4-yl)cyclohex-3-en-1-yl)acetate (4.8 g, 13.21 mmol), ammonium formate (2.50 g, 39.6 mmol) in MeOH (80 mL) was purged with nitrogen stream, then evacuated, followed by addition of Pd—C (1.125 g, 0.528 mmol, 10% wt. wet). The resulting mixture was heated at 78° C. for 2 h. The reaction mixture was cooled down. To the reaction mixture was added more Pd—C (1.125 g, 0.528 mmol) (0.5 g) and MeOH (20 mL) and the reaction mixture was heated at 78° C. over night. The reaction mixture was filtered and the filter cake was washed with MeOH. The filtrate was concentrated in vacuo.
The residue was diluted with ethyl acetate and saturated $NaHCO_3$ solution. The organic layer was separated and concentrated in vacuo to give colorless oil. The isomers was separated by SFC (method 12% MeOH on OJ-H column) to give major isomer Intermediate 66A (colorless oil, 2.5 g, 6.84 mmol, 51.8% yield). LC-MS Anal. Calc'd for $C_{20}H_{22}F_3NO_2$ 365.16, found [M+H] 366.1. $T_r$=092 min (Method A). $^1$H NMR (400 MHz, CHLOROFORM-d) δ: 8.96 (d, J=4.6 Hz, 1H), 8.36 (s, 1H), 8.24 (d, J=8.8 Hz, 1H), 7.88 (dd, J=8.8, 1.8 Hz, 1H), 7.43 (d, J=4.6 Hz, 1H), 4.18 (q, J=7.0 Hz, 2H), 3.46-3.31 (m, 1H), 2.57-2.43 (m, 3H), 1.99-1.72 (m, 8H), 1.29 (t, J=7.0 Hz, 3H).

66B. Ethyl 3-methoxy-2-((1s,4s)-4-(6-(trifluoromethyl)quinolin-4-yl)cyclohexyl)propanoate To the flask containing THF (10 mL) was added LDA solution (1.5 M solution in cyclohexane) (3.65 mL, 5.47 mmol) at −78° C., followed by addition of 1,3-dimethyltetrahydropyrimidin-2(1H)-one (0.4 mL, 3.3 mmol) and a solution of ethyl 2-((1 s,4s)-4-(6-(trifluoromethyl)quinolin-4-yl)cyclohexyl)acetate (0.8 g, 2.189 mmol) in THF (5 mL) dropwise at −78° C. The resulting mixture turned into brown color and was stirred at −78° C. for 1 h, then MOMCl (0.25 mL, 3.28 mmol) was added slowly. The reaction mixture was stirred at −78° C. for 2 h, then stirred for 20 h. The reaction mixture was quenched with water and the resulting mixture was extracted with ethyl acetate. The organic layer was separated and washed with brine, dried over $MgSO_4$. The filtrate was concentrated in vacuo. The residue was dissolved in DCM and purified via a gel flash column chromatography, eluting with 0-50% ethyl acetate in hexane to give Intermediate 66B (light yellow oil, 0.39 g, 0.953 mmol, 43.5% yield). LC-MS Anal. Calc'd for $C_{22}H_{26}F_3NO_3$ 409.18. found [M+H] 410.2. $T_r$=0.96 min (Method A). $^1$H NMR (400 MHz, CHLOROFORM-d) δ: 8.97 (d, J=4.6 Hz, 1H), 8.36 (s, 1H), 8.24 (d, J=8.8 Hz, 1H), 7.88 (dd, J=8.8, 1.8 Hz, 1H), 7.45 (d, J=4.6 Hz, 1H), 4.22 (dddd, J=18.2, 11.1, 7.1, 3.6 Hz, 2H), 3.76-3.54 (m, 2H), 3.49-3.40 (m, 1H), 3.38-3.35 (m, 3H), 3.06 (ddd, J=11.0, 9.1, 5.0 Hz, 1H), 2.29-1.67 (m, 9H), 1.29 (t, J=7.2 Hz, 3H).

66C. 3-Methoxy-2-((1s,4s)-4-(6-(trifluoromethyl)quinolin-4-yl)cyclohexyl)propanoic acid To a solution of ethyl 3-methoxy-2-((1s,4s)-4-(6-(trifluoromethyl)quinolin-4-yl)cyclohexyl)propanoate (0.49 g, 1.197 mmol) in THF (6 mL) and MeOH (6 mL) was added LiOH solution (2.0 M solution) (7.2 mL, 14.4 mmol). The reaction mixture was heated at 70° C. for 5 h. The reaction mixture was cooled down and to the mixture was added water and 1 N HCl to adjust pH to 6 and 2 mL of acetic acid was added to adjust pH to 4. White solid precipitated out and the resulting mixture was extracted with ethyl acetate. The organic layer was separated and dried over MgSO$_4$. The filtrate was concentrated in vacuo to give Intermediate 66C (white solid, 0.38 g, 0.996 mmol, 83% yield). Analytical sample was purified by preparative HPLC. LC-MS Anal. Calc'd for $C_{20}H_{22}F_3NO_3$ 381.15, found [M+H] 382.2. $T_r$=0.75 min (Method A). $^1$H NMR (400 MHz, METHANOL-d4) δ: 9.07 (d, J=5.3 Hz, 1H), 8.68 (s, 1H), 8.30 (d, J=8.8 Hz, 1H), 8.15 (dd, J=8.9, 1.7 Hz, 1H), 7.91 (d, J=5.3 Hz, 1H), 3.90-3.52 (m, 3H), 3.40-3.34 (m, 3H), 3.07 (ddd, J=11.1, 9.0, 4.8 Hz, 1H), 2.19-1.67 (m, 9H).

66D. N-(2-methoxy-1-((1s,4s)-4-(6-(trifluoromethyl)quinolin-4-yl)cyclohexyl)ethyl)-2-(4-methoxybenzoyl)hydrazinecarboxamide To a suspension of 3-methoxy-2-((1s,4s)-4-(6-(trifluoromethyl)quinolin-4-yl)cyclohexyl)propanoic acid (0.26 g, 0.682 mmol) in Toluene (8 mL) were added DPPA (0.18 mL, 0.818 mmol) and TEA (0.15 mL, 1.03 mmol). The reaction mixture in a sealed vial turned into clear solution after addition of TEA. The reaction mixture was heated to 70° C. for 2 h. The reaction mixture was concentrated under reduced pressure. To a suspension of a portion of the residue 4-((1s,4s)-4-(1-isocyanato-2-methoxyethyl)cyclohexyl)-6-(trifluoromethyl)quinoline (25 mg, 0.066 mmol) in THF (2 mL) was added 4-methoxybenzohydrazide, HCl (16 mg, 0.08 mmol) and TEA (0.1 mL, 0.7 mmol). The reaction mixture was stirred at rt for 2 h. The reaction mixture was concentrated in vacuo. The residue was dissolved in MeOH, purified by preparative HPLC. Fractions containing the desired product was concentrated in vacuo to give Intermediate 66D as a TFA salt (white solid, 15 mg, 0.028 mmol, 42% yield). LC-MS Anal. Calc'd for $C_{28}H_{31}F_3N_4O_4$ 544.23, found [M+H] 545.3. $T_r$=0.77 min (Method A). $^1$H NMR (400 MHz, METHANOL-d$_4$) δ: 9.07 (d, J=5.3 Hz, 1H), 8.70 (s, 1H), 8.30 (d, J=9.0 Hz, 1H), 8.17 (dd, J=8.9, 1.7 Hz, 1H), 7.97 (d, J=5.3 Hz, 1H), 7.86 (d, J=9.0 Hz, 2H), 7.10-6.84 (m, 2H), 4.28 (d, J=10.6 Hz, 1H), 3.93-3.81 (m, 4H), 3.77-3.59 (m, 1H), 3.55-3.45 (m, 1H), 3.37 (s, 3H), 2.17-1.61 (m, 9H).

Example 66, N-(2-methoxy-1-((1s,4s)-4-(6-(trifluoromethyl)quinolin-4-yl)cyclohexyl)ethyl)-5-(4-methoxyphenyl)-1,3,4-oxadiazol-2-amine The mixture of N-(2-methoxy-1-((1s,4s)-4-(6-(trifluoromethyl)quinolin-4-yl)cyclohexyl)ethyl)-2-(4-methoxybenzoyl)hydrazinecarboxamide, TFA (14 mg, 0.021 mmol) in POCl$_3$ (0.35 mL, 3.75 mmol) was heated at 90° C. over night. The reaction mixture was concentrated in vacuo. The residue was dissolved in MeOH, filtered, and purified via preparative HPLC to give Example 66 (6.4 mg, 0.012 mmol, 55% yield). LC-MS Anal. Calc'd for $C_{28}H_{29}F_3N_4O_3$ 526.22, found [M+H] 527.3, $T_r$=1.67 min (Method B). $^1$H NMR (500 MHz, DMSO-de) δ: 9.00 (d, J=4.4 Hz, 1H), 8.56 (s, 1H), 8.23 (d, J=8.8 Hz, 1H), 8.00 (d, J=8.4 Hz, 1H), 7.74 (d, J=8.7 Hz, 3H), 7.64 (d, J=4.5 Hz, 1H), 7.07 (d, J=8.8 Hz, 2H), 4.07 (br. s., 1H), 3.81 (s, 3H), 3.69-3.47 (m, 2H), 3.29 (s, 3H), 2.05-1.56 (m, 9H), 1.22 (s, 1H).

Example 67

5-(4-Chlorophenyl)-N-(2-methoxy-1-((1s,4s)-4-(6-(trifluoromethyl)quinolin-4-yl)cyclohexyl)ethyl)-1,3,4-oxadiazol-2-amine

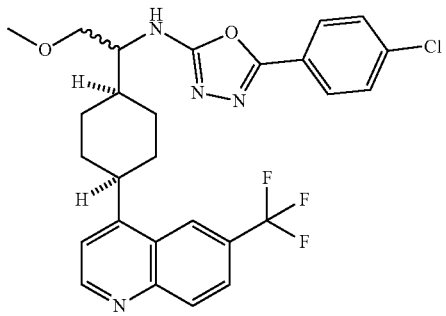 [SMILES: COCC(Nc1nnc(-c2ccc(Cl)cc2)o1)[C@H]1CC[C@@H](c2ccnc3ccc(C(F)(F)F)cc32)CC1]

Example 67 was prepared in a similar method as Example 66.
LC-MS Anal. Calc'd for $C_{27}H_{26}ClF_3N_4O_2$ 530.17, found [M+H] 531.2, $T_r$=1.84 min (Method B). $^1$H NMR (500 MHz, DMSO-d6) δ: 9.01 (d, J=4.5 Hz, 1H), 8.56 (s, 1H), 8.23 (d, J=8.8 Hz, 1H), 8.00 (d, J=8.8 Hz, 1H), 7.91 (d, J=9.1 Hz, 1H), 7.81 (d, J=8.5 Hz, 2H), 7.67-7.53 (m, 3H), 4.10 (br. s., 1H), 3.70-3.48 (m, 2H), 3.29 (s, 3H), 2.05-1.55 (m, 10H).

Example 68, Four Isomers 5-(4-Methoxyphenyl)-N-(1-((1s,4s)-4-(8-(trifluoromethyl)quinolin-4-yl)cyclohexyl)propyl)-1,3,4-oxadiazol-2-amine

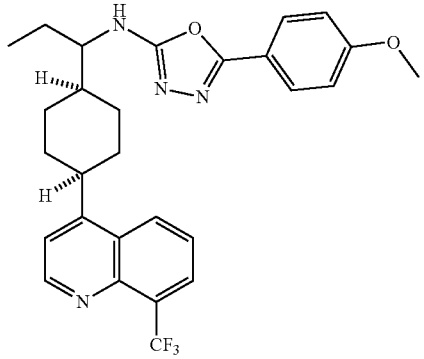 [SMILES: CCC(Nc1nnc(-c2ccc(OC)cc2)o1)[C@H]1CC[C@@H](c2ccnc3c(C(F)(F)F)cccc32)CC1]

68A. Ethyl 2-(4-(8-(trifluoromethyl)quinolin-4-yl)cyclohex-3-enyl)butanoate

To a solution of 4-chloro-8-(trifluoromethyl)quinoline (0.8 g, 3.45 mmol), ethyl 2-(4-(4,4,5,5-tetramethyl-1,3,2-dioxaborolan-2-yl)cyclohex-3-en-1-yl)butanoate (1.135 g, 3.52 mmol) (Intermediate) in 1,4-Dioxane (25 mL) was added potassium carbonate (1.193 g, 8.64 mmol) and Water (5 mL). The reaction mixture was purged with nitrogen stream for 3 min, followed by addition of Pd(Ph$_3$P)$_4$ (0.16 g, 0.14 mmol). The resulting mixture was heated at 100° C. under nitrogen stream for over night. The reaction mixture was cooled down and diluted with ethyl acetate and saturated NaHCO$_3$ solution. The organic layer was separated, and dried over MgSO$_4$. The filtrate was concentrated in vacuo. The extract was purified via silica gel flash column chromatography, eluting with 0-25% ethyl acetate in hexane to give Intermediate 68A (oil, 0.98 g, 2.504 mmol, 72.5% yield). LC-MS Anal. Calc'd for C$_{22}$H$_{24}$F$_3$NO$_2$ 391.17, found [M+H] 392.1. T$_r$=1.15 min (Method A). $^1$H NMR (400 MHz, CHLOROFORM-d) δ: 9.00 (d, J=4.4 Hz, 1H), 8.21 (dd, J=7.6, 4.5 Hz, 1H), 8.07 (d, J=7.3 Hz, 1H), 7.56 (t, J=7.8 Hz, 1H), 7.28 (br. s., 1H), 5.82 (br. s., 1H), 4.22 (q, J=7.0 Hz, 2H), 2.59-1.85 (m, 8H), 1.78-1.68 (m, 2H), 1.32 (td, J=7.1, 1.9 Hz, 3H), 0.97 (t, J=7.4 Hz, 3H)

68B. Ethyl 2-(4-(8-(trifluoromethyl)-1,2,3,4-tetrahydroquinolin-4-yl)cyclohexyl)butanoate The reaction mixture of ethyl 2-(4-(8-(trifluoromethyl)quinolin-4-yl)cyclohex-3-en-1-yl)butanoate (0.95 g, 2.427 mmol) in MeOH (20 mL) was purged with nitrogen stream for 3 min, followed by addition of Pd—C (10% wt., wet) (0.155 g, 0.146 mmol). The resulting mixture was evacuated and then hydrogenated with hydrogen balloon at rt for 20 h. The reaction mixture was filtered and the filter cake was washed with MeOH. The filtrate was concentrated in vacuo. And the residue was purified via silica gel flash column chromatography, eluting with 0-15% ethyl acetate in hexane to give Intermediate 68B (oil, 0.85 g, 2.139 mmol, 88% yield). LC-MS Anal. Calc'd for C$_{22}$H$_{30}$F$_3$NO$_2$ 397.22, found [M+H] 398.2. T$_r$=1.22 min (Method A).

68C. Ethyl 2-((1s,4s)-4-(8-(trifluoromethyl)quinolin-4-yl)cyclohexyl)butanoate To a solution of ethyl 2-(4-(8-(trifluoromethyl)-1,2,3,4-tetrahydroquinolin-4-yl)cyclohexyl)butanoate (0.8 g, 2.013 mmol) in Toluene (20 mL) was added DDQ (0.55 g, 2.415 mmol). The dark purple-red reaction mixture was heated at 100° C. for 2h. The reaction mixture turned into light brown mixture. The reaction mixture was diluted with ethyl acetate and filtered. The filtrate was concentrated in vacuo. and the residue was purified via silica gel flash column chromatography, eluting with 0-20% ethyl acetate in hexane to give product isomer mixture (oil, 0.69 g, 1.754 mmol, 87% yield). The isomers was further separated by SFC to give major isomer as Intermediate 68C (Method: 10% MeOH on chiral IC column). (oil, 0.29 g, 0.737 mmol, 36.6% yield). LC-MS Anal. Calc'd for C$_{22}$H$_{26}$F$_3$NO$_2$ 393.19, found [M+H] 394.1. T$_r$=1.20 min (Method A). $^1$H NMR (400 MHz, CHLOROFORM-d) δ: 9.02 (d, J=4.6 Hz, 1H), 8.30 (d, J=8.6 Hz, 1H), 8.08 (d, J=7.3 Hz, 1H), 7.61 (t, J=7.9 Hz, 1H), 7.46 (d, J=4.6 Hz, 1H), 4.19 (q, J=7.0 Hz, 2H), 3.57-3.30 (m, 1H), 2.64 (td, J=10.8, 4.0 Hz, 1H), 2.17-1.56 (m, 11H), 1.29 (t, J=7.2 Hz, 3H), 0.95 (t, J=7.5 Hz, 3H).

68D. 2-(4-(8-(trifluoromethyl)quinolin-4-yl)cyclohexyl)butanoic acid

To a solution of ethyl 2-(4(8-(trifluoromethyl)quinolin-4-yl)cyclohexyl)butanoate (0.29 g, 0.737 mmol) in THF (5 mL) and MeOH (5 mL) was added LiOH (2.0 M solution) (3.56 mL, 7.12 mmol). The resulting mixture was heated at 70° C. over night. To the reaction mixture was added more LiOH (2.0 M solution) (3.56 mL, 7.12 mmol) and THF (4 mL). The reaction mixture was heated at 70° C. for 30 h. The reaction mixture was cooled down and diluted with water, and 1 N HCl solution to adjust pH to 7, then 2 mL of HOAc was added to adjust pH=5-6. The resulting mixture was extracted with ethyl acetate twice. The organic layer was separated and dried over MgSO$_4$. The filtrate was concentrated in vacuo. to give Intermediate 68D (light brown solid, 0.24 g, 0.657 mmol, 89% yield). LC-MS Anal. Calc'd for C$_{20}$H$_{22}$F$_3$NO$_2$ 365.16, found [M+H] 366.1. T$_r$=0.98 min (Method A). $^1$H NMR (400 MHz, METHANOL-d$_4$) δ: 8.90 (d, J=4.8 Hz, 1H), 8.50 (d, J=8.4 Hz, 1H), 8.12 (d, J=7.3 Hz, 1H), 7.71 (t, J=7.9 Hz, 1H), 7.60 (d, J=4.8 Hz, 1H), 3.62-3.49 (m, 1H), 2.73-2.59 (m, 1H), 1.98-1.34 (m, 11H), 0.98 (t, J=7.4 Hz, 3H).

68E. 2-(4-methoxybenzoyl)-N-(1-((1s,4s)-4-(8-(trifluoromethyl)quinolin-4-yl)cyclohexyl)propyl)hydrazinecarboxamide To a solution of 2-(4-(8-(trifluoromethyl)quinolin-4-yl)cyclohexyl)butanoic acid (0.18 g, 0.493 mmol) in Toluene (6 mL) were added TEA (0.137 mL, 0.985 mmol) and DPPA (0.133 mL, 0.616 mmol). The reaction mixture was heated at 70° C. for 1.5 h. The reaction mixture was concentrated in vacuo. A portion of the residue was used in the following step. To a suspension of 4-methoxybenzohydrazide, HCl (25.4 mg, 0.126 mmol) in THF (1 mL) were added DIPEA (0.135 mL, 0.773 mmol) and a solution of 4-((1s,4s)-4-(I-isocyanatopropyl)cyclohexyl)-8-(trifluoromethyl)quinoline (35 mg, 0.097 mmol). The reaction mixture was stirred at rt for 2 h.

The reaction mixture was concentrated in vacuo and the residue was used in the next step reaction without purification. LC-MS Anal. Calc'd for C$_{28}$H$_{31}$F$_3$N$_4$O$_3$ 528.23, found [M+H] 529.2. T$_r$=0.97 min (Method A).

Example 68 5-(4-Methoxyphenyl)-N-(1-((1s,4s)-4-(8-(trifluoromethyl)quinolin-4-yl)cyclohexyl)propyl)-1,3,4-oxadiazol-2-amine The reaction mixture of 2-(4-methoxybenzoyl)-N-(1-((1s,4s)-4-(8-(trifluoromethyl)quinolin-4-yl)cyclohexyl)propyl)hydrazinecarboxamide (40 mg, 0.076 mmol) in POCl$_3$ (0.6 mL, 6.44 mmol) was heated at 100° C. for 4 h. The reaction mixture was cooled down.

The reaction mixture was concentrated in vacuo. and the residue was dissolved in MeOH, filtered, and purified via preparative HPLC to give Example 68 (26 mg, 0.050 mmol, 66.6% yield). LC-MS Anal. Calc'd for C$_{28}$H$_{29}$F$_3$N$_4$O$_2$ 510.22, found [M+H] 510.9, T$_r$=2.19 min (Method B). $^1$H NMR (500 MHz, DMSO-d$_6$) δ: 8.97 (dd, J=19.8, 4.2 Hz, 1H), 8.56 (d, J=7.7 Hz, 1H), 8.17 (br. s., 1H), 7.81-7.70 (m, 3H), 7.65-7.47 (m, 2H), 7.08 (t, J=8.3 Hz, 2H), 3.94-3.84 (m, 1H), 3.82 (d, J=4.0 Hz, 3H), 2.01-1.37 (m, 12H), 0.93 (d, J=5.4 Hz, 3H).

The diasteromer mixture was further purified by chiral separation (Method M) to give four isomers. Example 68-1, enantiomer 1, T$_r$=25 min over 45 min run (Method N). Example 65-2, enantiomer 2. T$_r$=28 min over 45 min, enantiomer 3. T$_r$=36 min over 45 min, enantiomer 4. T$_r$=42 min over 45 min (absolute stereochemistry was not determined).

First eluant, Example 68-1 (5.9 mg, 0.011 mmol, 15.1% yield). LC-MS Anal. Calc'd for C$_{28}$H$_{29}$F$_3$N$_4$O$_2$ 510.22, found [M+H] 511.2. T$_r$=2.17 min (Method B). $^1$H NMR (500 MHz, DMSO-d$_6$) δ: 8.98 (d, J=4.6 Hz, 1H), 8.54 (d, J=8.5 Hz, 1H), 8.16 (d, J=7.0 Hz, 1H), 7.74 (d, J=8.5 Hz, 3H), 7.62 (d, J=4.3 Hz, 1H), 7.07 (d, J=8.5 Hz, 2H), 3.87 (d, J=10.1 Hz, 1H), 3.81 (s, 3H), 3.58-3.48 (m, 1H), 1.96-1.60 (m, 10H), 1.55-1.36 (m, 1H), 0.92 (t, J=7.2 Hz, 3H).

Second eluant, Example 68-2 (5.1 mg, 0.010 mmol, 12.9% yield). LC-MS Anal. Calc'd for $C_{29}H_{29}F_3N_4O_2$ 510.22, found [M+H] 511.2. $T_r$=2.17 min (Method B). $^1$H NMR (500 MHz, DMSO-d$_6$) δ: 8.98 (d, J=4.6 Hz, 1H), 8.54 (d, J=8.5 Hz, 1H), 8.16 (d, J=7.0 Hz, 1H), 7.74 (d, J=8.5 Hz, 3H), 7.62 (d, J=4.3 Hz, 1H), 7.07 (d, J=8.5 Hz, 2H), 3.87 (d, J=10.1 Hz, 1H), 3.81 (s, 3H), 3.58-3.48 (m, 1H), 1.96-1.60 (m, 10H), 1.55-1.36 (m, 1H), 0.92 (t, J=7.2 Hz, 3H).

Third eluant, Example 68-3 (4.7 mg, 0.009 mmol, 12.0% yield). LC-MS Anal. Calc'd for $C_{28}H_{29}F_3N_4O_2$ 510.22, found [M+H] 511.2. $T_r$=2.16 min (Method B). $^1$H NMR (500 MHz, DMSO-d$_6$) δ: 8.94 (d, J=4.6 Hz, 1H), 8.54 (d, J=8.5 Hz, 1H), 8.16 (d, J=7.0 Hz, 1H), 7.84-7.66 (m, 3H), 7.55 (d, J=4.6 Hz, 1H), 7.09 (d, J=8.8 Hz, 2H), 3.81 (s, 3H), 3.54 (br. s., 1H), 3.46-3.29 (m, 1H), 1.93 (br. s., 4H), 1.74-1.32 (m, 7H), 0.93 (t, J=7.2 Hz, 3H)

Fourth eluant, Example 68-4 (4.7 mg, 0.009 mmol, 12.0% yield). LC-MS Anal. Calc'd for $C_{28}H_{29}F_3N_4O_2$ 510.22, found [M+H] 511.0. $T_r$=2.16 min (Method B). $^1$H NMR (500 MHz, DMSO-d$_6$) δ: 8.94 (d, J=4.6 Hz, 1H), 8.54 (d, J=8.5 Hz, 1H), 8.16 (d, J=7.0 Hz, 1H), 7.84-7.66 (m, 3H), 7.55 (d, J=4.6 Hz, 1H), 7.09 (d, J=8.8 Hz, 2H), 3.81 (s, 3H), 3.54 (br. s., 1H), 3.46-3.29 (m, 1H), 1.93 (br. s., 4H), 1.74-1.32 (m, 7H), 0.93 (t, J=7.2 Hz, 3H)

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press. Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan et al., *Current Protocols in Protein Science*, Vols. 1-2, John Wiley and Sons, Inc., NY (2000)).

Software packages and databases for determining. e.g., antigenic fragments, leader sequences, protein folding, functional domains, glycosylation sites, and sequence alignments, are available (see, e.g., GCG® Wisconsin Package (Accelrys, Inc., San Diego, Calif.); and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 μL PBS containing a protease inhibitor cocktail (Set 2; Calbiochem, EMD Biosciences, San Diego. Calif.). The sonicate can be centrifuged for 10 min at 10,000×g, and the supernatant can be assayed in triplicate by incubating a 40 μl sample with an equal volume of 100 mmol/L potassium phosphate buffer, pH 6.5, containing 40 mmol/L ascorbic acid (neutralized to pH 7.0), 100 μmol/L methylene blue, 200 μg/mL catalase, and 400 μmol/l L-Trp for 30 min at 37° C. The assay can be terminated by the addition of 16 μL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 μg/mL; 500-2,000 units/mL) and 1-α-methyl Trp (1-MT: 40 μmol/L) can be added to the incubation media as indicated. This assay can also form the basis of a cell-based assay, and may be quantified via LCMS/MS as an alternative to UV/Vis detection.

Western Blot Analyses. Groups of 1,000-1,200 islets incubated for 24 h in Miami medium in the presence of cytokines can be harvested and sonicated in PBS as above, and 50 μg protein samples can be electrophoresed on 10% SDS-PAGE gels. COS7 cells (0.6×10$^6$ cells/60 mm3 petri dish) transfected with human-IDO plasmid (3 μg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-STAT$_{1\alpha}$ p91, and STAT$_{1\alpha}$ p91 (1:500; Zymed, San Francisco, Calif.). Immunoreactive proteins can be visualized with ECL PLUS® Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO. Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 μm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt. Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay. cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif.*, 19:22-29 (2000)). To screen for IDO inhibitory activity, compounds can be evaluated at a single concentration of, for example, 200 μM against 50 ng of IDO enzyme in 100 μL reaction volumes with tryptophan added at increasing concentrations at, for example, 0, 2, 20, and 200 μM. Kynurenine production can be measured at 1 hour.

Cell-based Assay. COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^1$ cells per well. The following day, the wells can be washed and new media (phenol red free) containing 20 μg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 μM. More extensive dose-escalation profiles can be collected for select compounds.

Pharmacodynamic and Pharmacokinetic Evaluation. A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 μL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

Evaluation of Biological Activity

Exemplary compounds were tested for inhibition of IDO activity. Experimental procedures and results are provided below.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 μL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20L) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Activity for compounds described herein is provided below, wherein potency levels are provided as follows: (Potency: IDO $IC_{50}$: A<0.05 μM: B<0.25 μM: C<2 μM).

Assessment of inhibitor activity in HeLa cell-based indoleamine 2,3-dioxygenase (IDO) assay:

HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 μg/mL stroptomycin (#SV30010. HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 μL of culture medium. After a further 48 hour incubation, 170 μL of supernatant was transferred from each well to a fresh 96-well plate, 12.1 μL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL of the supernatant was transferred from each well to a fresh 96-well plate. 100 μl of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Activity for compounds described herein is provided below, wherein potency levels are provided as follows: (Potency: IDO $IC_{50}$: A<0.1 μM; B<1 μM C<10 μM)

Results of the IDO assays are shown in the table below.

| Ex. No. | IDO1 HEK Human IC50 (uM) | IDO Hela IC50 (uM) |
|---|---|---|
| 1 | 0.0475 | 0.0148 |
| 2 | 0.0392 | 0.0348 |
| 3 | 0.0423 | 0.0167 |
| 4 | 0.1675 | |
| 5 | 0.0151 | 0.0350 |
| 6 | 0.0370 | |
| 7 | 0.5427 | |
| 8 | 0.0348 | 0.0113 |
| 9 | 0.1924 | |
| 10 | 0.7472 | |
| 11 | 0.0860 | 0.1616 |
| 12 | 0.0225 | 0.0390 |
| 13 | 0.0482 | 0.1176 |
| 14 | 0.0362 | 0.0722 |
| 15 | 0.1245 | |
| 16 | 2.0000 | |
| 17 | 0.2393 | |
| 18 | 0.0663 | 0.0555 |
| 19 | 0.0138 | 0.0055 |
| 20 | 0.1348 | |
| 21 | 0.0682 | |
| 22 | 0.0059 | 0.0088 |
| 23 | 0.0453 | |
| 24 | 0.0055 | 0.0054 |
| 25 | 0.0096 | |
| 26 | 0.0619 | |
| 27 | 0.0090 | |
| 28 | 0.0371 | |
| 29 | 0.0235 | 0.0553 |
| 30 | 0.0106 | 0.0133 |
| 31 | 0.0427 | |
| 32 | 0.0035 | |
| 33 | 0.0641 | |
| 34 | 0.0386 | |
| 35 | 1.0000 | |
| 36 | 0.7291 | |
| 37 | 0.8579 | |
| 38 | | 0.0211 |
| 39 | | 0.2882 |
| 40 | 0.1261 | |
| 41 | 0.0231 | 0.3904 |
| 42 | 0.0572 | |
| 43 | 0.2883 | |
| 44 | 0.0124 | 0.0105 |
| 45 | 0.1821 | |
| 46 | 0.3857 | |
| 47 | 0.0183 | |
| 48 | 0.0036 | |
| 49-1 | 0.0009 | |
| 49-2 | 0.1771 | |
| 50 | 0.1222 | |
| 51 | 0.0711 | |
| 52 | | |
| 53 | 0.1444 | |
| 54 | 0.0688 | |
| 55 | 2.0000 | |
| 56 | 0.0184 | |
| 57-1 | | |
| 57-2 | 0.3303 | |
| 58-1 | | 0.3257 |
| 58-2 | | 0.0074 |
| 59 | 0.0060 | 0.0047 |
| 60 | | 0.0548 |
| 61 | 0.8105 | |
| 62 | 0.0017 | 0.0035 |
| 63-1 | | 0.0262 |
| 63-2 | 0.1409 | |
| 64-1 | | 0.9165 |
| 64-2 | | 0.0089 |
| 65-1 | | 0.0156 |
| 64-2 | | 0.8854 |
| 66 | | |
| 67 | | |
| 68 | | 0.0202 |

What is claimed:

1. A compound of formula I or formula II:

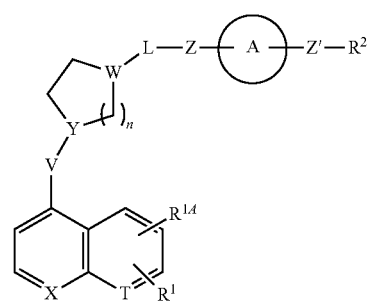

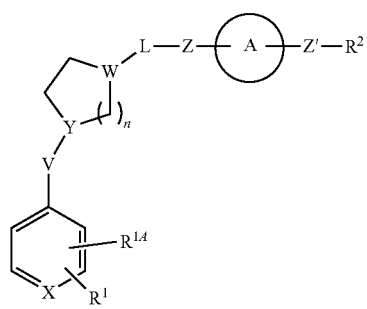

wherein
X is CH or N;
T is CH or N;
V is a bond or O;
Y is CH;
W is —CH—;
n is 0, 1, 2, 3, or 4;
L is a $C_1$-$C_6$alkylene optionally substituted with one, two, or three substituents that are independently $C_1$-$C_6$alkyl or —$C_1$-$C_6$alkO$C_1$-$C_6$alkyl;
Z is a bond, —NH—, or —N($C_1$-$C_6$alkyl);
A is triazolyl, oxadiazolyl, thiadiazolyl, oxazolyl, thiazolyl, or imidazolyl;
Z' is a bond, —NH—, or —N($C_1$-$C_6$alkyl);
$R^1$ is H, halo, $C_1$-$C_6$alkyl, —O$C_1$-$C_6$alkyl, or $C_1$-$C_6$haloalkyl;

$R^{1A}$ is H, halo, $C_1$-$C_6$alkyl, —O$C_1$-$C_6$alkyl, or $C_1$-$C_6$haloalkyl;

$R^2$ is aryl optionally substituted with one, two, or three substituents that are independently halo, —CN, $C_1$-$C_6$alkyl, —O$C_1$-$C_6$alkyl, or heteroaryl optionally substituted with $C_1$-$C_6$alkyl; $C_3$-$C_{10}$cycloalkyl optionally substituted with one, two, or three substituents independently selected from halo, —CN, $C_1$-$C_6$alkyl, —O$C_1$-$C_6$alkyl, or heteroaryl optionally substituted with $C_1$-$C_6$alkyl;$C_1$-Chalk-O-$C_1$-$C_6$alkyl; or heteroaryl optionally substituted with one, two, or three substituents that are independently halo, —CN, $C_1$-$C_6$alkyl, —O$C_1$-$C_6$alkyl, or heteroaryl optionally substituted with $C_1$-$C_6$alkyl;

or a pharmaceutically acceptable salt, a stereoisomer, a tautomer, or a solvate thereof.

2. The compound of claim 1 that is a compound of formula I.

3. The compound of claim 1 that is a compound of formula II.

4. The compound of claim 1, wherein n is 2.

5. The compound of claim 1, wherein V is a bond.

6. The compound of claim 1, wherein L is a Cialkylene substituted with one C1-C6alkyl.

7. The compound of claim 1, wherein Z is a bond.

8. The compound of claim 1, wherein Z is —NH— or —N($C_1$-$C_6$alkyl).

9. The compound of claim 1, wherein Z' is a bond.

10. The compound of claim 1, wherein Z' is —NH—or —N($C_1$-$C_6$alkyl).

11. The compound of claim 1, wherein $R^1$ is H, F, or —$CF_3$.

12. The compound of claim 1, wherein $R^{1A}$ is H.

13. The compound claim 1, wherein $R^2$ is aryl optionally substituted with one, two, or three substituents that are independently halo, —CN, $C_1$-$C_6$alkyl, —O$C_1$-$C_6$alkyl, or heteroaryl optionally substituted with $C_1$-$C_6$alkyl.

14. The compound of claim 1 that is 4-((1s,4s)-4-((R)-1-(5-(4-Chlorophenyl)-4H-1,2,4-triazol-3-yl)ethyl)cyclohexyl)-6-fluoroquinoline;

2-(4-Fluorophenyl)-5-((R)-1-((1s,4s)-4-(6-fluoroquinolin-4-yl)cyclohexyl)ethyl)-1,3,4-oxadiazole;

6-Fluoro-4-((1s,4s)-4-((R)-1-(5-(4-fluorophenyl)-4H-1,2,4-triazol-3-yl)ethyl)cyclohexyl) quinoline;

2-(4-Chlorophenyl)-5-((R)-1-((1s,4s)-4-(6-fluoroquinolin-4-yl)cyclohexyl)ethyl)-1,3,4-oxadiazole;

2-(4-Chlorophenyl)-5-((R)-1-((1s,4S)-4-(6-fluoroquinolin-4-yl)cyclohexyl)ethyl)-1,3,4-thiadiazole;

4-(5-((R)-1-((1s,4S)-4-(6-Fluoroquinolin-4-yl)cyclohexyl)ethyl)-1,3,4-thiadiazol-2-yl)benzonitrile;

N-(4-Fluorophenyl)-5-((R)-1-((1s,4S)-4-(6-fluoroquinolin-4-yl)cyclohexyl)ethyl)-1,3,4-thiadiazol-2-amine;

6-fluoro-4-((1S,4s)-4-((R)-1-(5-(4-methoxyphenyl)-4H-1,2,4-triazol-3-yl)ethyl) cyclohexyl)quinoline;

6-fluoro-4-((1S,4s)-4-((R)- 1-(5-(3-fluoro-4-methylphenyl)-4H-1,2,4-triazol-3-yl)ethyl) cyclohexyl)quinoline;

4-((1S,4s)-4-((R)- 1-(5-(3-chloro-4-fluorophenyl)-4H-1,2,4-triazol-3-yl)ethyl) cyclohexyl)-6-fluoroquinoline;

6-fluoro-4-((1S,4s)-4-((R)-1-(5-(4-isopropoxyphenyl)-4H-1,2,4-triazol-3-yl)ethyl) cyclohexyl)quinoline, 6-fluoro-4-((1S,4s)-4-((R)-1-(5-phenyl-4H-1,2,4-triazol-3-yl)ethyl)cyclohexyl)quinoline;

6-fluoro-4-((1S,4s)-4-((R)- 1-(5-(3-fluorophenyl)-4H-1,2,4-triazol-3-yl)ethyl) cyclohexyl)quinoline;

6-fluoro-4-((1S,4s)-4-((R)- 1-(5-p-tolyl-4H-1,2,4-triazol-3-yl)ethyl)cyclohexyl)quinoline;

2-(3-fluoro-4-methylphenyl)-5-((R)-1-((1s,4S)-4-(6-fluoroquinolin-4-yl)cyclohexyl) ethyl)- 1,3,4-oxadiazole;

2-(3-chloro-4-fluorophenyl)-5-((R)-1-((1s,4S)-4-(6-fluoroquinolin-4-yl)cyclohexyl) ethyl)- 1,3 ,4-oxadiazole;

2-((R)- 1-((1s,4S)-4-(6-fluoroquinolin-4-yl)cyclohexyl) ethyl)-5-(4-isopropoxyphenyl)-1,3,4-oxadiazole;

2-((R)- 1-((1s,4S)-4-(6-fluoroquinolin-4-yl)cyclohexyl) ethyl)-5-phenyl-1,3,4-oxadiazole;

5 -((R)- 1-((1s,4s)-4-(6-Fluoroquinolin-4-yl)cyclohexyl) ethyl)-N-(4-methoxyphenyl)-4H-1,2,4-triazol-3-amine;

N-(4-Fluorophenyl)-5-((R)-1-((1s,4S)-4-(6-fluoroquinolin-4-yl)cyclohexyl)ethyl)-4H-1,2,4-triazol-3-amine;

5-((R)-1-((1s,4s)-4-(6-Fluoroquinolin-4-yl)cyclohexyl) ethyl)-N-phenyl-4H-1,2,4-triazol-3-amine;

5-(4-Chlorophenyl)-N-((R)-1-((1s,4S)-4-(6-fluoroquinolin-4-yl)cyclohexyl)ethyl)-1,3,4-oxadiazol-2-amine;

5-(4-Chlorophenyl)-N-((R)-1-((1s,4S)-4-(6-fluoroquinolin-4-yl)cyclohexyl)ethyl)-1,3,4-thiadiazol-2-amine;

N-((R)-1-((1s,4S)-4-(6-Fluoroquinolin-4-yl)cyclohexyl) ethyl)-5-(4-methoxyphenyl)-1,3,4-oxadiazol-2-amine;

N-((R)-1-((1s,4S)-4-(6-Fluoroquinolin-4-yl)cyclohexyl) ethyl)-5-(4-methoxyphenyl)-1,3,4-thiadiazol-2-amine;

5-Cyclohexyl-N-((R)-1-((1s,4S)-4-(6-fluoroquinolin-4-yl)cyclohexyl)ethyl)-1,3,4-oxadiazol-2-amine;

5-cyclopropyl-N-((R)-1-((1s,4S)-4-(6-fluoroquinolin-4-yl)cyclohexyl)ethyl)-1,3,4-oxadiazol-2-amine;

4-(5-((R)-1-((1s,4S)-4-(6-fluoroquinolin-4-yl)cyclohexyl)ethylamino)-1,3,4-oxadiazol-2-yl)benzonitrile;

N-((R)-1-((1s,4S)-4-(6-fluoroquinolin-4-yl)cyclohexyl) ethyl)-5-(5-methylthiazol-2-yl)-1,3,4-oxadiazol-2-amine;

5-(4-fluorophenyl)-N-((R)-1-((1s,4S)-4-(6-fluoroquinolin-4-yl)cyclohexyl)ethyl)-1,3,4-oxadiazol-2-amine;

N-((R)-1-((1s,4S)-4-(6-fluoroquinolin-4-yl)cyclohexyl) ethyl)-5-(4-methylthiazol-2-yl)-1,3,4-oxadiazol-2-amine;

N-((R)-1-((1s,4S)-4-(6-fluoroquinolin-4-yl)cyclohexyl) ethyl)-5-(6-methoxypyridin-3-yl)-1,3,4-oxadiazol-2-amine;

N-((R)-1-((1s,4S)-4-(6-fluoroquinolin-4-yl)cyclohexyl) ethyl)-5-(methoxymethyl)-1,3,4-oxadiazol-2-amine;

N-((R)-1-((1s,4S)-4-(6-fluoroquinolin-4-yl)cyclohexyl) ethyl)-5-(4-(thiazol-2-yl)phenyl)-1,3,4-oxadiazol-2-amine;

N-((R)-1-((1s,4S)-4-(6-Fluoroquinolin-4-yl)cyclohexyl) ethyl)-4-(4-methoxyphenyl)thiazol-2-amine;

4-(4-Chlorophenyl)-N-((R)-1-((1s,4S)-4-(6-fluoroquinolin-4-yl)cyclohexyl)ethyl)thiazol-2-amine;

5-(4-Chlorophenyl)-N-((R)-1-((1s,4S)-4-(6-fluoroquinolin-4-yl)cyclohexyl)ethyl)oxazol-2-amine;

5-(4-Chlorophenyl)-N-((R)-1-((1s,4S)-4-(6-fluoroquinolin-4-yl)cyclohexyl)ethyl)thiazol-2-amine;

5-(4-Chlorophenyl)-N-((R)-1-((1s,4S)-4-(6-fluoroquinolin-4-yl)cyclohexyl)ethyl)-4H-1,2,4-triazol-3-amine;

4-(5-((R)-1-((1s,4S)-4-(6-Fluoroquinolin-4-yl)cyclohexyl)ethylamino)-4H-1,2,4-triazol-3-yl)benzonitrile;

N-((R)-1-((1s,4S)-4-(6-Fluoroquinolin-4-yl)cyclohexyl) ethyl)-5-(4-methoxyphenyl)-4H-1,2,4-triazol-3-amine;

5-(4-Chlorophenyl)-2-((R)-1-((1s,4S)-4-(6-fluoroquinolin-4-yl)cyclohexyl)ethyl)oxazole;

4-((1s,4s)-4-((R)-1-(5-(4-Chlorophenyl)-1H-imidazol-2-yl)ethyl)cyclohexyl)-6-fluoroquinoline;

5-(4-Fluorophenyl)-2-((R)-1-((1s,4S)-4-(6-fluoroquinolin-4-yl)cyclohexyl)ethyl)oxazole;

4-(2-((R)-1-((1s,4S)-4-(6-Fluoroquinolin-4-yl)cyclohexyl)ethyl)oxazol-5-yl)benzonitrile;

6-Fluoro-4-((1S,4s)-4-((R)-1-(5-(4-fluorophenyl)-1H-imidazol-2-yl)ethyl)cyclohexyl)quinoline;

N-(1-((1s,4s)-4-(6-Fluoroquinolin-4-yl)cyclohexyl)propyl)-5-(4-methoxyphenyl)-1,3,4-oxadiazol-2-amine;

N-(1-((1s,4s)-4-(6-Fluoroquinolin-4-yl)cyclohexyl)propyl)-5-(4-methoxyphenyl)-1,3,4-oxadiazol-2-amine;

N-(1-((1r,4r)-4-(6-Fluoroquinolin-4-yl)cyclohexyl)propyl)-5-(4-methoxyphenyl)-1,3,4-oxadiazol-2-amine;

6-Fluoro-4-(4-(1-(5-(4-isopropoxyphenyl)-4H-1,2,4-triazol-3-yl)propyl)cyclohexyl) quinoline;

2-(1-(4-(6-Fluoroquinolin-4-yl)cyclohexyl)propyl)-5-(4-isopropoxyphenyl)- 1,3,4-oxadiazole;

6-Fluoro-4-(4-(1-(5-(4-isopropoxyphenyl)-4H-1,2,4-triazol-3-yl)propyl)cyclohexyl) quinoline;

2-(1-(4-(6-Fluoroquinolin-4-yl)cyclohexyl)propyl)-5-(4-isopropoxyphenyl)-1,3,4-oxadiazole;

5-(1-(4-(6-Fluoroquinolin-4-yl)cyclohexyl)propyl)-N-(4-methoxyphenyl)-4H-1,2,4-triazol-3-amine;

5-(1-(4-(6-Fluoroquinolin-4-yl)cyclohexyl)propyl)-N-(4-methoxyphenyl)-4H-1,2,4-triazol-3-amine;

N-(2-Ethoxy-1-((1s,4s)-4-(2-fluoro-3-methylpyridin-4-yl)cyclohexyl)ethyl)-5-(4-methoxyphenyl)-1, 3,4-oxadiazol-2-amine;

5-(4-Chlorophenyl)-N-(1-((1s,4s)-4-(6-(trifluoromethyl)quinolin-4-yl)cyclohexyl) propyl)-1,3,4-oxadiazol-2-amine;

5-(4-methoxyphenyl)-N-(1-((1s,4s)-4-(6-(trifluoromethyl)quinolin-4-yl)cyclohexyl) propyl)-1,3,4-oxadiazol-2-amine;

5-(4-methoxyphenyl)-N-(1-((1s,4s)-4-(6-(trifluoromethyl)quinolin-4-yl)cyclohexyl) propyl)-1,3,4-oxadiazol-2-amine;

5-(4-fluorophenyl)-N-(1-((1s,4s)-4-(6-(trifluoromethyl)quinolin-4-yl)cyclohexyl)propyl)-1, 3,4-oxadiazol-2-amine;

5-(4-fluorophenyl)-N-(1-((1s,4s)-4-(6-(trifluoromethyl)quinolin-4-yl)cyclohexyl)propyl)-1, 3,4-oxadiazol-2-amine;

N-(1-((1s,4s)-4-(2-Fluoro-3-methylpyridin-4-yl)cyclohexyl)propyl)-5-(4-methoxyphenyl)-1, 3,4-oxadiazol-2-amine;

5-(4-Methoxyphenyl)-N-((R)-1-((1r,4R)-4-(quinolin-4-yloxy)cyclohexyl)propyl)-1,3,4-oxadiazol-2-amine;

N-(1-((1s,4s)-4-(6-Fluoroquinolin-4-yl)cyclohexyl)-2-methoxyethyl)-5-(4-methoxyphenyl)-1, 3,4-oxadiazol-2-amine;

N-(2-Methoxy-1-((1s,4s)-4-(6-(trifluoromethyl)quinolin-4-yl)cyclohexyl)ethyl)-5-(4-methoxyphenyl)-1, 3,4-oxadiazol-2-amine;

5-(4-Chlorophenyl)-N-(2-methoxy-1-((1s,4s)-4-(6-(trifluoromethyl)quinolin-4-yl) cyclohexyl)ethyl)-1,3,4-oxadiazol-2-amine; or 5-(4-Methoxyphenyl)-N-(1-((1s,4s)-4-(8-(trifluoromethyl)quinolin-4-yl)cyclohexyl)propyl)-1, 3,4-oxadiazol-2-amine;

or a pharmaceutically acceptable salt, a stereoisomer, a tautomer, or a solvate thereof.

15. A pharmaceutical composition comprising a compound according to claim 1 and a pharmaceutically acceptable excipient.

16. The pharmaceutical composition of claim 15, further comprising ipilimumab, nivolumab or pembrolizumab, or a combination thereof.

17. A method of treating cancer in a patient in need of such treatment comprising administering to the patient a therapeutically effective amount of a compound according to claim 1.

* * * * *

UNITED STATES PATENT AND TRADEMARK OFFICE
CERTIFICATE OF CORRECTION

PATENT NO. : 11,351,164 B2
APPLICATION NO. : 16/328473
DATED : June 7, 2022
INVENTOR(S) : Liping Zhang et al.

It is certified that error appears in the above-identified patent and that said Letters Patent is hereby corrected as shown below:

On the Title Page

Column 2 Item (56) (Other Publications), Line 13, delete "al.." and insert -- al., --.

In the Claims

In Claim 1, Column 111, Line 10 (Approx.), delete "$C_6$alkyl;$C_1$" and insert -- $C_6$alkyl; $C_1$ --.

In Claim 1, Column 111, Line 10 (Approx.), delete "Chalk" and insert -- $C_6$alk --.

In Claim 6, Column 111, Line 24, delete "Cialkylene" and insert -- $C_1$alkylene --.

In Claim 6, Column 111, Line 25, delete "C1-C6alkyl." and insert -- $C_1$-$C_6$alkyl. --.

In Claim 13, Column 111, Line 35, delete "compound claim" and insert -- compound of claim --.

In Claim 14, Column 111, Line 61, delete "quinoline," and insert -- quinoline; --.

Signed and Sealed this
Tenth Day of January, 2023

Katherine Kelly Vidal
*Director of the United States Patent and Trademark Office*